United States Patent
Matsushima et al.

(10) Patent No.: US 7,612,208 B2
(45) Date of Patent: Nov. 3, 2009

(54) CRYSTALLINE FORM OF THE SALT OF 4-(3-CHLORO-4-(CYCLOPROPYLAMINOCARBONYL) AMINOPHENOXY)-7-METHOXY-6-QUINOLINECARBOXAMIDE OR THE SOLVATE OF THE SALT AND A PROCESS FOR PREPARING THE SAME

(75) Inventors: Tomohiro Matsushima, Tsukuba (JP); Taiju Nakamura, Kamisu (JP); Kazuhiro Yoshizawa, Kamisu (JP); Atsushi Kamada, Tsukuba (JP); Yusuke Ayata, Kamisu (JP); Naoko Suzuki, Ushiku (JP); Itaru Arimoto, Tokyo (JP); Takahisa Sakaguchi, Tsukuba (JP); Masaharu Gotoda, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 485 days.

(21) Appl. No.: 10/577,531

(22) PCT Filed: Dec. 22, 2004

(86) PCT No.: PCT/JP2004/019223

§ 371 (c)(1),
(2), (4) Date: Apr. 28, 2006

(87) PCT Pub. No.: WO2005/063713

PCT Pub. Date: Jul. 14, 2005

(65) Prior Publication Data

US 2007/0078159 A1  Apr. 5, 2007

(30) Foreign Application Priority Data

Dec. 25, 2003  (JP) ............................ 2003-430939

(51) Int. Cl.
*C07D 215/38* (2006.01)
(52) U.S. Cl. .................. 546/159; 546/153; 514/312
(58) Field of Classification Search .............. 546/153, 546/159; 514/312
See application file for complete search history.

(56) References Cited

U.S. PATENT DOCUMENTS

| 7,253,286 B2 * | 8/2007 | Funahashi et al. ........... 546/153 |
| 2004/0053908 A1 | 3/2004 | Funahashi et al. |
| 2004/0242506 A1 | 12/2004 | Barges Causeret et al. |
| 2004/0253205 A1 | 12/2004 | Yamamoto et al. |
| 2007/0004773 A1 * | 1/2007 | Sakaguchi et al. .......... 514/311 |
| 2007/0078159 A1 | 4/2007 | Matsushima |
| 2007/0117842 A1 * | 5/2007 | Arimoto et al. ............. 514/312 |

FOREIGN PATENT DOCUMENTS

| EP | 0 297 580 A1 | 1/1989 |
| JP | 64-022874 A | 1/1989 |
| JP | 2001-131071 A | 5/2001 |
| JP | 2005-501074 A | 1/2005 |
| WO | WO-02/32872 A1 | 4/2002 |
| WO | WO-03013529 A1 | 2/2003 |
| WO | WO-2004/039782 A1 | 5/2004 |
| WO | WO-2004/080462 A1 | 9/2004 |
| WO | WO-2004/101526 A1 | 11/2004 |
| WO | WO-2005/044788 A1 | 5/2005 |
| WO | WO-2005/063713 A1 | 7/2005 |
| WO | WO-2006/030826 A1 | 3/2006 |

OTHER PUBLICATIONS

English language translation of WO 2006/030826 A1 (Mar. 23, 2006).
Proceedings of the American Association for Cancer Research, vol. 45, Mar. 2004, pp. 1070-1071.
J. K. Haleblian, Journal of Pharmaceutical Sciences, vol. 64, No. 8, Aug. 1975, pp. 1269-1288.
International Preliminary Report on Patentability issued on Jan. 10, 2008, in connection with PCT International Application No. PCT/JP2006/312487.

* cited by examiner

*Primary Examiner*—D. Margaret Seaman
(74) *Attorney, Agent, or Firm*—Birch, Stewart, Kolasch & Birch, LLP

(57) ABSTRACT

A crystal of a 4-(3-chloro-4-(cyclopropylaminocarbonyl) aminophenoxy)-7-methoxy-6-quinolinecarboxamide hydrochloride, hydrobromide, p-toluenesulfonate, sulfate, methanesulfonate or ethanesulfonate, or a solvate thereof.

28 Claims, 21 Drawing Sheets

CRYSTALLINE FORM OF THE SALT OF 4-(3-CHLORO-4-(CYCLOPROPYLAMINOCARBONYL) AMINOPHENOXY)-7-METHOXY-6-QUINOLINECARBOXAMIDE OR THE SOLVATE OF THE SALT AND A PROCESS FOR PREPARING THE SAME

TECHNICAL FIELD

The present invention relates to a crystalline form of the salt of 4-(3-chloro-4-(cyclopropylaminocarbonyl)aminophenoxy)-7-methoxy-6-quinolinecarboxamide or the solvate of the salt and a process for preparing the same.

BACKGROUND ART 4-(3-chloro-4-(cyclopropylaminocarbonyl)aminophenoxy)-7-methoxy-6-quinolinecarboxamide (additional name: 4-[3-chloro-4-(N'-cyclopropylureido)phenoxy]-7-methoxyquinoline-6-carboxamide) is known to exhibit an excellent angiogenesis inhibition as a free-form product, as described in Example 368 of Patent Document 1. 4-(3-chloro-4-(cyclopropylaminocarbonyl)aminophenoxy)-7-methoxy-6-quinolinecarboxamide is also known to exhibit a strong inhibitory action for c-Kit kinase (Non-Patent Document 1, Patent Document 2).

However, there has been a long-felt need for the provision of a c-Kit kinase inhibitor or angiogenesis inhibitor that has high usability as a medicament and superior characteristics in terms of physical properties and pharmacokinetics in comparison with the free-form product of 4-(3-chloro-4-(cyclopropylaminocarbonyl)aminophenoxy)-7-methoxy-6-quinolinecarboxamide.

[Patent Document 1] WO 02/32872
[Patent Document 2] WO 2004/080462
[Non-Patent Document 1] 95th Annual Meeting Proceedings, AACR (American Association for Cancer Research), Volume 45, Page 1070-1071, 2004

DISCLOSURE OF THE INVENTION

Problems to be Solved by the Invention

It is an object of the present invention to provide a crystalline form of the salt of 4-(3-chloro-4-(cyclopropylaminocarbonyl)aminophenoxy)-7-methoxy-6-quinolinecarboxamide or the solvate of the salt which has high usability as a medicament and a process for preparing the same.

Means for Solving the Problems

In order to achieve the above object, the present invention provides the followings:

<1> A crystalline form of 4-(3-chloro-4-(cyclopropylaminocarbonyl)aminophenoxy)-7-methoxy-6-quinolinecarboxamide, wherein said crystalline compound is the hydrochloride of said compound, the hydrobromide of said compound, the p-toluenesulfonate of said compound, the sulfate of said compound, the methanesulfonate of said compound or the ethanesulfonate of said compound, or the solvate of said salt;

<2> A crystalline form of 4-(3-chloro-4-(cyclopropylaminocarbonyl)aminophenoxy)-7-methoxy-6-quinolinecarboxamide methanesulfonate or the solvate of said salt;

<3> A crystalline form of 4-(3-chloro-4-(cyclopropylaminocarbonyl)aminophenoxy)-7-methoxy-6-quinolinecarboxamide ethanesulfonate or the solvate of said salt;

<4> A crystalline form of 4(3-chloro-4-(cyclopropylaminocarbonyl)aminophenoxy)-7-methoxy-6-quinolinecarboxamide methanesulfonate;

<5> A crystalline form of the hydrate of 4-(3-chloro-4-(cyclopropylaminocarbonyl)aminophenoxy)-7-methoxy-6-quinolinecarboxamide methanesulfonate;

<6> A crystalline form of the dimethyl sulfoxide solvate of 4-(3-chloro-4-(cyclopropylaminocarbonyl)aminophenoxy)-7-methoxy-6-quinolinecarboxamide methanesulfonate;

<7> A crystalline form of the acetic acid solvate of 4-(3-chloro-4-(cyclopropylaminocarbonyl)aminophenoxy)-7-methoxy-6-quinolinecarboxamide methanesulfonate;

<8> A crystalline form of 4-(3-chloro-4-(cyclopropylaminocarbonyl)aminophenoxy)-7-methoxy-6-quinolinecarboxamide ethanesulfonate;

<9> A crystalline form of the dimethyl sulfoxide solvate of 4-(3-chloro-4-(cyclopropylaminocarbonyl)aminophenoxy)-7-methoxy-6-quinolinecarboxamide ethanesulfonate;

<10> A crystalline form according to <4> (Form A) having diffraction peaks at diffraction angles (2θ±0.2°) of 9.65° and 18.37° in a powder X-ray diffraction;

<11> A crystalline form according to <4> (Form A) having peaks at chemical shifts of about 162.4 ppm, about 128.0 ppm, about 102.3 ppm and about 9.9 ppm in a $^{13}C$ Solid State Nuclear Magnetic Resonance spectrum;

<11-1> A crystalline form according to <4> (Form A) having a peak at a chemical shift of about 162.4 ppm in a $^{13}C$ Solid State Nuclear Magnetic Resonance spectrum;

<11-2> A crystalline form according to <4> (Form A) having a peak at a chemical shift of about 128.0 ppm in a $^{13}C$ Solid State Nuclear Magnetic Resonance spectrum;

<11-3> A crystalline form according to <4> (Form A) having a peak at a chemical shift of about 102.3 ppm in a $^{13}C$ Solid State Nuclear Magnetic Resonance spectrum;

<11-4> A crystalline form according to <4> (Form A) having a peak at a chemical shift of about 9.9 ppm in a $^{13}C$ Solid State Nuclear Magnetic Resonance spectrum;

<12> A crystalline form according to <4> (Form A) having absorption bands at wavenumbers of 1161±1 $cm^{-1}$ and 1044±1 $cm^{-1}$ in an infrared absorption spectrum;

<12-1> A crystalline form according to <4> (Form A) having an absorption band at a wavenumber of 1161±1 $cm^{-1}$ in an infrared absorption spectrum;

<12-2> A crystalline form according to <4> (Form A) having an absorption band at a wavenumber of 1044±1 $cm^{-1}$ in an infrared absorption spectrum;

<13> A crystalline form according to <4> (Form B) having diffraction peaks at diffraction angles (2θ±0.2°) of 5.72° and 13.84° in a powder X-ray diffraction;

<14> A crystalline form according to <4> (Form B) having absorption bands at wavenumbers of 1068±1 $cm^{-1}$ and 918±1 $cm^{-1}$ in an infrared absorption spectrum;

<14-1> A crystalline form according to <4> (Form B) having an absorption band at a wavenumber of 1068±1 $cm^{-1}$ in an infrared absorption spectrum;

<14-2> A crystalline form according to <4> (Form B) having an absorption band at a wavenumber of 918±1 $cm^{-1}$ in an infrared absorption spectrum;

<15> A crystalline form according to <4> (Form C) having diffraction peaks at diffraction angles (2θ±0.2°) of 14.20° and 17.59° in a powder X-ray diffraction;

<16> A crystalline form according to <4> (Form C) having peaks at chemical shifts of about 160.2 ppm, about 126.6 ppm, about 105.6 ppm and about 7.8 ppm in a $^{13}$C Solid State Nuclear Magnetic Resonance spectrum;

<16-1> A crystalline form according to <4> (Form C) having a peak at a chemical shift of about 160.2 ppm in a $^{13}$C Solid State Nuclear Magnetic Resonance spectrum;

<16-2> A crystalline form according to <4> (Form C) having a peak at a chemical shift of about 126.6 ppm in a $^{13}$C Solid State Nuclear Magnetic Resonance spectrum;

<16-3> A crystalline form according to <4> (Form C) having a peak at a chemical shift of about 105.6 ppm in a $^{13}$C Solid State Nuclear Magnetic Resonance spectrum;

<16-3> A crystalline form according to <4> (Form C) having a peak at a chemical shift of about 7.8 ppm in a $^{13}$C Solid State Nuclear Magnetic Resonance spectrum;

<17> A crystalline form according to <4> (Form C) having absorption bands at wavenumbers of 1324±1 cm$^{-1}$ and 579±1 cm$^{-1}$ in an infrared absorption spectrum;

<17-1> A crystalline form according to <4> (Form C) having an absorption band at a wavenumber of 1324±1 cm$^{-1}$ in an infrared absorption spectrum;

<17-2> A crystalline form according to <4> (Form C) having an absorption band at a wavenumber of 579±1 cm$^{-1}$ in an infrared absorption spectrum;

<18> A crystalline form according to <5> (Form F) having diffraction peaks at diffraction angles (2θ±0.2°) of 8.02° and 18.14° in a powder X-ray diffraction;

<19> A crystalline form according to <7> (Form I) having diffraction peaks at diffraction angles (2θ±0.2°) of 9.36° and 12.40° in a powder X-ray diffraction;

<20> A crystalline form according to <7> (Form I) having absorption bands at wavenumbers of 1750±1 cm$^{-1}$ and 1224±1 cm$^{-1}$ in an infrared absorption spectrum;

<20-1> A crystalline form according to <7> (Form I) having an absorption band at a wavenumber of 1750±1 cm$^{-1}$ in an infrared absorption spectrum;

<20-2> A crystalline form according to <7> (Form I) having an absorption band at a wavenumber of 1224±1 cm$^{-1}$ in an infrared absorption spectrum;

<21> A crystalline form according to <8> (Form α) having diffraction peaks at diffraction angles (2θ±0.2°) at 15.70° and 17.18° in a powder X-ray diffraction;

<22> A crystalline form according to <8> (Form α) having absorption bands at wavenumbers of 1320±1 cm$^{-1}$ and 997±1 cm$^{-1}$ in an infrared absorption spectrum;

<22-1> A crystalline form according to <8> (Form α) having an absorption band at a wavenumber of 1320±1 cm$^{-1}$ in an infrared absorption spectrum;

<22-2> A crystalline form according to <8> (Form α) having an absorption band at a wavenumber of 997±1 cm$^{-1}$ in an infrared absorption spectrum;

<23> A crystalline form according to <8> (Form β) having diffraction peaks at diffraction angles (2θ±0.2°) of 6.48° and 9.58° in a powder X-ray diffraction;

<24> A crystalline form according to <8> (Form β) having absorption bands at wavenumbers of 1281±1 cm$^{-1}$ and 985±1 cm$^{-1}$ in an infrared absorption spectrum;

<24-1> A crystalline form according to <8> (Form β) having an absorption band at a wavenumber of 1281±1 cm$^{-1}$ in an infrared absorption spectrum;

<24-2> A crystalline form according to <8> (Form β) having an absorption band at a wavenumber of 985±1 cm$^{-1}$ in an infrared absorption spectrum;

<25> A process for preparing a crystalline form of 4-(3-chloro-4-(cyclopropylaminocarbonyl)aminophenoxy)-7-methoxy-6-quinolinecarboxamide methanesulfonate (Form A), comprising a step of mixing 4-(3-chloro-4-(cyclopropylaminocarbonyl)aminophenoxy)-7-methoxy-6-quinolinecarboxamide, a solvent and methanesulfonic acid to dissolve;

<25-1> A process according to <25>, wherein the solvent is methanol, ethanol or 2-propanol;

<26> A process for preparing a crystalline form of 4-(3-chloro-4-(cyclopropylaminocarbonyl)aminophenoxy)-7-methoxy-6-quinolinecarboxamide methanesulfonate (Form A), comprising a step of mixing 4-(3-chloro-4-(cyclopropylaminocarbonyl)aminophenoxy)-7-methoxy-6-quinolinecarboxamide, acetic acid and methanesulfonic acid to dissolve;

<26-1> A process according to <26>, further comprising a step of adding a poor solvent to the mixture;

<26-2> A process according to <26-1>, wherein the poor solvent is Methanol or ethanol;

<27> A process for preparing a crystalline form of 4-(3-chloro-4-(cyclopropylaminocarbonyl)aminophenoxy)-7-methoxy-6-quinolinecarboxamide methanesulfonate (Form B), comprising a step of drying a crystalline form of the acetic acid solvate of 4-(3-chloro-4-(cyclopropylaminocarbonyl)aminophenoxy)-7-methoxy-6-quinolinecarboxamide methanesulfonate (Form I) to remove acetic acid;

<28> A process for preparing a crystalline form of 4-(3-chloro-4-(cyclopropylaminocarbonyl)aminophenoxy)-7-methoxy-6-quinolinecarboxamide methanesulfonate (Form C), comprising a step of heating a crystalline form of the dimethyl sulfoxide solvate of 4-(3-chloro-4-(cyclopropylaminocarbonyl)aminophenoxy)-7-methoxy-6-quinolinecarboxamide methanesulfonate;

<29> A process for preparing a crystalline form of 4-(3-chloro-4-(cyclopropylaminocarbonyl)aminophenoxy)-7-methoxy-6-quinolinecarboxamide methanesulfonate (Form C), comprising a step of mixing a crystalline form of the acetic acid solvate of 4-(3-chloro-4-(cyclopropylaminocarbonyl)aminophenoxy)-7-methoxy-6-quinolinecarboxamide methanesulfonate (Form I) and a solvent;

<29-1> A process according to <29>, wherein the solvent is methanol, ethanol or 2-propanol;

<30> A process for preparing a crystalline form of 4-(3-chloro-4-(cyclopropylaminocarbonyl)aminophenoxy)-methoxy-6-quinolinecarboxamide methanesulfonate (Form C), comprising a step of mixing 4-(3-chloro-4-(cyclopropylaminocarbonyl)aminophenoxy)-7-methoxy-6-quinolinecarboxamide, acetic acid and methanesulfonic acid to dissolve;

<30-1> A process according to <30>, further comprising a step of adding a poor solvent to the mixture;

<30-2> A process according to <30-1>, wherein the poor solvent is 2-propanol;

<31> A process for preparing a crystalline form of 4-(3-chloro-4-(cyclopropylaminocarbonyl)aminophenoxy)-7-methoxy-6-quinolinecarboxamide methanesulfonate (Form C), comprising a step of humidifying a crystalline form of 4-(3-chloro-4-(cyclopropylaminocarbonyl)aminophenoxy)-7-methoxy-6-quinolinecarboxamide methanesulfonate (Form B);

<32> A process for preparing a crystalline form of the hydrate of 4-(3-chloro-4-(cyclopropylaminocarbonyl)aminophenoxy)-7-methoxy-6-quinolinecarboxamide methanesulfonate (Form F), comprising a step of mixing 4-(3-chloro-4-(cyclopropylaminocarbonyl)aminophenoxy)-7-methoxy-6-quinolinecarboxamide, acetic acid and methanesulfonic acid to dissolve;

<32-1> A process according to <32>, further comprising a step of adding a poor solvent to the mixture;

<32-2> A process according to <32-1>, wherein the poor solvent is ethyl acetate or isopropyl acetate;

<33> A process for preparing a crystalline form of the acetic acid solvate of 4-(3-chloro-4-(cyclopropylaminocarbonyl)aminophenoxy)-7-methoxy-6-quinolinecarboxamide methanesulfonate (Form I), comprising the step of mixing 4(3-chloro-4-(cyclopropylaminocarbonyl)aminophenoxy)-7-methoxy-6-quinolinecarboxamide, acetic acid and methanesulfonic acid to dissolve;

<33-1> A process according to <33>, further comprising a step of adding a poor solvent to the mixture;

<33-2> A process according to <33-1>, wherein the poor solvent is 1-propanol, 1-butanol or tert-butanol;

<34> A process for preparing a crystalline form of 4-(3-chloro-4-(cyclopropylaminocarbonyl)aminophenoxy)-7-methoxy-6-quinolinecarboxamide ethanesulfonate (Form α), comprising a step of mixing 4-(3-chloro-4-(cyclopropylaminocarbonyl)aminophenoxy)-7-methoxy-6-quinolinecarboxamide, a solvent and ethanesulfonic acid to dissolve;

<34-1> A process according to <34>, wherein the solvent is dimethyl sulfoxide;

<35> A process for preparing a crystalline form of 4-(3-chloro-4-(cyclopropylaminocarbonyl)aminophenoxy)-7-methoxy-6-quinolinecarboxamide ethanesulfonate (Form β), comprising a step of mixing a crystalline form of 4-(3-chloro-4-(cyclopropylaminocarbonyl)aminophenoxy)-7-methoxy-6-quinolinecarboxamide ethanesulfonate (Form α) and a solvent;

<35-1> A process according to <27>, wherein the solvent is methanol, ethanol or 2-propanol;

<36> A process for preparing a crystalline form of 4-(3-chloro-4-(cyclopropylaminocarbonyl)aminophenoxy)-7-methoxy-6-quinolinecarboxamide ethanesulfonate (Form β), comprising a step of mixing 4-(3-chloro-4-(cyclopropylaminocarbonyl)aminophenoxy)-7-methoxy-6-quinolinecarboxamide, acetic acid and ethanesulfonic acid to dissolve;

<36-1> A process according to <36>, further comprising a step of adding a poor solvent and water to the mixture;

<36-2> A process according to <36-1>, wherein the poor solvent is ethanol or 2-propanol;

<37> A pharmaceutical composition, comprising the crystalline form according to any one of <1> to <24-2>;

<38> A prophylactic or therapeutic agent for a disease for which angiogenesis inhibition is effective, comprising the crystalline form according to any one of <1> to <24-2>;

<39> An angiogenesis inhibitor, comprising the crystalline form according to any one of <1> to <24-2>;

<40> An anti-tumor agent, comprising the crystalline form according to any one of <1> to <24-2>;

<41> An anti-tumor agent according to <40>, wherein the tumor is a pancreatic cancer, a gastric cancer, a colon cancer, a breast cancer, a prostate cancer, a lung cancer, a renal cancer, a brain tumor, a blood cancer or an ovarian cancer;

<42> A therapeutic agent for angioma, comprising the crystalline form according to any one of <1> to <24-2>;

<43> A cancer metastasis inhibitor, comprising the crystalline form according to any one of <1> to <24-2>;

<44> A therapeutic agent for retinal neovascularization, comprising the crystalline form according to any one of <1> to <24-2>;

<45> A therapeutic agent for diabetic retinopathy, comprising the crystalline form according to any one of <1> to <24-2>;

<46> A therapeutic agent for an inflammatory disease, comprising the crystalline form according to any one of <1> to <24-2>;

<47> A therapeutic agent for an inflammatory disease according to <46>, wherein the inflammatory disease is deformant arthritis, rheumatoid arthritis, psoriasis or delayed hypersensitivity reaction;

<48> A therapeutic agent for atherosclerosis, comprising the crystalline form according to any one of <1> to <24-2>;

<49> A method for preventing or treating a disease for which angiogenesis inhibition is effective, comprising administering to a patient, a pharmacologically effective dose of the crystalline form according to any one of <1> to <24-2>;

<50> Use of the crystalline form according to any one of <1> to <24-2> for the manufacture of a prophylactic or therapeutic agent for a disease for which angiogenesis inhibition is effective;

<51> A c-Kit kinase inhibitor, comprising the crystalline form according to any one of <1> to <24-2>;

<52> An anti-cancer agent for treating a cancer expressing excessive c-Kit kinase or a mutant c-Kit kinase, comprising the crystalline form according to any one of <1> to <24-2>;

<53> An anti-cancer agent according to <52>, wherein the cancer expressing excessive c-Kit kinase or a mutant c-Kit kinase is acute myelogenous leukemia, mast cell leukemia, a small cell lung cancer, GIST, a testicular tumor, an ovarian cancer, a breast cancer, a brain tumor, neuroblastoma or a colon cancer;

<54> An anti-cancer agent according to <52>, wherein the cancer expressing excessive c-Kit kinase or a mutant c-Kit kinase is acute myelogenous leukemia, a small cell lung cancer or GIST;

<55> An anti-cancer agent according to any one of <52> to <54>, which is applied to a patient for which a cancer expressing excessive c-Kit kinase or a mutant c-Kit kinase is identified;

<56> A therapeutic agent for mastocytosis, allergy or asthma, comprising the crystalline form according to any one of <1> to <24-2>;

<57> A method for treating a cancer, comprising administering to a patient suffering from a cancer expressing excessive c-Kit kinase or a mutant c-Kit kinase, a pharmacologically effective dose of the crystalline form according to any one of <1> to <24-2>;

<58> A method according to <57>, wherein the cancer expressing excessive c-Kit kinase or a mutant c-Kit kinase is acute myelogenous leukemia, mast cell leukemia, a small cell lung cancer, GIST, a testicular tumor, an ovarian cancer, a breast cancer, a brain tumor, neuroblastoma or a colon cancer;

<59> A method according to <57>, wherein the cancer expressing excessive c-Kit kinase or a mutant c-Kit kinase is acute myelogenous leukemia, a small cell lung cancer or GIST;

<60> A method for treating a cancer, comprising the steps of: extracting cancer cells from a patient suffering from cancer; confirming that the cancer cells are expressing excessive c-Kit kinase or a mutant c-Kit kinase; and administering to the patient, a pharmacologically effective dose of the c-Kit kinase inhibitor according to <51>;

<61> A method for treating mastocytosis, allergy, or asthma, comprising administering to a patient suffering from the disease, a pharmacologically effective dose of the c-Kit kinase inhibitor according to <51>;

<62> A method for inhibiting c-Kit kinase activity, comprising applying to a cell expressing excessive c-Kit kinase or a mutant c-Kit kinase, a pharmacologically effective dose of the c-Kit kinase inhibitor according to <51>;

<63> Use of the c-Kit kinase inhibitor according to <51> for the manufacture of an anti-cancer agent for treating a cancer expressing excessive c-Kit kinase or a mutant c-Kit kinase;

<64> Use according to <63>, wherein the cancer expressing excessive c-Kit kinase or a mutant c-Kit kinase is acute myelogenous leukemia, mast cell leukemia, a small cell lung cancer, GIST, a testicular tumor, an ovarian cancer, a breast cancer, a brain tumor, neuroblastoma or a colon cancer;

<65> Use according to <63>, wherein the cancer expressing excessive c-Kit kinase or a mutant c-Kit kinase is acute myelogenous leukemia, a small cell lung cancer or GIST; and <66> Use of the c-Kit kinase inhibitor according to <51> for the manufacture of a therapeutic agent for mastocytosis, allergy or asthma.

EFFECT OF THE INVENTION

A crystalline form of the salt of 4-(3-chloro-4-(cyclopropylaminocarbonyl)aminophenoxy)-7-methoxy-6-quinolinecarboxamide (hereunder, referred to as "carboxamide") or the solvate of the salt according to the present invention has excellent characteristics in terms of physical properties (particularly, dissolution rate) and pharmacokinetics (particularly, bioavailability (BA)), and is extremely useful as an angiogenesis inhibitor or c-Kit kinase inhibitor.

BEST MODE FOR CARRYING OUT THE INVENTION

Figure 1:
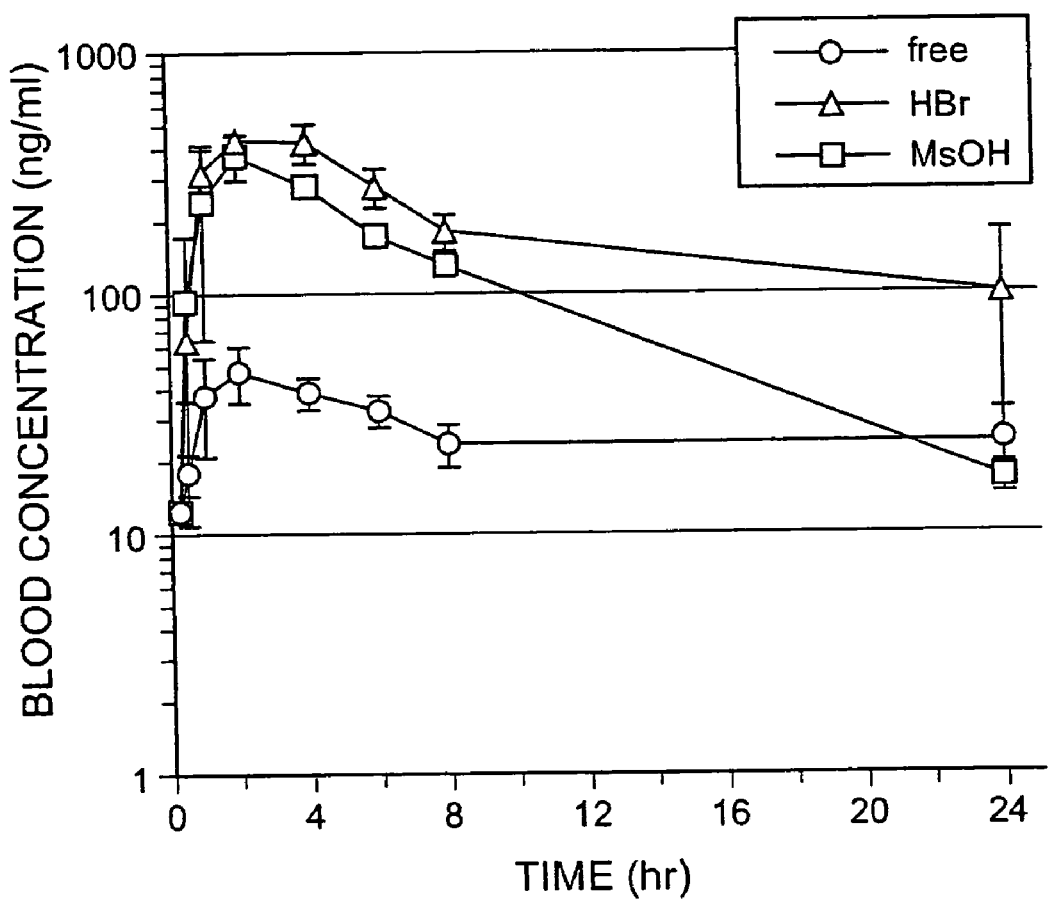
FIG. 1 is a graph illustrating the relation between time and blood concentration in a pharmacokinetic study when a crystalline form of the free form of the carboxamide, a crystalline form of the hydrobromide of the carboxamide, and a crystalline form of the methanesulfonate of the carboxamide (Form A) were administered to beagle dogs.
Figure 2:
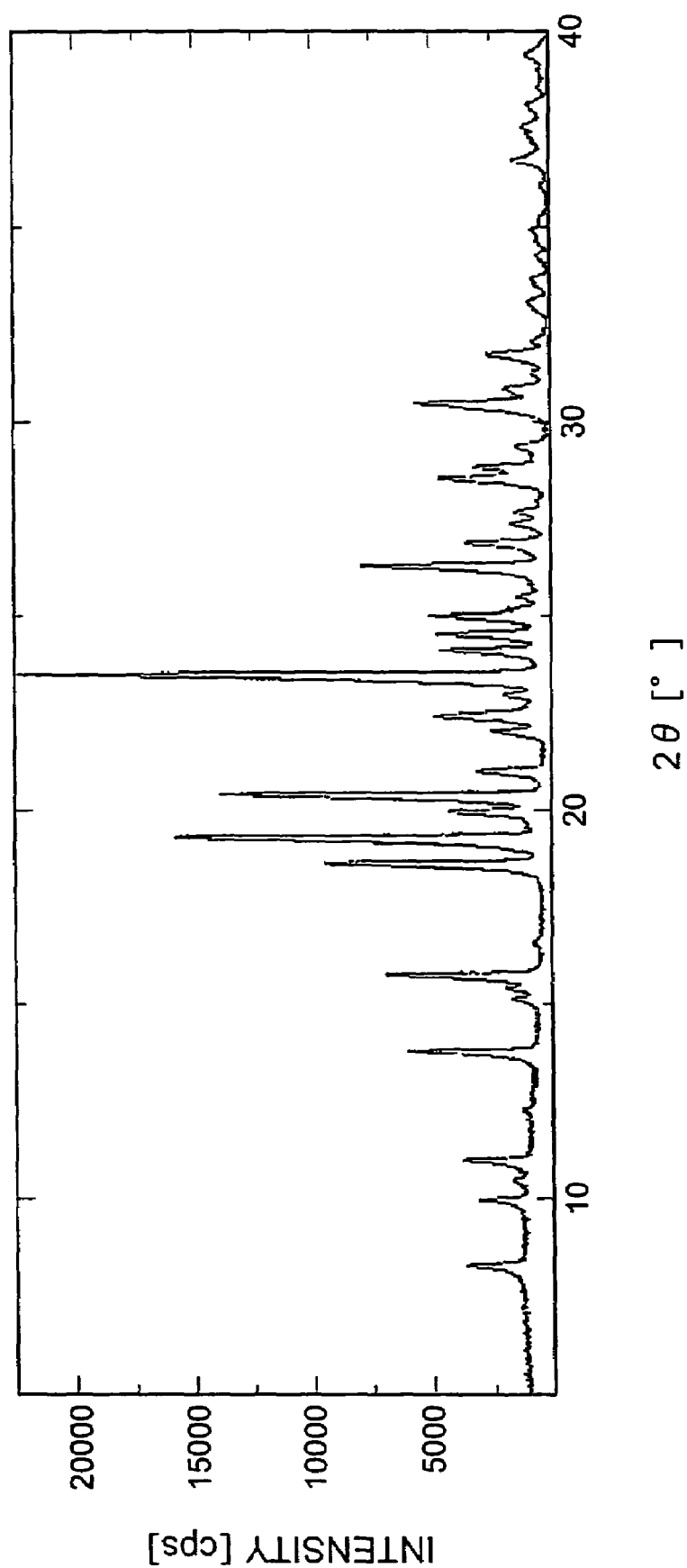
FIG. 2 is a figure illustrating a powder X-ray diffraction pattern for a crystalline form of the free form of the carboxamide obtained in Preparation Example 1.
Figure 3:
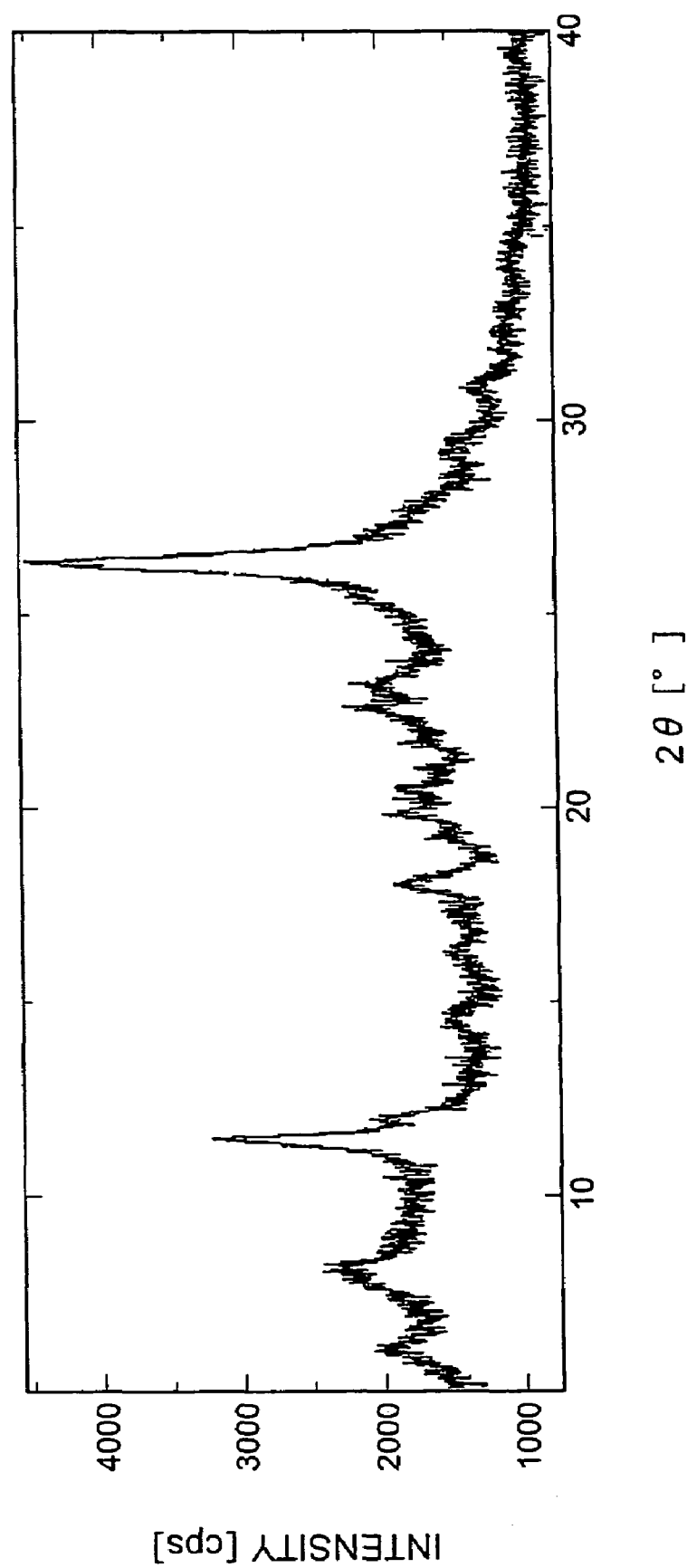
FIG. 3 is a figure illustrating a powder X-ray diffraction pattern for a crystalline form of the hydrochloride of the carboxamide obtain in Example 1.
Figure 4:
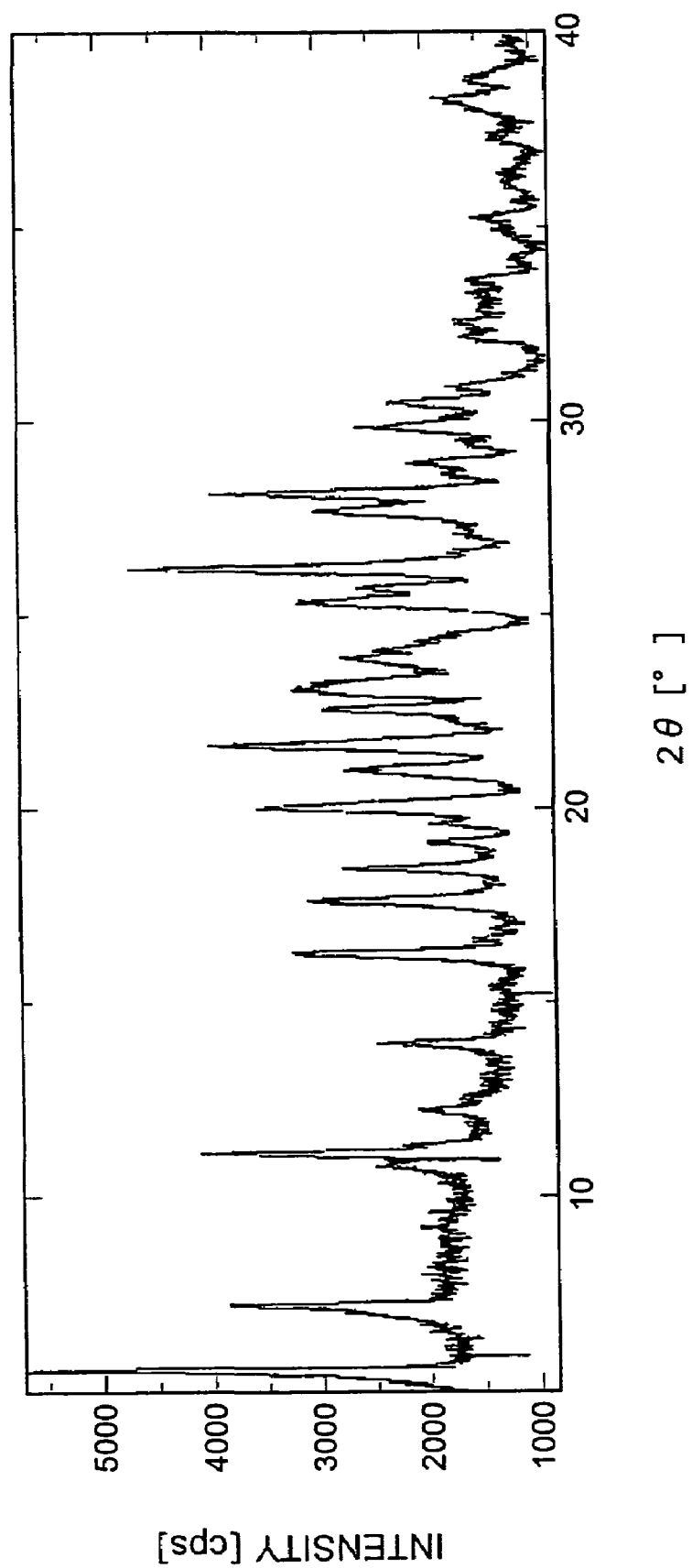
FIG. 4 is a figure illustrating a powder X-ray diffraction pattern for a crystalline form of the hydrobromide of the carboxamide obtained in Example 2.
Figure 5:
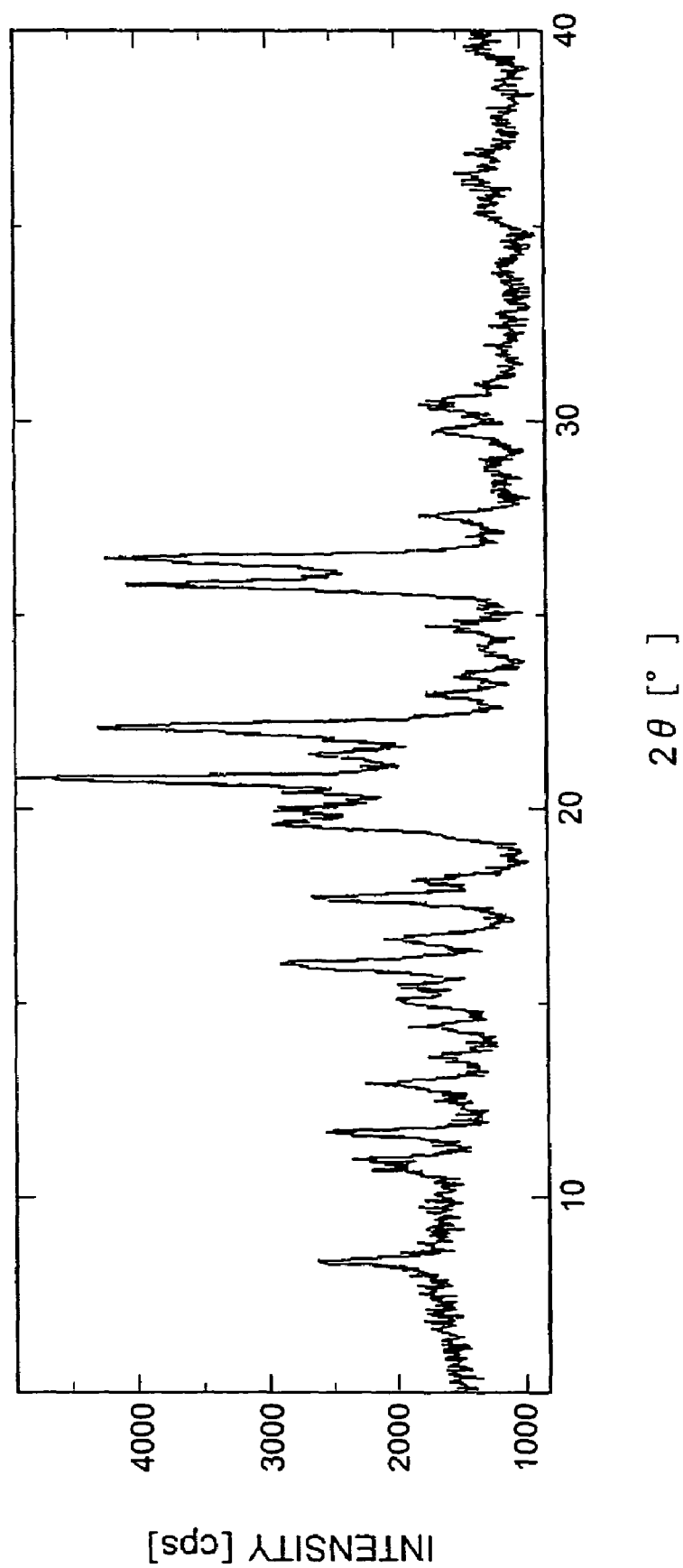
FIG. 5 is a figure illustrating a powder X-ray diffraction pattern of a crystalline form of the p-toluenesulfonate of the carboxamide obtained in Example 3.
Figure 6:
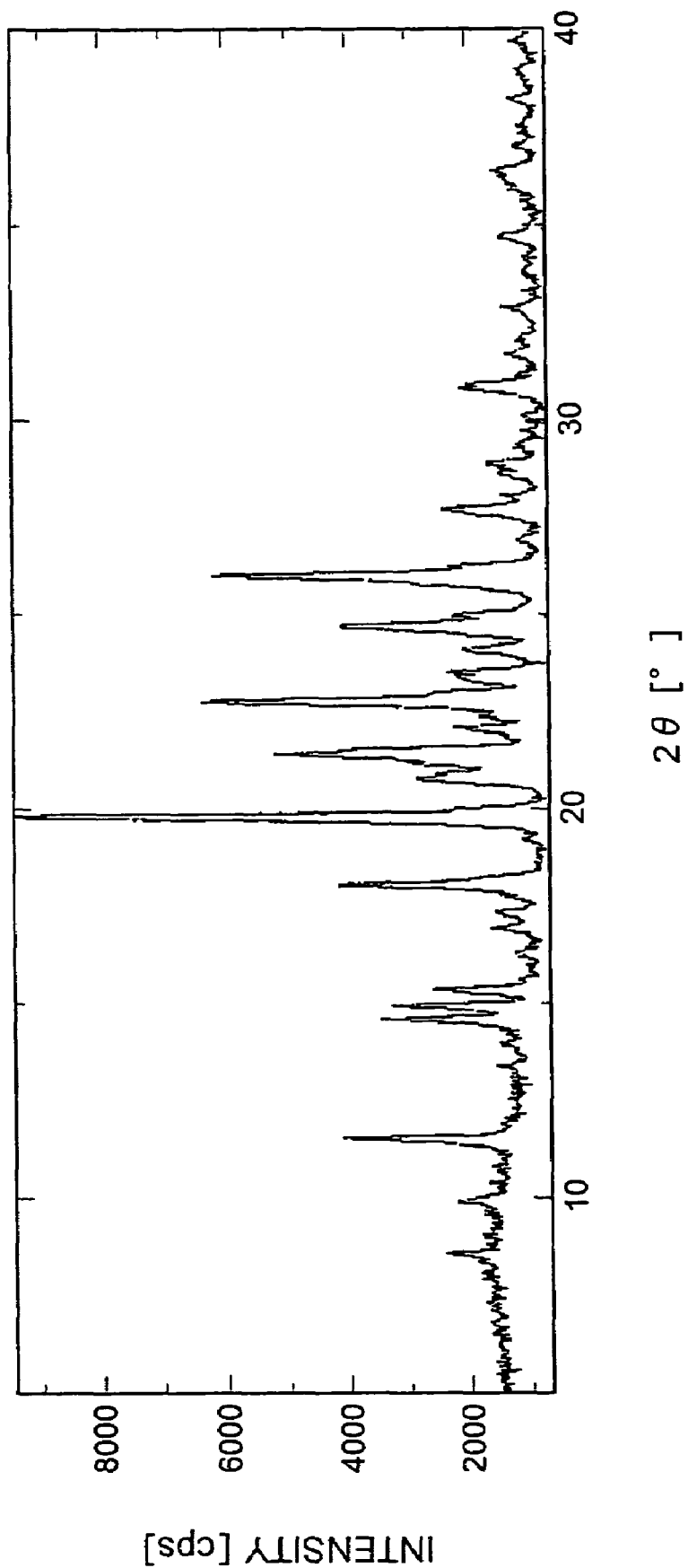
FIG. 6 is a figure illustrating a powder X-ray diffraction pattern for a crystalline form of the sulfate of the carboxamide obtained in Example 4.
Figure 7:
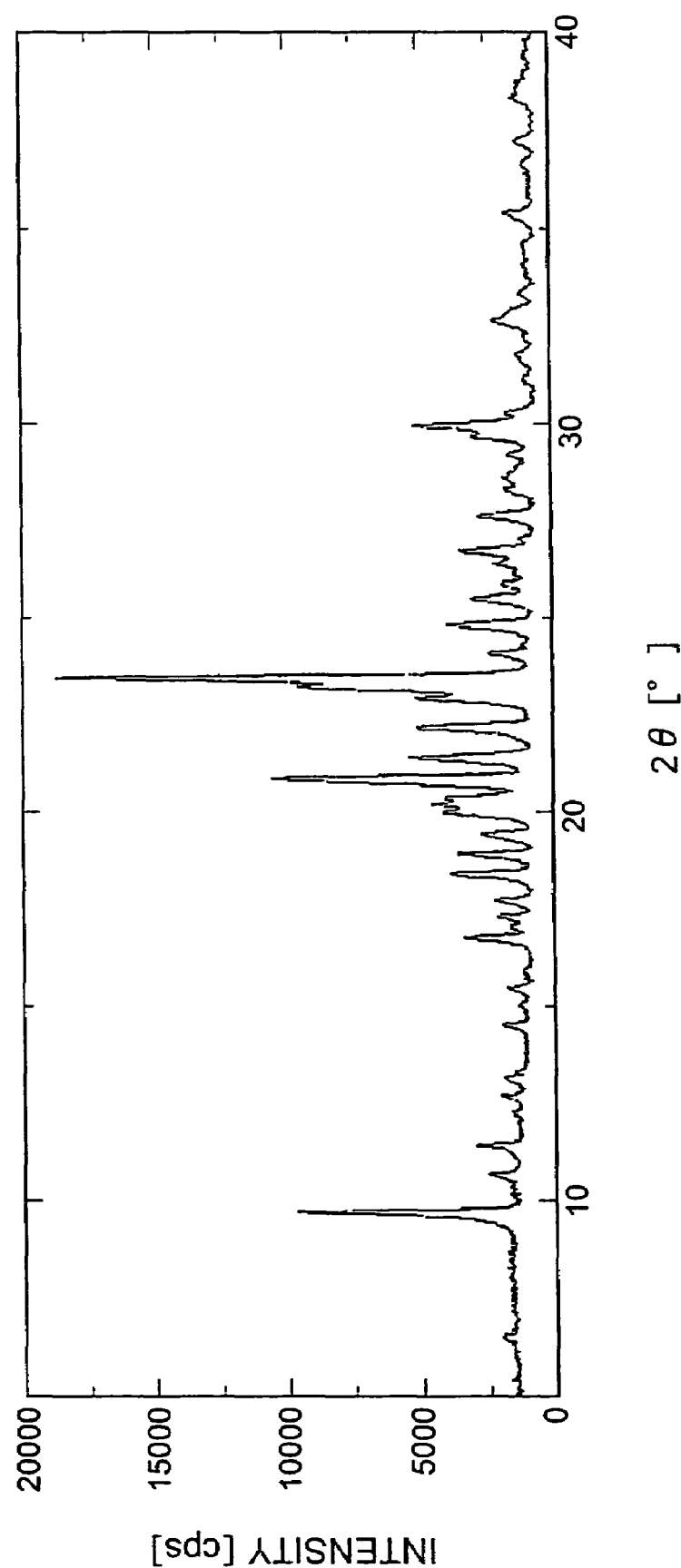
FIG. 7 is a figure illustrating a powder X-ray diffraction pattern for a crystalline form of the methanesulfonate of the carboxamide (Form A) obtained in Example 5.
Figure 8:
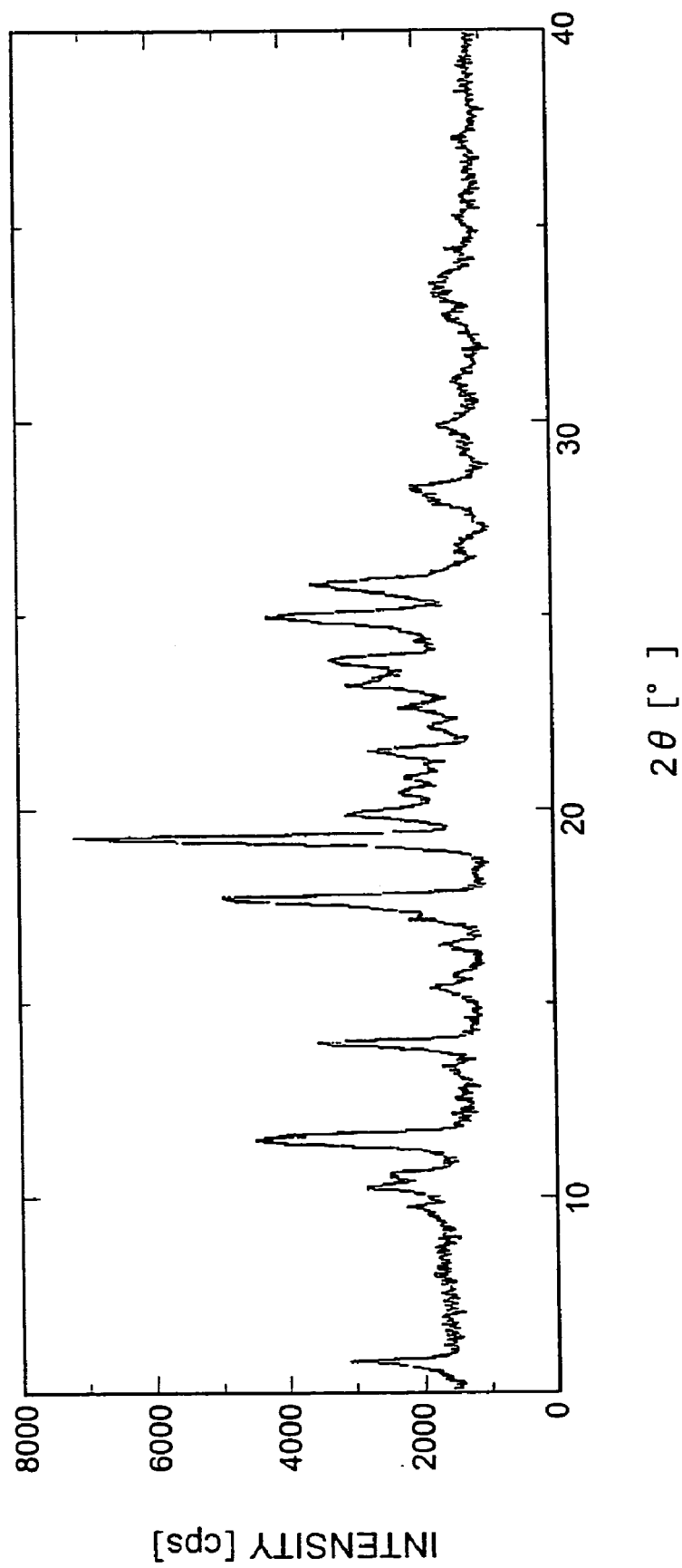
FIG. 8 is a figure illustrating a powder X-ray diffraction pattern for a crystalline form of the methanesulfonate of the carboxamide (B) obtained in Example 6.
Figure 9:
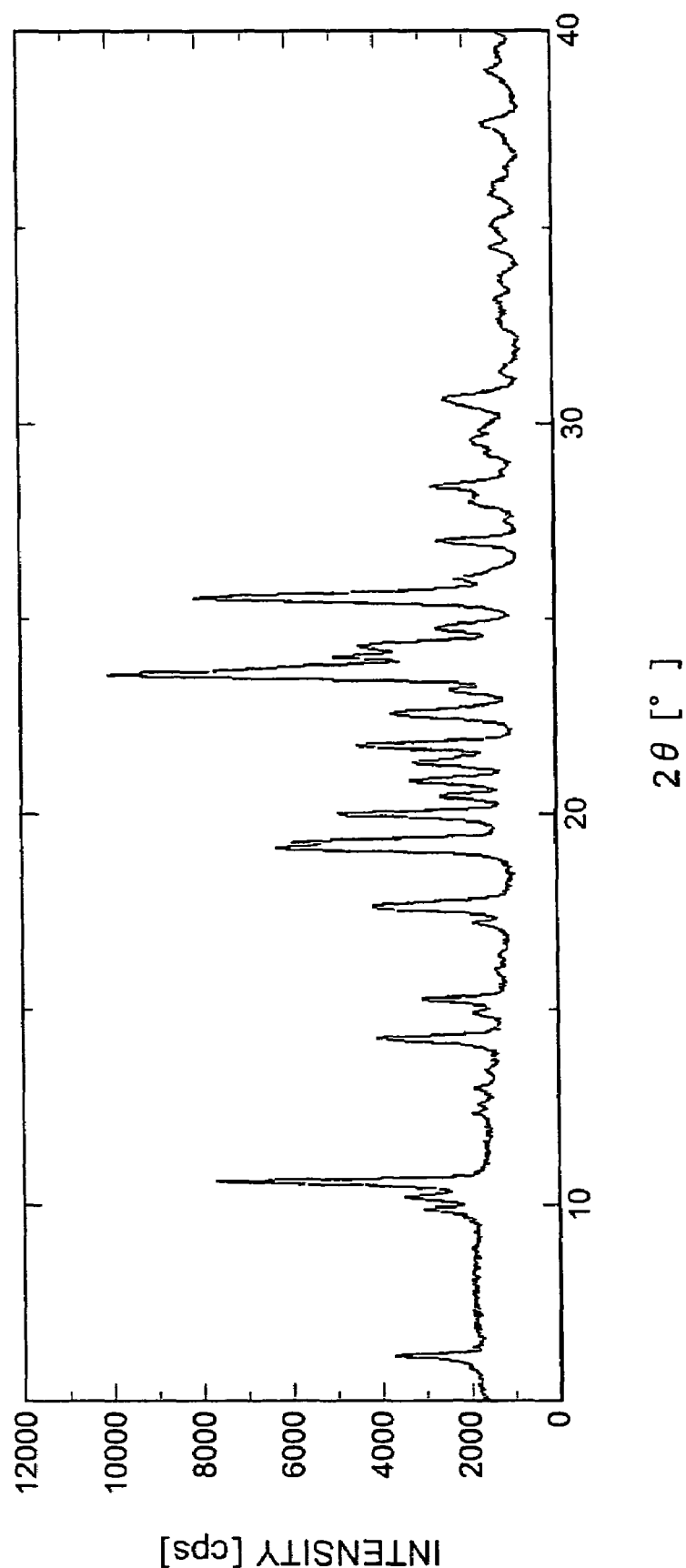
FIG. 9 is a figure illustrating a powder X-ray diffraction pattern for a crystalline form of the methanesulfonate of the carboxamide (Form C) obtained in Example 7.
Figure 10:
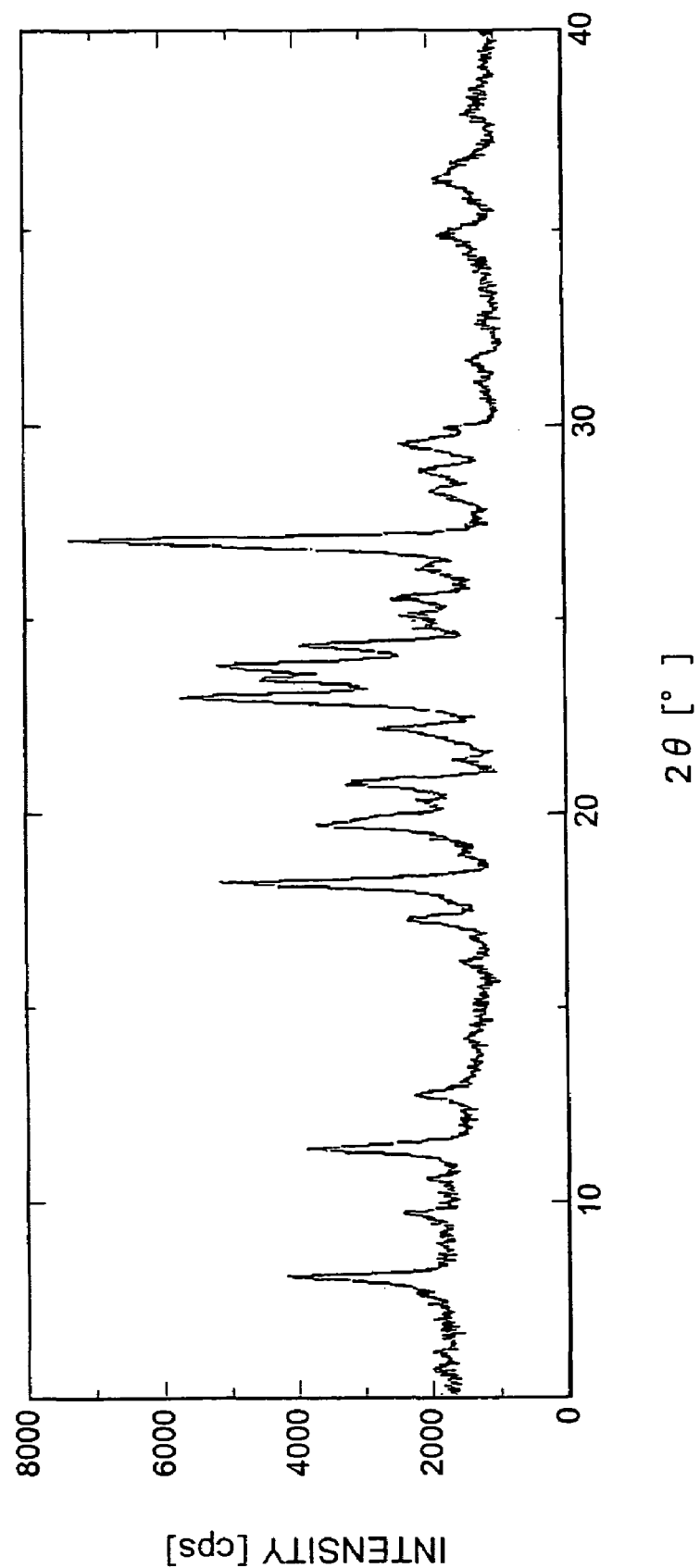
FIG. 10 is a figure illustrating a powder X-ray diffraction pattern for a crystalline form of the hydrate of the methanesulfonate of the carboxamide (Form F) obtained in Example 9.
Figure 11:
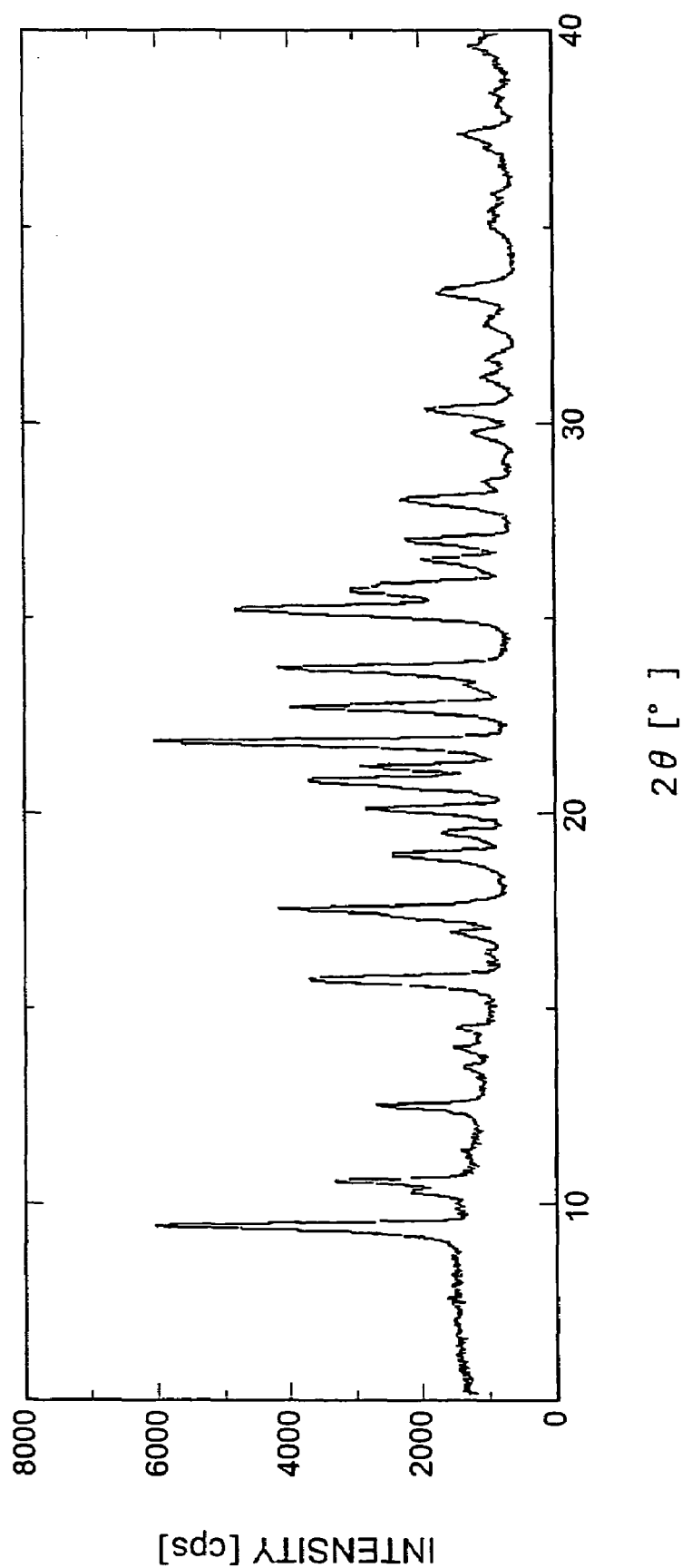
FIG. 11 is a figure illustrating a powder X-ray diffraction pattern for a crystalline form of the acetic acid solvate for the methanesulfonate of the carboxamide (Form I) obtained in Example 10.
Figure 12:
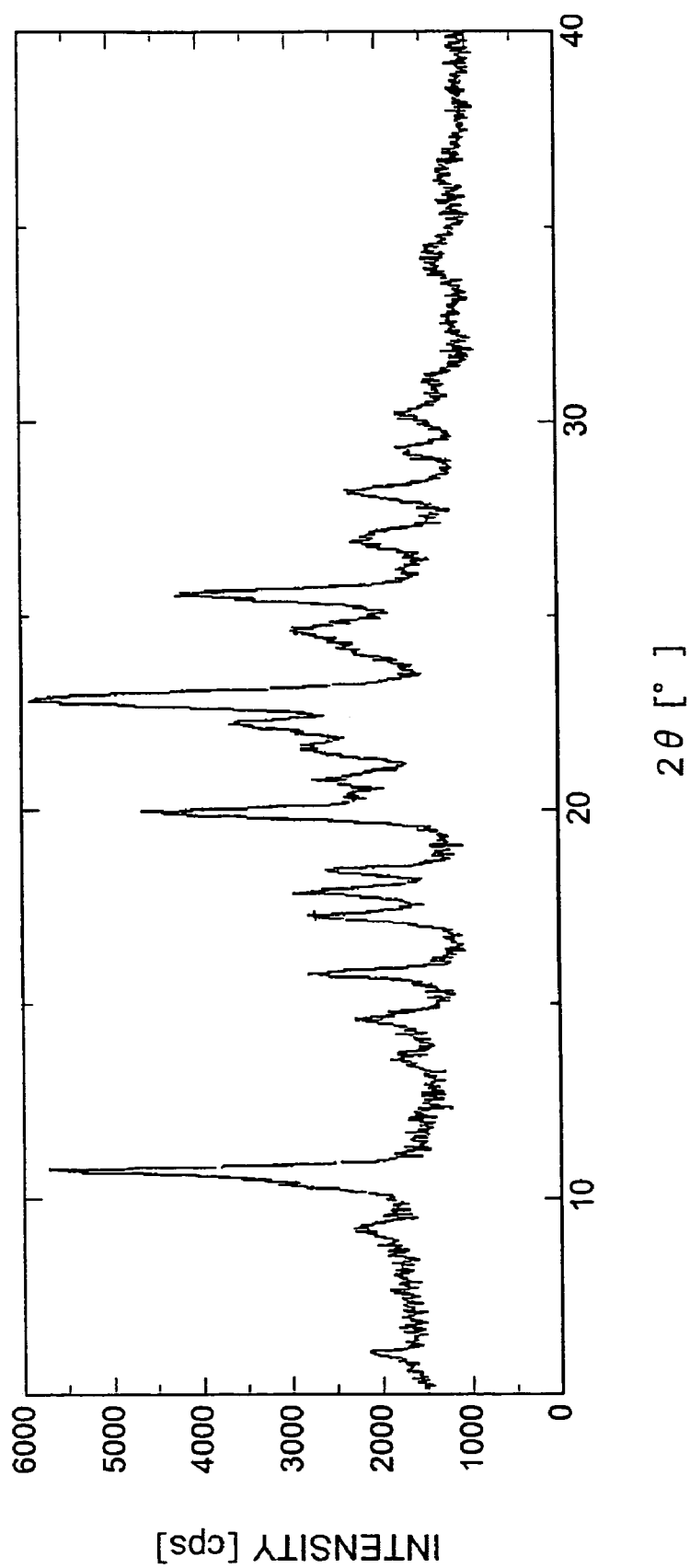
FIG. 12 is a figure illustrating a powder X-ray diffraction pattern for a crystalline form of the ethanesulfonate of the carboxamide (Form α) obtained in Example 11.
Figure 13:
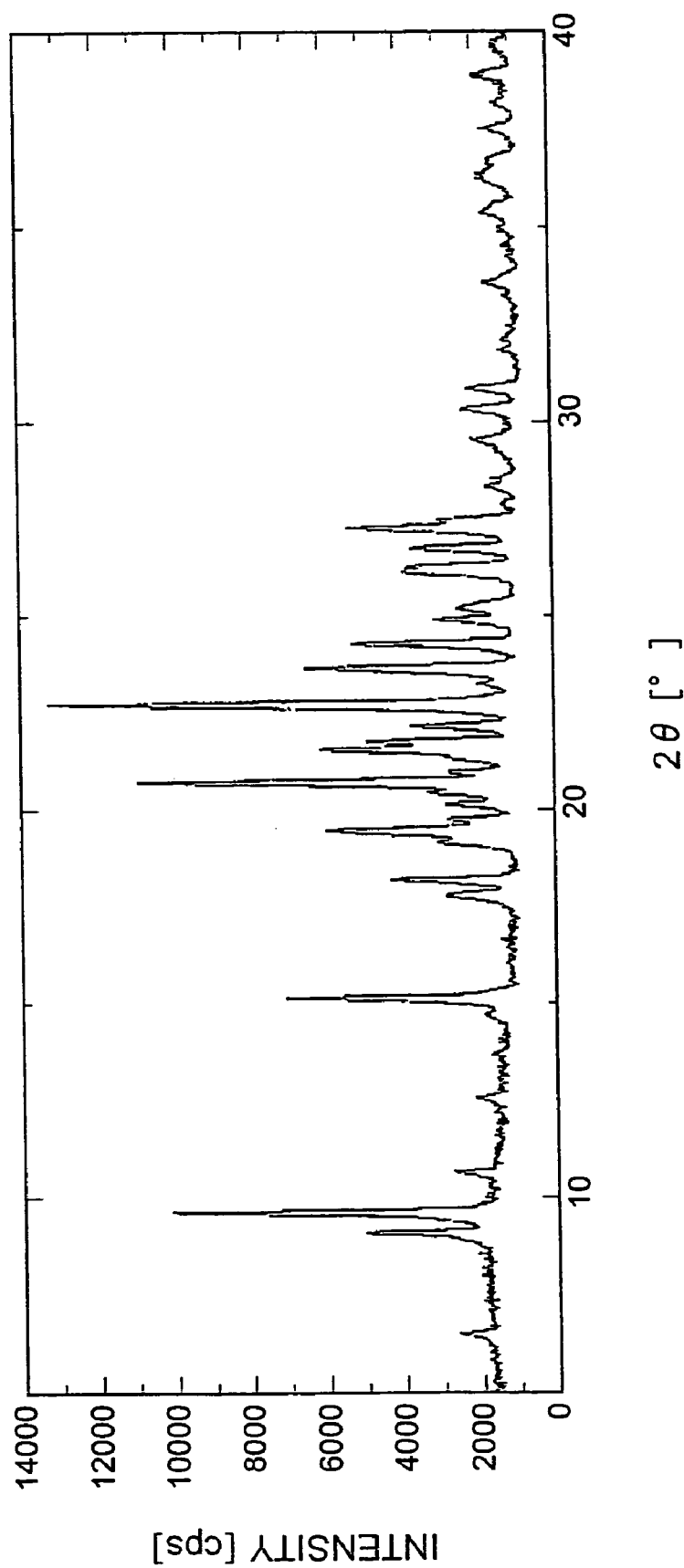
FIG. 13 is a figure illustrating a powder X-ray diffraction pattern for a crystalline form of the ethanesulfonate of the carboxamide (Form β) obtained in Example 12.

Hereunder, the present invention is described in detail.

As examples of the salts of 4-(3-chloro-4-(cyclopropylaminocarbonyl)aminophenoxy)-7-methoxy-6-quinolinecarboxamide (hereunder, referred to as "carboxamide") according to the present invention, methanesulfonate, ethanesulfonate, p-toluenesulfonate, hydrochloride, hydrobromide, sulfate, tartrate and phosphate may be mentioned.

The salt of the carboxamide according to the present invention can be prepared by ordinary methods (for example, by mixing the carboxamide and the corresponding acid at a suitable ratio in the presence or absence of a solvent).

In this connection, in addition to the method described in WO 02/32872, the carboxamide can also be prepared by the method described in Preparation Examples 1 to 3 below.

As examples of the solvate of the salt of the carboxamide according to the present invention, a hydrate, a dimethyl sulfoxide solvate, an acetic acid solvate, and an N,N-dimethylformamide solvate may be mentioned.

In general, since an error within a range of ±0.2° can occur for a diffraction angle (2θ) in powder X-ray diffraction, it is necessary that the above diffraction angle values are understood to also include numerical values within a range of ±0.2° thereof. Therefore, the present invention encompasses crystals for which the diffraction angle matches within an error range of ±0.2° in powder X-ray diffraction, as well as crystals for which the diffraction angle is completely matching in powder X-ray diffraction.

In the present specification, the phrase "having diffraction peaks at diffraction angles (2θ±0.2°) of 9.65° and 18.37°" means "having diffraction peaks at diffraction angles (2θ) of 9.45° to 9.85° and 18.17° to 18.57°", the phrase "having diffraction peaks at diffraction angles (2θ±0.2°) of 5.72° and 13.84°" means "having diffraction peaks at diffraction angles (2θ) of 5.52° to 5.92° and 13.64° to 14.04°", the phrase "having diffraction peaks at diffraction angles (2θ±0.2°) of 14.20° and 17.59°" means "having diffraction peaks at diffraction angles (2θ) of 14.00° to 14.40° and 17.39°", the phrase "having diffraction peaks at diffraction angles (2θ±0.2°) of 8.02° and 18.14°" means "having diffraction peaks at diffraction angles (2θ) of 7.82° to 8.22° and 17.94° to 18.34°", the phrase "having diffraction peaks at diffraction angles (2θ±0.2°) of 9.36° and 12.40°" means "having diffraction peaks at diffraction angles (2θ) of 9.16° to 9.56° and 12.20° and 12.60°", the phrase "having diffraction peaks at diffraction angles (2θ±0.2°) of 15.70° and 17.18°" means "having diffraction peaks at diffraction angles (2θ) of 15.50° to 15.90° and 16.98° to 17.38°", and the phrase "having diffraction peaks at diffraction angles (2θ±0.2°) of 6.48° and 9.58°" means "having diffraction peaks at diffraction angles (2θ) of 6.28° to 6.68° and 9.38° to 9.78°".

In the present specification, the phrase "having a peak at a chemical shift of about 162.4 ppm" means "having a peak substantially equivalent to 162.4 ppm when a $^{13}C$ Solid State Nuclear Magnetic Resonance spectrum (hereinafter abbreviated as 'a $^{13}C$ Solid State NMR spectrum') is measured under normal conditions", the phrase "having a peak at a chemical shift of about 128.0 ppm" means "having a peak substantially equivalent to 128.0 ppm when a $^{13}C$ Solid State NMR spectrum is measured under normal conditions", the phrase "having a peak at a chemical shift of about 102.3 ppm" means "having a peak substantially equivalent to 102.3 ppm when a $^{13}C$ Solid State NMR spectrum is measured under normal conditions", and the phrase "having a peak at a chemical shift of about 9.9 ppm" means "having a peak substantially equivalent to 9.9 ppm when a $^{13}C$ Solid State NMR spectrum is measured under normal conditions".

In the present specification, the phrase "having a peak at a chemical shift of about 160.2 ppm" means "having a peak substantially equivalent to 160.2 ppm when a $^{13}C$ Solid State NMR spectrum is measured under normal conditions", the phrase "having a peak at a chemical shift of about 126.6 ppm" means "having a peak substantially equivalent to 126.6 ppm when a $^{13}C$ Solid State NMR spectrum is measured under normal conditions", the phrase "having peak at a chemical shift of about 105.6 ppm" means "having a peak substantially equivalent to 105.6 ppm when a $^{13}C$ Solid State NMR spectrum is measured under normal conditions", and the phrase "having a peak at a chemical shift of about 7.8 ppm" means "having a peak substantially equivalent to 7.8 ppm when a $^{13}C$ Solid State NMR spectrum is measured under normal conditions".

In the present specification, the phrase "having an absorption band at a wavenumber of 1161±1 $cm^{-1}$" means "having an absorption band at a wavenumber of 1160 $cm^{-1}$ to 1162 $cm^{-1}$", the phrase "having an absorption band at a wavenumber of 1044±1 $cm^{-1}$" means "having an absorption band at a wavenumber of 1043 $cm^{-1}$ to 1045 $cm^{-1}$".

In the present specification, the phrase "having an absorption band at a wavenumber of 1068±1 $cm^{-1}$" means "having an absorption band at a wavenumber of 1067 $cm^{-1}$ to 1069 $cm^{-1}$", the phrase "having an absorption band at a wavenumber of 918±1 $cm^{-1}$" means "having an absorption band at a wavenumber of 917 $cm^{-1}$ to 919 $cm^{-1}$".

In the present specification, the phrase "having an absorption band at a wavenumber of 1324±1 $cm^{-1}$" means "having an absorption band at a wavenumber of 1323 $cm^{-1}$ to 1325 $cm^{-1}$", the phrase "having an absorption band at a wavenumber of 579±1 $cm^{-1}$" means "having an absorption band at a wavenumber of 578 $cm^{-1}$ to 580 $cm^{-1}$".

In the present specification, the phrase "having an absorption band at a wavenumber of 1750±1 $cm^{-1}$" means "having an absorption band at a wavenumber of 1749 $cm^{-1}$ to 1751 $cm^{-1}$", the phrase "having an absorption band at a wavenumber of 1224±1 $cm^{-1}$" means "having an absorption band at a wavenumber of 1223 $cm^{-1}$ to 1225 $cm^{-1}$".

In the present specification, the phrase "having an absorption band at a wavenumber of 1320±1 $cm^{-1}$" means "having an absorption band at a wavenumber of 1319 $cm^{-1}$ to 1321 $cm^{-1}$", the phrase "having an absorption band at a wavenumber of 997±1 $cm^{-1}$" means "having an absorption band at a wavenumber of 996 $cm^{-1}$ to 998 $cm^{-1}$".

In the present specification, the phrase "having an absorption band at a wavenumber of 1281±1 $cm^{-1}$" means "having an absorption band at a wavenumber of 1280 $cm^{-1}$ to 1282 $cm^{-1}$", the phrase "having an absorption band at a wavenumber of 985±1 $cm^{-1}$" means "having an absorption band at a wavenumber of 984 $cm^{-1}$ to 986 $cm^{-1}$".

[General Process for Preparation]

A process for preparing a crystalline form of the salts of carboxamide or the solvate of the salts according to the present invention is described in detail hereunder.

1. Process for Preparing a Crystalline Form of the Hydrochloride or Hydrobromide A crystalline form of the hydrochloride or hydrobromide can be prepared by mixing the carboxamide and a solvent to dissolve, and followed by adding thereto hydrochloric acid or hydrobromic acid.

More specifically, for example, after mixing the carboxamide and a solvent and heating the mixture to dissolve the carboxamide, hydrochloric acid or hydrobromic acid is added thereto and the mixture is then cooled slowly to room temperature to give a crystalline form of the hydrochloride or hydrobromide.

As a solvent, an alcohol such as methanol, ethanol, 1-propanol or 2-propanol can be used, and preferably ethanol is used. Where necessary, the alcohol may be used after adding water thereto.

Although the amount of solvent is not particularly limited, preferably the amount used is 10- to 30-fold relative to the substrate amount, and more preferably 20-fold.

The amount of hydrochloric acid or hydrobromic acid used can be 1.0 to 1.5 equivalents relative to the substrate amount, and an equivalent of 1.1 is preferable.

While a heating temperature is not particularly limited, preferably the heating temperature is between 60° C. and reflux temperature, and more preferably reflux temperature.

Slow cooling from the heating temperature to room temperature can be performed in a period between 10 min and 24 hours.

2. Process for Preparing a Crystalline Form of the p-toluenesulfonate or Sulfate A crystalline form of the sulfate or p-toluenesulfonate can be prepared by mixing the carboxamide, a solvent and sulfuric acid or p-toluenesulfonic acid to dissolve the carboxamide.

More specifically, for example, a crystalline form of the p-toluenesulfonate or sulfate can be prepared by mixing the carboxamide, a solvent and p-toluenesulfonic acid or sulfuric acid, heating the mixture to dissolve the carboxamide, and then slowly cooling the mixture to room temperature.

As a solvent, for example, dimethyl sulfoxide, N,N-dimethylformamide, N,N-dimethylacetamide can be used, and dimethyl sulfoxide is preferable.

Although the amount of solvent is not particularly limited, preferably the amount used is 10- to 30-fold relative to the substrate amount, and more preferably 20-fold.

The amount of p-toluenesulfonic acid or sulfuric acid used can be 1.0 to 1.5 equivalents relative to the substrate amount, and an equivalent of 1.2 is preferable.

While a heating temperature is not particularly limited, the heating temperature is preferably between 60° C. and reflux temperature, more preferably between 70 and 100° C., and further preferably 80° C.

Slow cooling from the heating temperature to room temperature can be performed in a period between 10 min and 24 hours.

3. Process for Preparing a Crystalline Form of the Methanesulfonate (Form A)

(Preparation Method 1)

A crystalline form of the methanesulfonate (Form A) can be prepared by mixing the carboxamide, a solvent and methanesulfonic acid to dissolve the carboxamide.

More specifically, a crystalline form of the methanesulfonate (Form A) can be prepared, for example, by mixing the carboxamide, a solvent and methanesulfonic acid, and heating the mixture to dissolve the carboxamide, and then slowly cooling the mixture to room temperature.

As a solvent, for example, methanol, ethanol, 2-propanol can be used, and methanol is preferable.

Although the amount of solvent is not particularly limited, preferably the amount used is 10- to 30-fold relative to the substrate amount, and more preferably 20-fold.

The amount of methanesulfonic acid used can be 1.0 to 1.5 equivalents relative to the substrate amount, and an equivalent of 1.2 is preferable.

While a heating temperature is not particularly limited, the heating temperature is preferably between 60° C. and reflux temperature, and more preferably between 70 and 80° C.

Slow cooling from a heating temperature to room temperature can be performed in a period between 1 and 24 hours, and preferably in a period between 3 and 12 hours.

(Preparation Method 2)

A crystalline form of the methanesulfonate (Form A) can be prepared by mixing the carboxamide, acetic acid and methanesulfonic acid to dissolve the carboxamide.

More specifically, a crystalline form of the methanesulfonate (Form A) can be prepared, for example, by mixing the carboxamide, acetic acid and methanesulfonic acid, heating the mixture to dissolve the carboxamide, adding a poor solvent and slowly cooing the mixture to room temperature.

Preferably, seed crystals of a crystalline form of the methanesulfonate (Form A) are added when the poor solvent is added.

Although the amount of acetic acid is not particularly limited, preferably the amount used is 5- to 20-fold relative to the substrate amount, and more preferably 10-fold.

The amount of methanesulfonic acid used can be 1.0 to 2.5 equivalents relative to the substrate amount, and an equivalent of 1.4 to 2.2 is preferable.

As a poor solvent, for example, methanol and ethanol can be used, and ethanol is preferred.

Although the amount of poor solvent is not particularly limited, preferably the amount used is 10-fold to 30-fold relative to substrate amount, and more preferably 20-fold. Further, the poor solvent can be added at one time or can be added dividedly 2 to 4 times, and preferably the poor solvent is divided and added 2 times. In this case, the ratio for the amount of solvent added the first time and the amount of solvent added the second time is from 1:1 to 3:1, and preferably 3:2.

Although a heating temperature is not particularly limited, preferably the temperature is between 50° C. and reflux temperature, and more preferably 50° C.

Slow cooling from a heating temperature to room temperature can be performed in a period between 10 min and 6 hours, and preferably in a period between 1 and 2 hours.

4. Process for Preparing a Crystalline Form of the Methanesulfonate (Form B)

A crystalline form of the methanesulfonate (Form B) can be prepared by drying a crystalline form of the acetic acid solvate of the methanesulfonate (Form I) by a method such as drying under aeration to remove acetic acid.

5. Process for Preparing a Crystalline form of the Methanesulfonate (Form C)

(Preparation Method 1)

A crystalline form of the methanesulfonate (Form C) can be prepared by heating a crystalline form of the dimethyl sulfoxide solvate of the methanesulfonate and slowly cooling to room temperature.

This preparation method can be carried out in the presence or absence of a solvent.

When using a solvent, examples of a solvent that can be used include ethyl acetate, isopropyl acetate and n-butyl acetate, and n-butyl acetate is preferable.

Although a heating temperature is not particularly limited, preferably the temperature is between 70° C. and reflux temperature, and more preferably reflux temperature.

(Preparation Method 2)

A crystalline form of the methanesulfonate (Form C) can be prepared by mixing a crystalline form of the acetic acid solvate of the methanesulfonate (Form I) and a solvent, and stirring the mixture.

As a solvent, for example, an alcohol such as methanol, ethanol, or 2-propanol can be used, and ethanol is preferable.

Although a stirring temperature is not particularly limited, preferably the temperature is between 20 and 60° C., and more preferably 40° C.

(Preparation Method 3)

A crystalline form of the methanesulfonate (Form C) can be prepared by mixing the carboxamide, acetic acid and methanesulfonic acid to dissolve the carboxamide.

More specifically, a crystalline form of the methanesulfonate (Form C) can be prepared, for example, by mixing the carboxamide, acetic acid and methanesulfonic acid, heating the mixture to dissolve the carboxamide, and then adding 2-propanol as a poor solvent and slowly cooling the solution to around 15° C. Preferably, seed crystals of a crystalline form of the methanesulfonate (Form C) are added when the poor solvent is added, and isopropyl acetate is further added to accelerate precipitation.

Although the amount of acetic acid is not particularly limited, preferably the amount used is 5- to 10-fold relative to the substrate amount, and more preferably 7- to 8-fold.

The amount of methanesulfonic acid used can be an equivalent of 1.0 to 1.5 relative to the substrate amount, and an equivalent of 1.2 is preferable.

Although the amount of poor solvent is not particularly limited, preferably the amount used is 2- to 10-fold relative to the substrate amount, and more preferably 4- to 5-fold.

When adding isopropyl acetate, although the amount thereof is not particularly limited, a preferable amount is 2- to 10-fold relative to the substrate amount, and more preferably 5-fold.

Although a heating temperature is not particularly limited, a preferably temperature is 40° C.

Slow cooling from a heating temperature to around 15° C. can be performed in a period between 10 min and 6 hours, and preferably in a period between 1 and 2 hours.

(Preparation Method 4)

A crystalline form of the methanesulfonate (Form C) can be prepared by mixing the carboxamide, acetic acid and methanesulfonic acid to dissolve the carboxamide.

More specifically, a crystalline form of the methanesulfonate (Form C) can be prepared, for example, by mixing the carboxamide, acetic acid and methanesulfonic acid, dissolving the carboxamide at room temperature (or around 30° C.), adding 2-propanol as a poor solvent, slowly cooling the mixture to around 15° C., filtering off precipitated crystals, and mixing and stirring the crystals and a solvent. Preferably, seed crystals of a crystalline form of the methanesulfonate (Form C) are added when the poor solvent is added.

Although the amount of acetic acid is not particularly limited, preferably the amount used is 5- to 20-fold relative to the substrate amount, and more preferably 10-fold.

The amount of methanesulfonic acid used can be an equivalent of 1.0 to 2.5 relative to the substrate amount, and an equivalent of 1.8 to 2.2 is preferable.

Although the amount of poor solvent is not particularly limited, preferably the amount used is 10- to 30-fold relative to the substrate amount, and more preferably 20-fold.

Slow cooling from room temperature (or around 30° C.) to around 15° C. can be preformed in a period between 10 min and 4 hours, and preferably in a period between 30 min and 2 hours.

As a solvent to be mixed with the crystals which are filtered off, for example, an alcohol such as methanol, ethanol or 2-propanol can be used, and ethanol is preferred.

(Preparation Method 5)

A crystalline form of the methanesulfonate (Form C) can be prepared by humidifying a crystalline form of the methanesulfonate (Form B).

6. Process for Preparing a Crystalline Form the Dimethyl Sulfoxide Solvate of the Methanesulfonate A crystalline form of the dimethyl sulfoxide solvate of the methanesulfonate can be prepared by mixing the carboxamide, dimethyl sulfoxide and methanesulfonic acid, heating the mixture to dissolve the carboxamide, adding a poor solvent, and slowly cooling the mixture to around 15° C. Preferably, seed crystals of a crystalline form of the methanesulfonate (Form A) are added when the poor solvent is added.

Although the amount of the dimethyl sulfoxide is not particularly limited, preferably the amount used is 5- to 20-fold relative to the substrate amount, and more preferably 8- to 10-fold.

The amount of methanesulfonic acid used can be an equivalent of 1.0 to 4.0 relative to the substrate amount, and an equivalent of 1.2 to 3.5 is preferable.

As a poor solvent, for example, ethyl acetate, isopropyl acetate, 1-propanol, 2-propanol can be used, and preferably ethyl acetate or 2-propanol is used.

Although the amount of poor solvent is not particularly limited, preferably the amount used is 10- to 30-fold relative to the substrate amount, and more preferably 20-fold. Further, the poor solvent can be added at one time or can be added dividedly 2 to 4 times, and preferably the poor solvent is divided and added 2 times. In this case, the ratio for the amount of solvent added the first time and the amount of solvent added th second time is from 1:1 to 1:5, and preferably 1:4.

Although a heating temperature is not particularly limited, preferably the temperature is between 50 and 100° C., and more preferably between 60 and 80° C.

Slow cooling from a heating temperature to around 15° C. can be performed in a period between 10 min and 6 hours, and preferably in a period between 1 and 2 hours.

7. Process for Preparing a Crystalline of the Hydrate of the Methanesulfonate (Form F)

A crystalline form of the hydrate of the methanesulfonate (Form F) can be prepared by mixing the carboxamide, acetic acid and methanesulfonic acid and to dissolve the carboxamide.

More specifically, a crystalline form of the hydrate of the methanesulfonate (Form F) can be prepared, for example, by mixing the carboxamide, acetic acid and methanesulfonic acid, heating the mixture to dissolve the carboxamide, adding a poor solvent, and then slowly cooling the mixture to room temperature. Preferably, seed crystals of a crystalline of the methanesulfonate (Form A) are added when the poor solvent is added.

Although the amount of acetic acid is not particularly limited, preferably the amount used is 5- to 20-fold relative to the substrate amount, and more preferably 10-fold.

The amount of methanesulfonic acid used can be an equivalent of 1.0 to 2.0 relative to the substrate amount, and an equivalent of 1.3 to 1.6 is preferable.

As a poor solvent, for example, ethyl acetate, isopropyl acetate can be used, and ethyl acetate is preferable.

Although the amount of poor solvent is not particularly limited, preferably the amount used is 10- to 30-fold relative to the substrate amount, and more preferably 20-fold. Further, the poor solvent can be added at one time or can be added dividedly 2 to 4 times, and preferably the poor solvent is divided and added 2 times. In this case, the ratio for the amount of solvent added the first time and the amount of solvent added the second time is from 1:1 to 1:5, and a ratio of 1:3 is preferable.

Although a heating temperature is not particularly limited, preferably the temperature is between 40 and 60° C., and more preferably 50° C.

Slow cooling from a heating temperature to room temperature can be performed in a period between 10 min and 6 hours, and preferably in a period between 2 and 4 hours.

8. Process for Preparing a Crystalline Form of the Acetic Acid Solvate of the Methanesulfonate (Form I)

A crystalline form of the acetic acid solvate of the methanesulfonate (Form I) can be prepared by mixing the carboxamide, acetic acid and methanesulfonic acid to dissolve the carboxamide.

More specifically, a crystalline form of the acetic acid solvate of the methanesulfonate (Form I) can be prepared, for example, by mixing the carboxamide, acetic acid and methanesulfonic acid, heating the mixture to dissolve the carboxamide, adding a poor solvent, and slowly cooling the mixture to room temperature. Preferably, seed crystals of a crystalline form of the methanesulfonate (Form C) are added when the poor solvent is added, and isopropyl acetate is further added to accelerate precipitation.

Although the amount of acetic acid is not particularly limited, preferably the amount used is 5- to 10-fold relative to the substrate amount, and more preferably 7- to 8-fold.

The amount of methanesulfonic acid used can be an equivalent of 1.0 to 1.5 relative to the substrate amount, and an equivalent of 1.2 is preferable.

As a poor solvent, for example, 1-propanol, 1-butanol, tert-butanol can be used, and 1-propanol is preferred.

Although the amount of poor solvent is not particularly limited, a preferably amount is 5- to 20-fold relative to the substrate amount, and more preferably 8- to 10-fold. Further, the poor solvent can be added at one time or can be added dividedly 2 to 4 times, and preferably the poor solvent is divided and added 2 times. In this case, the ratio for the amount of solvent added the first time and the amount of solvent added the second time is from 1:1 to 1:5, and a ratio of 1:3.5 is preferable.

When adding isopropyl acetate, although the amount thereof is not particularly limited, a preferable amount is 2- to 10-fold relative to the substrate amount, and more preferably 5-fold.

Although a heating temperature is not particularly limited, a preferable temperature is 40° C.

Slow cooling from a heating temperature to room temperature can be performed in a period between 10 min and 6 hours, and preferably in a period between 1 and 2 hours.

9. Process for Preparing a Crystalline Form of the Ethanesulfonate (Form α)

A crystalline form of the ethanesulfonate (Form α) can be prepared by mixing the carboxamide, a solvent and ethanesulfonic acid to dissolve the carboxamide.

More specifically, a crystalline form of the ethanesulfonate (Form α) can be prepared, for example, by mixing the carboxamide, a solvent and ethanesulfonic acid, heating the mixture to dissolve the carboxamide, adding a poor solvent, and then cooling this solution to room temperature.

As a solvent, for example, dimethyl sulfoxide can be used.

Although the amount of solvent is not particularly limited, a preferable amount is 5- to 20-fold relative to the substrate amount, and more preferably 10-fold.

The amount of ethanesulfonic acid used can be an equivalent of 1.0 to 1.5 relative to the substrate amount, and an equivalent of 1.2 is preferable.

As a poor solvent, for example, ethyl acetate can be used.

Although the amount of poor solvent is not particularly limited, preferably the amount used is 5- to 20-fold relative to the substrate amount, and more preferably 10-fold.

Although a heating temperature is not particularly limited, a preferably temperature is between 50 and 70° C., and more preferably is 60° C.

Cooling from a heating temperature to room temperature can be performed in a period between 5 min and 2 hours, and preferably in a period between 5 min and 1.5 hours.

10. Process for Preparing a Crystalline Form of the Ethanesulfonate (Form β)

(Preparation Method 1)

A crystalline form of the ethanesulfonate (Form β) can be prepared by adding a solvent and water to a crystalline form of the ethanesulfonate (Form α) and stirring the mixture at room temperature.

As a solvent, for example, methanol, ethanol, and 2-propanol can be used, and ethanol is preferable.

Although the amount of solvent is not particularly limited, preferably the amount used is 5- to 20-fold relative to the substrate amount, and more preferably 10-fold.

Although the amount of water is not particularly limited, a preferable amount is 1/10 to 1/2 of the ethanol amount, and more preferably 1/6 of the ethanol amount.

(Preparation Method 2)

A crystalline form of the ethanesulfonic (Form β) can be prepared by mixing the carboxamide, acetic acid and ethanesulfonic acid to dissolve the carboxamide.

More specifically, a crystalline form of the ethanesulfonate (Form β) can be prepared, for example, by mixing the carboxamide, acetic acid and ethanesulfonic acid, heating the mixture to dissolve the carboxamide, adding a poor solvent and water, and cooling this solution to 0° C. Preferably, seed crystals of a crystalline form of the ethanesulfonate (Form β) are added when the poor solvent is added.

Although the amount of acetic acid is not particularly limited, preferably the amount used is 2.5- to 10-fold relative to the substrate amount, and more preferably 5-fold.

The amount of ethanesulfonic acid used can be an equivalent of 1.0 to 1.5 relative to the substrate amount, and an equivalent of 1.2 is preferable.

As a poor solvent, for example, ethanol, and 2-propanol can be used, and 2-propanol is preferable.

Although the amount of poor solvent is not particularly limited, preferably the amount used is 10- to 40-fold relative to the substrate amount, and more preferably 30-fold. Further, the poor solvent can be added at on time or can be added dividedly 2 to 4 times, and preferably the poor solvent is divided and added 2 times. In this case, the ratio for the amount of solvent added the first time and the amount of solvent added the second time is from 1:1 to 1:5, and a ratio from 1:1.5 to 1.2 is preferable.

Although the amount of water is not particularly limited, a preferable amount is 1/10 to 1/30 of the poor solvent amount, and more preferably is 1/20 of the poor solvent amount.

Although a heating temperature is not particularly limited, a preferable temperature is between 50 and 70° C., and more preferably 60° C.

Cooling from a heating temperature to 0° C. can be performed in a period between 10 min and 6 hours, and preferably in a period between 2 and 4 hours.

11. Process for Preparing a Crystalline Form of the Dimethyl Sulfoxide Solvate of the Ethanesulfonate A crystalline form of the dimethyl sulfoxide solvate of the ethanesulfonate can be prepared by mixing the carboxamide, dimethyl sulfoxide and ethanesulfonic acid, heating the mixture to dissolve the carboxamide, adding a poor solvent, and cooling the mixture to 0° C. Preferably, seed crystals of a crystalline form of the ethanesulfonate (Form β) are added when the poor solvent is added.

Although the amount of dimethyl sulfoxide is not particularly limited, preferably the amount used is 5- to 20-fold relative to the substrate amount, and more preferably 10-fold.

The amount of ethanesulfonic acid used can be an equivalent of 1.0 to 1.5 relative to the substrate amount, and an equivalent of 1.2 is preferable.

As a poor solvent, for example, ethyl acetate can be used.

Although the amount of poor solvent is not particularly limited, preferably the amount used is 5- to 20-fold relative to the substrate amount, and more preferably 10-fold. Further, the poor solvent can be added at one time or can be added dividedly 2 to 4 times, and preferably the poor solvent is divided and added 2 times. In this case, the ratio for the amount of solvent added the first time and the amount of solvent added the second time if from 1:1 to 3:1, and a ratio of 3:2 is preferable.

Although a heating temperature is not particularly limited, a preferable temperature is between 50 and 70° C., and more preferably 60° C.

Cooling from a heating temperature to 0° C. can be performed in a period between 10 min and 6 hours, and preferably in a period between 1 and 2 hours.

When the crystals of the present invention are to be used as a medicament, it will normally be mixed with suitable additives for use as a formulation. However, the foregoing description does not limit the use of the crystals of the present invention as medicament in the state of intact products.

Such additives may include excipients, binders, lubricants, disintegrators, coloring agents, taste correctives, emulsifiers, surfactants, dissolving aids, suspending agents, isotonizing agents, buffering agents, antiseptics, antioxidants, stabilizers, absorption accelerators and the like which are commonly used in pharmaceuticals, and they may be added in appropriate combinations as desired.

As examples of such excipients there may be mentioned lactose, white soft sugar, glucose, corn starch, mannitol, sorbitol, starch, alpha starch, dextrin, crystalline cellulose, soft silicic anhydride, aluminum silicate, calcium silicate, magnesium aluminometasilicate, calcium hydrogenphosphate, and the like.

As examples of binders there may be mentioned polyvinyl alcohol, methylcellulose, ethylcellulose, gum Arabic, tragacanth, gelatin, shellac, hydroxypropylmethylcellulose, hydroxypropylcellulose, carboxymethylcellulose sodium, polyvinylpyrrolidone, macrogol, and the like.

As examples of lubricants there may be mentioned magnesium stearate, calcium stearate, sodium stearyl fumarate, talc, polyethylene glycol, colloidal silica, and the like.

As examples of disintegrators, there may be mentioned crystalline cellulose, agar, gelatin, calcium carbonate, sodium hydrogencarbonate, calcium citrate, dextrin, pectin, low-substituted hydroxypropylcellulose, carboxymethylcellulose, carboxymethylcellulose calcium, croscarmellose sodium, carboxymethyl starch, and carboxymethyl starch sodium, and the like.

As coloring agents there may be mentioned those approved for addition to pharmaceuticals, such as iron sesquioxide, yellow iron sesquioxide, carmine, caramel, β-carotene, titanium oxide, talc, riboflavin sodium phosphate, yellow aluminum lake and the like.

As taste correctives there may be mentioned cocoa powder, menthol, aromatic powders, mentha oil, borneol, powdered cinnamon bark, and the like.

As emulsifiers or surfactants there may be mentioned stearyl triethanolamine, sodium lauryl sulfate, lauryl aminopropionic acid, lecithin, glycerin monostearate, sucrose fatty acid esters, glycerin fatty acid esters, and the like.

As dissolving aids there may be mentioned polyethylene glycol, propylene glycol, benzyl benzoate, ethanol, cholesterol, triethanolamine, sodium carbonate, sodium citrate, polysorbate 80, nicotinamide, and the like.

As suspending agents there may be mentioned the surfactants referred to above, as well as hydrophilic polymers such as polyvinyl alcohol, polyvinylpyrrolidone, methylcellulose, hydroxymethylcellulose, hydroxyethylcellulose, hydroxypropylcellulose and the like.

As isotonizing agents there may be mentioned glucose, sodium chloride, mannitol, sorbitol and the like.

As buffering agents there may be mentioned buffering solutions of phosphate, acetate, carbonate, citrate and the like.

As antiseptics there may be mentioned methylparaben, propylparaben, chlororbutanol, benzyl alcohol, phenethyl alcohol, dehydroacetic acid, sorbic acid, and the like.

As antioxidants there may be mentioned sulfite, ascorbic acid, α-tocopherol, And the like.

The formulation may be in the form of an oral preparation such as a tablet, powder, granule, capsule, syrup, lozenge or inhalant; an external preparation such as a suppository, ointment, eye salve, tape, eye drop, nasal drop, ear drop, pap or lotion; or an injection.

An oral preparation will be formulated using an appropriate combination of additives among those mentioned above. The surface thereof may also be coated if necessary.

An external preparation will be formulated using an appropriate combination of additives among those mentioned above, and particularly excipients, binders, taste correctives, emulsifies, surfactants, dissolving aids, suspending agents, isotonizing agents, antiseptics, antioxidants, stabilizers and absorption accelerators.

An injection will be formulated using an appropriate combination of additives among those mentioned above, and particularly emulsifiers, surfactants, dissolving aids, suspending agents, isotonizing agents, buffering agents, antiseptics, antioxidants, stabilizers and absorption accelerators.

When the crystals of the invention is to be used as a medicament, the dosage thereof will differ depending on the symptoms and age of the patient as well as the form of administration, but it will ordinarily be 100 μg to 10 g per day, administered at once or divided over several times.

The crystals of the present invention are extremely useful as an angiogenesis inhibitor, and are also useful as a prophylactic or therapeutic agent for a disease for which angiogenesis inhibition is effective, an angiogenesis inhibitor, an anti-tumor agent, a therapeutic agent for angioma, a cancer metastasis inhibitor, a therapeutic agent for retinal neovascularization, a therapeutic agent for diabetic retinopathy, a therapeutic agent for an inflammatory disease, a therapeutic agent for an inflammatory disease selected from the group consisting of deformant arthritis, rheumatoid arthritis, psoriasis and delayed hypersensitivity reaction, and a therapeutic agent for atherosclerosis.

When using the crystals of the present invention as an anti-tumor agent, examples of the tumor include a pancreatic cancer, a gastric cancer, a colon cancer, a breast cancer, a prostrate cancer, a lung cancer, a renal cancer, a brain tumor, a blood cancer or an ovarian cancer, and in particular, a gastric cancer, a colon cancer, a prostrate cancer, a lung cancer or a renal cancer are preferable.

Further, the crystals of the present invention exhibit a strong inhibitory activity for c-Kit kinase, and are useful as an anti-cancer agent for a cancer which has undergone a malignant alteration due to activation of c-Kit kinase (for example, acute myelogenous leukemia, mast cell leukemia, a small cell lung cancer, GIST, a testicular tumor, an ovarian cancer, a breast cancer, a brain tumor, neuroblastoma or a colon cancer). The crystals of the present invention are also useful as a therapeutic agent for a disease such as mastocytosis, allergy or asthma that is considered to be caused by c-Kit kinase.

EXAMPLES

Hereunder, examples are described to facilitate further understanding of the present invention, however, the following examples are not intended to limit the scope of the present invention.

Preparation Example 1

Preparation of 4-(3-chloro-4-(cyclopropylaminocarbonyl)aminophenoxy)-7-methoxy-6-quinolinecarboxamide (1)

Phenyl N-(4-(6-carbamoyl-7-methoxy-4-quinolyl)oxy-2-chlorophenyl)carbamate (17.5 g, 37.7 mmol) disclosed in WO 02/32872 was dissolved in N,N-dimethylformamide (350 mL), and then cyclopropylamine (6.53 mL, 94.25 mmol) was added to the reaction mixture under a nitrogen atmosphere, followed by stirring overnight at room temperature. To the mixture was added water (1.75 L), and the mixture was stirred. Precipitated crude crystals were filtered off, washed with water, and dried at 70° C. for 50 min. To the obtained crude crystals was added ethanol (300 mL), and then the mixture was heated under reflux for 30 min to dissolve, followed by stirring overnight to cool slowly down to room temperature. Precipitated crystals was filtered off and dried under vacuum, and then further dried at 70° C. for 8 hours to give the titled crystals (12.91 g; 80.2%).

Preparation Example 2

Preparation of 4-(3-cloro-4-(cyclopropylaminocarbonyl)aminophenoxy)-7-methoxy-6-quinolinecarboxamide (2)

(1) Preparation of phenyl N-(2-chloro-4-hydroxyphenyl)carbamate

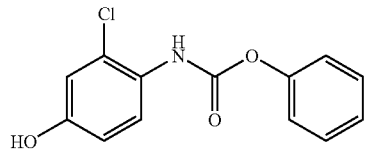

To a suspension of 4-amino-3-chlorophenol (23.7 g) in N,N-dimethylformamide (100 mL) was added pyridine (23.4 mL) while cooling in an ice bath, and phenyl chloroformate (23.2 mL) was added dropwise below 20° C. After stirring at room temperature for 30 min, water (400 mL), ethyl acetate (300 mL), and 6N-HCl (48 mL) were added and stirred. The organic layer was separated off, washed twice with a 10% aqueous sodium chloride solution (200 mL), and dried over magnesium sulfate. The solvent was evaporated to give 46 g of the titled compound as a solid.

$^1$H-NMR Spectrum (CDCl$_3$) δ(ppm): 5.12 (1H, br s), 6.75 (1H, dd, J=9.2, 2.8 Hz), 6.92 (1H, d, J=2.8 Hz), 7.18-7.28 (4H, m), 7.37-7.43 (2H, m), 7.94 (1H, br s).

(2) Preparation of 1-(2-chloro-4-hydroxyphenyl)-3-cyclopropylurea

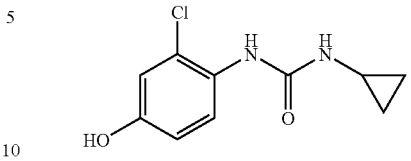

To a solution of phenyl N-(2-chloro-4-hydroxyphenyl)carbamate in N,N-dimethylformamide (100 mL) was added cyclopropylamine (22.7 mL) while cooling in an ice bath, and the stirring was continued at room temperature overnight. Water (400 mL), ethyl acetate (300 mL), and 6N-HCl (55 mL) were added thereto, and the mixture was stirred. The organic layer was then separated off, washed twice with a 10% aqueous sodium chloride solution (200 mL), and dried over magnesium sulfate. The solvent was evaporated to give prism crystals, which were filtered off and washed with heptane to give 22.8 g of the titled compound (yield from 4-amino-3-chlorophenol: 77%).

$^1$H-NMR Spectrum (CDCl$_3$) δ(ppm): 0.72-0.77 (2H, m), 0.87-0.95 (2H, m), 2.60-2.65 (1H, m), 4.89 (1H, br s), 5.60 (1H, br s), 6.71 (1H, dd, J=8.8, 2.8 Hz), 6.88 (1H, d, J=2.8 Hz), 7.24-7.30 (1H, br s), 7.90 (1H, d, J=8.8 Hz)

(3) Preparation of 4-(3-chloro-4-(cyclopropylaminocarbonyl)aminophenoxy)-7-methoxy-6-quinolinecarboxamide To dimethyl sulfoxide (20 mL) were added 7-methoxy-4-chloroquinoline-6-carboxamide (0.983 g), 1-(2-chloro-4-hydroxyphenyl)-3-cyclopropylurea (1.13 g) and cesium carbonate (2.71 g), and the mixture was heated and stirred at 70° C. for 23 hours. The reaction mixture was cooled to room temperature, and water (50 mL) was added, and the resultant crystals were then filtered off to give 1.56 g of the titled compound (yield: 88%).

Preparation Example 3

Preparation of 4-(3-chloro-4-(cyclopropylaminocarbonyl)aminophenoxy)-7-methoxy-6-quinolinecarboxamide (3)

7-Methoxy-4-chloroquinoline-6-carboxamide (5.00 kg, 21.13 mol), dimethyl sulfoxide (55.05 kg), 1-(2-chloro-4-hydroxyphenyl)-3-cyclopropylurea 5.75 kg, 25.35 mol) and potassium t-butoxide (2.85 kg, 25.35 mol) were introduced in this order into a reaction vessel under a nitrogen atmosphere. The mixture was stirred for 30 min at 20° C., and the temperature was raised to 65° C. over 2.5 hours. The mixture was stirred at the same temperature for 19 hours. 33% (v/v) acetone-water (5.0 L) and water (10.0 L) were added dropwise over 3.5 hours. After the addition was completed, the mixture was stirred at 60° C. for 2 hours. 33% (v/v) acetone-water (20.0 L) and water (40.0 L) were added dropwise at 55° C. or more over 1 hour. After stirring at 40° C. for 16 hours, precipitated crystals were filtered off using a nitrogen pressure filter, and was washed with 33% (v/v) acetone-water (33.3 L), water (66.7 L), and acetone (50.0 L) in that order. The obtained crystals were dried at 60° C. for 22 hours using a conical vacuum dryer to give 7.78 kg of the titled compound (yield: 96.3%).

$^1$H-NMR chemical, shift values for 4-(3-chloro-4-(cyclopropylaminocarbonyl)aminophenoxy)-7-methoxy-6-quinolinecarboxamides obtained in Preparation Examples 1 to 3 corresponded to those for 4-(3-chloro-4-(cyclopropylaminocarbonyl)aminophenoxy)-7-methoxy-6-quinolinecarboxamide disclosed in WO 02/32872.

Example 1

A Crystalline Form of the Hydrochloride of 4-(3-chloro-4-(cyclopropylaminocarbonyl)aminophenoxy)-7-methoxy-6-quinolinecarboxamide A suspension of 4-(3-chloro-4-(cyclopropylaminocarbonyl)aminophenoxy)-7-methoxy-6-quinolinecarboxamide (854 mg, 2.0 mmol) in ethanol (17 mL) was stirred, and 2 N hydrochloric acid (1.1 mL, 2.2 mmol) was added dropwise to the reaction mixture while refluxing using an oil bath with an external temperature of 100° C. After confirming that the suspension had changed into a solution, the heating of the oil bath was stopped, and the mixture was cooled slowly to room temperature while immersed in the oil bath, followed by stirring overnight. Ethanol (8.6 mL) was added to the reaction mixture, and resultant crystals were filtered off, washed with ethanol (4.3 mL×2), dried under aeration on filter paper (1.5 hours), and then dried (23 hours) with hot air at 70° C. to give the titled crystals (786.1 mg, 85%).

$^1$H-NMR. Spectrum (DMSO-$d_6$) δ(ppm): 0.30-0.50 (2H, m), 0.60-0.70 (2H, m), 2.56 (1H, m), 4.06 (3H, s), 6.86 (1H, d, J=6.4 Hz), 7.29-7.35 (2H, m), 7.60 (1H, d, J=2.8 Hz), 7.64 (1H, s), 7.88 (1H, s), 7.95 (1H, s), 8.07 (1H, s), 8.34 (1H, d, J=9.2 Hz), 8.70 (1H, s), 8.91 (1H, d, J=6.4 Hz).

Example 2

A Crystalline Form of the Hydrobromide of 4-(3-chloro-4-(cyclopropylaminocarbonyl)aminophenoxy)-7-methoxy-6-quinolinecarboxamide A suspension of 4-(3-chloro-4-(cyclopropylaminocarbonyl)aminophenoxy)-7-methoxy-6-quinolinecarboxamide (500 mg, 1.17 mmol) in ethanol (10 mL) was stirred, and an aqueous solution of 1 N hydrobromic acid (1.3 mL, 1.3 mmol) was then added dropwise to the reaction mixture while refluxing using an oil bath with an external temperature of 100° C. After water (2.0 mL) was gradually added to the mixture to form a solution, the heating of the oil bath was stopped, and the mixture was cooled slowly to room temperature while immersed in the oil bath, followed by stirring overnight. Precipitated crystals were filtered off, washed with ethanol (2.5 mL×2), dried under aeration on filter paper (15 min), and then dried (22 hours) with hot air at 100° C. to give the titled crystals (483.7 mg, 81%).

$^1$H-NMR Spectrum (DMSO-$d_6$) δ(ppm): 0.40-0.50 (2H, m), 0.60-0.70 (2H, m), 2.58 (1H, m), 4.09 (3H, s), 6.89 (1H, d, J=6.4 Hz), 7.26 (1H, d, J=2.8 Hz), 7.33 (1H, dd, J=2.8, 9.2 Hz), 7.59 (1H, s), 7.62 (1H, d, J=2.8 Hz), 7.90 (1H, s), 7.96 (1H, s), 8.06 (1H, s), 8.36 (1H, d, J=9.2 Hz), 8.72 (1H, s), 8.93 (1H, d, J=6.4 Hz).

Example 3

A Crystalline Form of the p-toluenesulfonate of 4-(3-chloro-4-(cyclopropylaminocarbonyl)aminophenoxy)-7-methoxy-6-quinolinecarboxamide Dimethyl sulfoxide (1.5 mL) and p-toluenesulfonic acid monohydrate (80 mg, 0.422 mmol) were added to 4-(3-chloro-4-(cyclopropylaminocarbonyl)aminophenoxy)-7-methoxy-6-quinolinecarboxamide (150 mg, 0.351 mmol) at room temperature. Although a solution was temporarily formed, crystals precipitated immediately. Therefore, dimethyl sulfoxide (2.25 mL) was added to the reaction mixture at 80° C. to dissolve the crystals. The mixture was cooled slowly to room temperature, and stirred for 14 hours. Precipitated crystals were filtered off and dried at 60° C. to give the titled crystals (177 mg).

$^1$H-NMR Spectrum (400 MHz, DMSO-$d_6$) δ(ppm): 0.39 (2H, m), 0.63 (2H, m), 2.24 (3H, s), 2.54 (1H, m), 4.04 (3H, s), 6.88 (1H, d, J=6.4 Hz), 7.05 (1H, s), 7.07 (1H, s), 7.21 (1H, d, J=2.8 Hz), 7.31 (1H, dd, J=2.6, 9.3 Hz), 7.41 (1H, s), 7.43 (1H, s), 7.59 (1H, d, J=2.8 Hz), 7.86 (1H, s), 7.92 (1H, s), 8.02 (1H, s), 8.32 (1H, d, J=9.6 Hz), 8.68 (1H, s), 8.91 (1H, d, J=6.4 Hz)

Example 4

A Crystalline Form of the Sulfate of 4-(3-chloro-4-(cyclopropylaminocarbonyl)aminophenoxy)-7-methoxy-6-quinolinecarboxamide Dimethyl sulfoxide (1.5 mL) and sulfuric acid (23 μL, 0.422 mmol) were added to 4-(3-chloro-4-(cyclopropylaminocarbonyl)aminophenoxy)-7-methoxy-6-quinolinecarboxamide (150 mg, 0.351 mmol) at room temperature. Although a solution was temporarily formed, crystals precipitated immediately. Therefore, dimethyl sulfoxide (2.25 mL) was added to the reaction mixture at 80° C. to dissolve the crystals. The mixture was cooled slowly to room temperature, and stirred for 16 hours. Precipitated crystals were filtered off and dried at 60° C. to give the titled crystals (174 mg).

$^1$H-NMR Spectrum (400 MHz, DMSO-$d_6$) δ(ppm): 0.39 (2H, m), 0.63 (2H, m), 2.46 (2H, d, J=1.2 Hz), 2.52 (1H, m), 4.04 (3H, s), 6.88 (1H, d, J=5.8 Hz), 7.21 (1H, s), 7.31 (1H, d, J=8.2 Hz), 7.56 (1H, s), 7.59 (1H, s), 7.86 (1H, s), 7.93 (1H, s), 8.02 (1H, s), 8.33 (1H, d, J=8.2 Hz), 8.68 (1H, s), 8.91 (1H, d, J=5.8 Hz)

Example 5

A Crystalline Form of the Methanesulfonate of 4-(3-chloro-4-(cyclopropylaminocarbonyl)aminophenoxy)-7-methoxy-6-quinolinecarboxamide (Form A)

(Preparation Method 1)

In a mixed solution of methanol (14 mL) and methanesulfonic acid (143 μL, 1.97 mmol) was dissolved 4-(3-chloro-4-(cyclopropylaminocarbonyl)aminophenoxy)-7-methoxy-6-quinolinecarboxamide (700 mg, 1.64 mmol) at 70° C. After confirming the dissolution of 4-(3-chloro-4-(cyclopropylaminocarbonyl)aminophenoxy)-7-methoxy-6-quinolinecarboxamide, the reaction mixture was cooled to room temperature over 5.5 hours, further stirred at room temperature for 18.5 hours, and crystals were filtered off. The resultant crystals were dried at 60° C. to give the titled crystals (647 mg).

(Preparation Method 2)

In a mixed solution of acetic acid (6 mL) and methanesulfonic acid (200 μL, 3.08 mmol) was dissolved 4-(3-chloro-4-(cyclopropylaminocarbonyl)aminophenoxy)-7-methoxy-6-quinolinecarboxamide (600 mg, 1.41 mmol) at 50° C. After confirming the dissolution of 4-(3-chloro-4-(cyclopropylaminocarbonyl)aminophenoxy)-7-methoxy-6-quinolinecarboxamide, ethanol (7.2 mL) and seed crystals of a crystalline form of the methanesulfonate of 4-(3-chloro-4-

(cyclopropylaminocarbonyl)aminophenoxy)-7-methoxy-6-quinolinecarboxamide (Form A) (12 mg) were added in this order to the reaction mixture, and ethanol (4.8 mL) was further added dropwise over 2 hours. After the addition was completed, the reaction mixture was stirred at 40° C. for 1 hour then at room temperature for 9 hours, and crystals were filtered off. The resultant crystals were dried at 60° C. to give the titled crystals (545 mg).

Example 6

A Crystalline Form of the Methanesulfonate of 4-(3-chloro-4-(cyclopropylaminocarbonyl)aminophenoxy)-7-methoxy-6-quinolinecarboxamide (Form B)

A crystalline form of the acetic acid solvate of the methanesulfonate of 4-(3-chloro-4-(cyclopropylaminocarbonyl)aminophenoxy)-7-methoxy-6-quinolinecarboxamide (Form I) (250 mg) obtained in Example 10 was dried under aeration at 30° C. for 3 hours and at 40° C. for 16 hours to give the titled crystals (240 mg).

Example 7

A Crystalline Form of the Methanesulfonate of 4-(3-chloro-4-(cyclopropylaminocarbonyl)aminophenoxy)-7-methoxy-6-quinolinecarboxamide (Form C)

(Preparation Method 1)

n-butyl acetate (12 mL) was added to a crystalline form of the dimethyl sulfoxide solvate of the methanesulfonate of 4-(3-chloro-4-(cyclopropylaminocarbonyl)aminophenoxy)-7-methoxy-6-quinolinecarboxamide (600 mg, 1.15 mmol) obtained in Example 8 (Preparation Method 1), and the reaction mixture was stirred at 115° C. for 10 hours and further stirred at room temperature for 1.5 hours Resultant crystals were then filtered off and dried at 60° C. to give the titled crystals (503 mg).

(Preparation Method 2)

Ethanol (6.4 mL) was added to a crystalline form of the acetic acid solvate of the methanesulfonate of 4-(3-chloro-4-(cyclopropylaminocarbonyl)aminophenoxy)-7-methoxy-6-quinolinecarboxamide (Form I) (1.28 g) obtained in Example 10 to dissolve at 40° C., and then the reaction mixture was stirred at the same temperature for 36 hours. Precipitated crystals were filtered off and dried at 50° C. to give the titled crystals (0.87 g).

(Preparation Method 3)

To a mixed solution of acetic acid (14 mL) and methanesulfonic acid (0.37 mL, 5.62 mmol) 4-(3-chloro-4-(cyclopropylaminocarbonyl)aminophenoxy)-7-methoxy-6-quinolinecarboxamide (2.00 g, 4.69 mmol) was added to dissolve at 40° C. After confirming the dissolution, 2-propanol (9 mL) and seed crystals of a crystalline form of the methanesulfonate of 4-(3-chloro-4-(cyclopropylaminocarbonyl)aminophenoxy)-7-methoxy-6-quinolinecarboxamide (Form C) (100 mg) were added in this order to the reaction mixture, and the reaction mixture was stirred for 20 min. Isopropyl acetate (10 mL) was then further added dropwise over 30 min. After the addition of the isopropyl acetate was completed, the reaction mixture was stirred for 1.5 hours, and further stirred at 15° C. for 14 hours. Precipitated crystals were filtered off and dried at 60° C. to give the titled crystals (2.22 g).

(Preparation Method 4)

To a suspension of 4-(3-chloro-4-(cyclopropylaminocarbonyl)aminophenoxy)-7-methoxy-6-quinolinecarboxamide (1.28 g, 3 mmol) in acetic acid (12.8 ml) was added methanesulfonic acid (0.408 ml, 6.3 mmol), and the mixture was stirred at room temperature to dissolve. The reaction mixture was heated with a bath at a temperature of 30° C., and 2-propanol (7.7 ml) was added. Seed crystals of a crystalline form of the methanesulfonate of 4-(3-chloro-4-(cyclopropylaminocarbonyl)aminophenoxy)-7-methoxy-6-quinolinecarboxamide (Form C) was added, and 2-propanol was further added 14 times by every amount of 1.28 ml over 44 min. The warm bath was removed, the reaction mixture was stirred for 10 min at room temperature, then for 5 min in a water bath, and for 25 min in a water bath with a small amount of ice (internal temperature: 17.6° C.). Resultant crystals were filtered off and washed with 2-propanol (10 ml). The filtered crystals were stirred in ethanol (6.4 ml) at room temperature for 1 hour. Resultant crystals were filtered off, washed with ethanol (4 ml) and dried at 60° C. to give the titled crystals (1068 mg).

Example 8

A Crystalline Form of the Dimethyl Sulfoxide Solvate of Methanesulfonate of 4-(3-chloro-4-(cyclopropylaminocarbonyl)aminophenoxy)-7-methoxy-6-quinolinecarboxamide (Preparation Method 1)

Dimethyl sulfoxide (7 mL) was added at room temperature to 4-(3-chloro-4-(cyclopropylaminocarbonyl)aminophenoxy)-7-methoxy-6-quinolinecarboxamide (700 mg, 1.640 mmol) and the mixture was dissolved at 80° C. Methanesulfonic acid (143 µL, 1.97 mmol), ethyl acetate (1.4 mL), and seed crystals of a crystalline form of the methanesulfonate of 4-(3-chloro-4-(cyclopropylaminocarbonyl)aminophenoxy)-7-methoxy-6-quinolinecarboxamide (Form A) were added in this order to the reaction mixture at 60° C., and ethyl acetate (5.6 mL) was further added dropwise over 45 min. 15 min after completion of the addition of the ethyl acetate, the reaction mixture was cooled to room temperature over 1 hour, and stirred at the same temperature for 18 hours. Precipitated crystals were filtered off and dried at 60° C. to give the titled crystals (746 mg).

(Preparation Method 2)

Dimethyl sulfoxide (6.8 mL) was added at room temperature to 4-(3-chloro-4-(cyclopropylaminocarbonyl)aminophenoxy)-7-methoxy-6-quinolinecarboxamide (854 mg, 2 mmol) and the mixture was dissolved at 60° C. Methanesulfonic acid (389 µL, 6 mmol) and seed crystals of a crystalline form of the methanesulfonate of 4-(3-chloro-4-(cyclopropylaminocarbonyl)aminophenoxy)-7-methoxy-6-quinolinecarboxamide (Form A) were added in this order to the reaction mixture at the same temperature, and 2-propanol (6.8 mL) was then added dropwise over 30 min. After completion of the addition of the 2-propanol, the reaction mixture was cooled to 15° C. over 2 hours, and then stirred at the same temperature for 30 min. Precipitated crystals were filtered off and dried at 60° C. to give the titled crystals (1095 mg).

(Preparation Method 3)

Dimethyl sulfoxide (6.8 mL) was added at room temperature to 4-(3-chloro-4-(cyclopropylaminocarbonyl)aminophenoxy)-7-methoxy-6-quinolinecarboxamide (854 mg, 2 mmol) and the mixture was dissolved at 62° C. Methanesulfonic acid (454 μL, 7 mmol) and seed crystals of a crystalline form of the methanesulfonate of 4-(3-chloro-4-(cyclopropylaminocarbonyl)aminophenoxy)-7-methoxy-6-quinolinecarboxamide (Form A) were added in this order to the reaction mixture at the same temperature, and 2-propanol (13.6 mL) was then added dropwise over 1 hour. After the completion of the addition of the 2-propanol, the reaction mixture was cooled to 15° C. over 2 hours, and then stirred at the same temperature for 30 min. Precipitated crystals were filtered off and dried at 60° C. to obtain the titled crystal (1082 mg).

Example 9

A Crystalline Form of the Hydrate of the Methanesulfonate of 4-(3-chloro-4-(cyclopropylaminocarbonyl)aminophenoxy)-7-methoxy-6-quinolinecarboxamide (Form F)

In a mixed solution of acetic acid (1.5 mL) and methanesulfonic acid (31 μL, 0.422 mmol) was dissolved 4-(3-chloro-4-(cyclopropylaminocarbonyl)aminophenoxy)-7-methoxy-6-quinolinecarboxamide (150 mg, 0.351 mmol) at 50° C. After confirming the dissolution, ethyl acetate (0.6 mL) and a crystalline form of the methanesulfonate of 4-(3-chloro-4-(cyclopropylaminocarbonyl)aminophenoxy)-7-methoxy-6-quinolinecarboxamide (Form A) obtained in Example 5 (Preparation method 1) were added In this order to the reaction mixture, and ethyl acetate (1.8 mL) was further added dropwise over 2 hours. After the addition of ethyl acetate was completed, the reaction mixture was stirred at 50° C. for 30 min, and then stirred at room temperature for 7.5 hours. Precipitated crystals were filtered off and dried at 60° C. to give the titled crystals (176 mg).

Example 10

A Crystalline Form of the Acetic Acid Solvate of the Methanesulfonate of 4-(3-chloro-4-(cyclopropylaminocarbonyl)aminophenoxy)-7-methoxy-6-quinolinecarboxamide (Form I)

In a mixed solution of acetic acid (14 mL) and methanesulfonic acid (0.36 mL, 5.62 mmol) was dissolved 4-(3-chloro-4-(cyclopropylaminocarbonyl)aminophenoxy)-7-methoxy-6-quinolinecarboxamide (2.00 g, 4.69 mmol) at 40° C. After confirming the dissolution, 1-propanol (4 mL) and seed crystals of a crystalline form of the methanesulfonate of 4-(3-chloro-4-(cyclopropylaminocarbonyl)aminophenoxy)-7-methoxy-6-quinolinecarboxamide (Form C) (100 mg) were added in this order to the reaction mixture, and 1-propanol (14 mL) and isopropyl acetate (10 mL) were further added dropwise over 1 hour. After the addition was completed, the reaction mixture was stirred at 40° C. for 1 hour, and then stirred at 25° C. for a further 40 min. Precipitated crystals were filtered off to give the titled crystals (2.61 g).

The $^1$H-NMR chemical shift values for the methanesulfonate are as follows:

$^1$H-NMR Spectrum (DMSO-$d_6$) δ(ppm): 0.44 (2H, m), 0.67 (2H, m), 2.36 (3H, s), 2.59 (1H, m), 4.09 (3H, s), 6.95 (1H, d, J=7 Hz), 7.25 (1H, d, J=2 Hz), 7.36 (1H, dd, J=3, 9 Hz), 7.63 (1H, d, J=3 Hz), 7.65 (1H, s), 7.88 (1H, brs), 7.95 (1H, brs), 8.06 (1H, s), 8.37 (1H, d, J=9 Hz), 8.73 (1H, s), 8.97 (1H, d, J=7 Hz)

Example 11

A Crystalline Form of the Ethanesulfonate of 4-(3-chloro-4-(cyclopropylaminocarbonyl)aminophenoxy)-7-methoxy-6-quinolinecarboxamide (Form α)

(Preparation Method 1)

Dimethyl sulfoxide (1.5 mL) and ethanesulfonic acid (34 μL, 0.422 mmol) were added to 4-(3-chloro-4-(cyclopropylaminocarbonyl)aminophenoxy)-7-methoxy-6-quinolinecarboxamide (150 mg, 0.351 mmol) and the mixture was dissolved at room temperature. Ethyl acetate (1.5 mL) was added dropwise to the reaction mixture at 60° C. over 1.5 hours. 30 min after the addition of ethyl acetate was completed, the reaction mixture was cooled to room temperature over 1.5 hours, and then stirred at room temperature for a further 7 hours. Precipitated crystals were filtered off and dried at 60° C. to give the titled crystals (176 mg).

(Preparation Method 2)

Ethanol (40 mL) and ethanesulfonic acid (459 μL, 5.622 mmol) were added to 4-(3-chloro-4-(cyclopropylaminocarbonyl)aminophenoxy)-7-methoxy-6-quinolinecarboxamide (150 mg, 0.351 mmol) at room temperature and the mixture was dissolved at 65° C. The reaction mixture was cooled with a bath at a temperature of 22° C., and seed crystals of a crystalline form of the ethanesulfonate of 4-(3-chloro-4-(cyclopropylaminocarbonyl)aminophenoxy)-7-methoxy-6-quinolinecarboxamide (Form α) was added. The mixture was stirred for further 7 hours. Precipitated crystals were filtered off and dried at 70° C. to give the titled crystals (1.55 g).

Example 12

A Crystalline Form of the Ethanesulfonate of 4-(3-chloro-4-(cyclopropylaminocarbonyl)aminophenoxy)-7-methoxy-6-quinolinecarboxamide (Form β)

(Preparation Method 1)

Ethanol (3 mL) and water (0.5 mL) were added to a crystalline form of the ethanesulfonate of 4-(3-chloro-4-(cyclopropylaminocarbonyl)aminophenoxy)-7-methoxy-6-quinolinecarboxamide (Form α) (198 mg) obtained in Example 11, and the reaction mixture was stirred at room temperature for 3 hours. Crystals were filtered off and dried at 60° C. to give the titled crystals (89 mg).

(Preparation Method 2)

Acetic acid (0.75 mL) and ethanesulfonic acid (34 μL, 0.422 mmol) were added at room temperature to 4-(3-chloro-4-(cyclopropylaminocarbonyl)aminophenoxy)-7-methoxy-6-quinolinecarboxamide (150 mg, 0.351 mmol), and the mixture was then dissolved at 60° C. To the reaction mixture were added water (0.225 mL), 2-propanol (2 mL), a crystalline form of the ethanesulfonate of 4-(3-chloro-4-(cyclopropylaminocarbonyl)aminophenoxy)-7-methoxy-6-quinolinecarboxamide (Form β) obtained in (Preparation method 1) of Example 12, and 2-propanol (2.5 mL) in this order, and the mixture was then cooled to 0° C. over 2.5 hours, and stirred for 30 min. Precipitated crystals were filtered off and dried at 60° C. to give the titled crystals (139 mg).

Example 13

A Crystalline Form of the Dimethyl Sulfoxide Solvate of the Ethanesulfonate of 4-(3-chloro-4-(cyclopropylaminocarbonyl)aminophenoxy)-7-methoxy-6-quinolinecarboxamide Dimethyl sulfoxide (4 mL) was added at room temperature to 4-(3-chloro-4-(cyclopropylaminocarbonyl)aminophenoxy)-7-methoxy-6-quinolinecarboxamide (400 mg, 0.937 mmol), and the mixture was then dissolved at 60° C. To the reaction mixture were added ethanesulfonic acid (92 µL, 1.124 mmol), ethyl acetate (2.4 mL) and a crystalline form of the ethanesulfonate of 4-(3-chloro-4-(cyclopropylaminocarbonyl)aminophenoxy)-7-methoxy-6-quinolinecarboxamide (Form β) obtained in (Preparation Method 1) of Example 12 in this order, and the mixture was then stirred at 60° C. for 20 min. After a further addition of ethyl acetate (1.6 mL), the reaction mixture was once heated to 80° C., and then cooled to 0° C. over 1.5 hours. Precipitated crystals were filtered off and dried at 60° C. to give the titled crystals (523 mg).

The $^1$H-NMR chemical shift values for the ethanesulfonate are as follows:

$^1$H-NMR Spectrum (DMSO-$d_6$) δ(ppm): 0.43 (2H, m), 0.66 (2H, m), 1.05 (3H, t, J=7.4 Hz), 2.38 (2H, q, J=7.4 Hz), 2.58 (1H, m), 4.08 (3H, s), 6.88 (1H, s), 7.24 (1H, s), 7.34 (1H, d, J=9.0 Hz), 7.60 (1H, s), 7.61 (1H, s), 7.88 (1H, s), 7.94 (1H, s), 8.05 (1H, s), 8.36 (1H, d, J=9.01 Hz), 8.72 (1H, s), 8.92 (1H, s)

Test Example 1

Test for Measuring Dissolution Rate

[Method]
The dissolution rates of the following crystals were measured under the conditions described below by the rotating disk method (see, J. H. Woods et al., J. Pharm. Soc., 54, 1068 (1955)): a crystalline form of the free carboxamide (obtained in Preparation Example 1), a crystalline form of the hydrochloride of the carboxamide (obtained in Example 1), a crystalline form of the hydrobromide of the carboxamide (obtained in Example 2), a crystalline form of the methanesulfonate (hereunder, referred to as "mesylate") of the carboxamide (Form A) (obtained in Example 5), a crystalline form of the mesylate of the carboxamide (Form C) (obtained in Example 7) and a crystalline form of the ethanesulfonate (hereunder, referred to as "esylate") (Form β) (obtained in Example 12). The dissolution rates were calculated based on a range in which linearity was maintained in the relation between concentration and time at the initial stage of dissolution.

(Rotating Disk Method Conditions)
Solvent: "2nd fluid" (pH 6.8, 500 mL) as described in Japanese Pharmacopoeia 14th Edition, General Tests (disintegration test)
Temperature: 37° C.
Disk rotation speed: 50 rpm
Area of powder contacting with solvent on disk: 1 cm$^2$
Sampling amount: approx. 1 mL (HPLC Conditions)
Column: Cadenza CD-18 (Imtakt Corporation; inner diameter 4.6 mm, Column length 100 mm, particle size 3 µm)
Column temperature: 40° C.
Flow rate: 1.0 mL/min
Mobile phase:
    Solution A: $H_2O:CH_3CN:HClO_4$=990:10:1 (v/v/v)
    Solution B: $CH_3CN:H_2O:HClO_4$=900:100:1 (v/v/v)
    Concentration of solution B: 20%
Injection amount: 100 µL
Detection: ultraviolet absorbance photometer (wavelength: 252 nm)
Temperature of auto sampler: 25° C.

[Results]
Table 1 shows the dissolution rates.

TABLE 1

|  | dissolution rate (µg/min/cm$^2$) |
|---|---|
| free form | 0.8 |
| hydrochloride | 4.7 |
| hydrobromide | 8.7 |
| mesylate (Form A) | 11.8 |
| mesylate (Form C) | 15.5 |
| esylate (Form β) | 18.5 |

For each crystal of the salts, the dissolution rate increased significantly in comparison to a crystalline form of the free form of the carboxamide. The increase of dissolution rate was particularly remarkable for a crystalline form of the mesylate and a crystalline form of the esylate.

Test Example 2

Study of Pharmacokinetics in Beagle Dogs

[Method]
A crystalline form of the free from of the carboxamide (obtained in Preparation Example 1), a crystalline form of the hydrobromide of the carboxamide (obtained in Example 2) and a crystalline form of the mesylate of the carboxamide (Form A) (obtained in Example 5) were grounded in a mortar, encapsulated in a gelatin capsule, and then administered orally to beagle dogs (n=3). After administration, 10 mL of water was further administered orally. The dose was set such that it was equivalent to 3 mg/kg as a free form, and the beagle dogs were fasted from the day before administration, and fed again 8 hours after the administration.

To calculate bioavailability (BA), a test was conducted using a single intravenous administration. More specifically, a crystalline form of the free from of the carboxamide was dissolved in a solution containing 10% dimethyl sulfoxide, 50% polyethylene glycol 400 and 40% 0.1 M aqueous solution of hydrochloric acid and administered intravenously through cephalic vein of the foreleg.

The plasma concentration of the carboxamide was measured by HPLC-UV method after sampling blood from cephalic vein of the foreleg. Based on the concentration, pharmacokinetic parameters were calculated for each individual by the moment method. Further, based on the calculated parameters, the mean value and standard error thereof were calculated.

[Results]
Table 2 shows the pharmacokinetic parameters, and FIG. 1 shows the relation between time and plasma concentration.

TABLE 2

|  | | free form | hydrobromide | mesylate (Form A) |
|---|---|---|---|---|
| time to reach maximum plasma concentration ($T_{max}$) | (hr) | 1.17 ± 0.4 | 2.67 ± 0.7 | 1.67 ± 0.3 |
| Maximum plasma concentration ($C_{max}$) | (ng/mL) | 53.3 ± 9.9 | 480.4 ± 31.4 | 397.1 ± 100.1 |
| plasma concentration after 24 hours ($C_{24hr}$) | (ng/mL) | 24.0 ± 9.0 | 100.5 ± 81.7 | 17.1 ± 2.5 |
| $AUC_{0-24hr}$ | (μg hr/mL) | 0.6 ± 0.0 | 4.8 ± 0.2 | 3.0 ± 0.4 |
| BA | (%) | 9.1 ± 0.4 | 73.5 ± 2.3 | 46.2 ± 5.9 |

The maximum plasma concentration and BA increased significantly for each crystalline form of the salts in comparison to a crystalline form of the free form.

Test Example 3

Evaluation of Hygroscopicity and Solid Stability

[Method]

The hygroscopicity and solid stability of a crystalline form of the mesylate of the carboxamide (Form A) (obtained in Example 5), a crystalline form of the mesylate of the carboxamide (Form C) (obtained in Example 7), a crystalline form of the acetic acid solvate of the mesylate of the carboxamide (Form I) (obtained in Example 10) and a crystalline form of the esylate of the carboxamide (Form β) (obtained in Example 12) were measured under the following conditions.

1. Storage Conditions for the Hygroscopicity Test (Period: 1 Week)
   a-1. 25° C., relative humidity 75%
   b-1. 25° C., relative humidity 93%

2. Storage Conditions for the Solid Stability Test (Period: 2 Weeks)
   a-2. −20° C. (well closed)
   b-2. 25° C., light irradiation (1000 1x; shading with aluminum foil, well closed)
   c-2. 25° C., light irradiation (1000 1x; well closed)
   d-2. 40° C., relative humidity 75%
   e-2. 60° C. (well closed except the following case: slightly open in the case of a crystalline form of the acetic acid solvate of the mesylate (Form I))

3. Method for Measuring the Impurity Amount by HPLC

After storage, the sample solution was prepared by adding a mixed solvent of water and methanol (3:1) to each crystal at 0.1 mg/mL as final concentration.

Tests were conducted by the HPLC method for these sample solutions under the measurement conditions described below, and the eluted peak areas were measured to determine the total impurity amount by the relative area method (impurities of 0.05% or more were counted).

(Formula for Calculating Total Impurity Amount)

Individual impurity amount (%)=(the peak area for the individual impurity)×100/{(the peak area for carboxamide)+(sum of the peak areas for impurities)}

Total impurity amount (%)=sum of individual impurity amounts (HPLC Measurement Conditions)

Column: Mightysil RP-18 GP (Kanto Kagaku; inner diameter 4.6 mm, column length 150 mm, particle size 3 μm)

Column temperature: constant temperature in vicinity of 40° C.

Flow rate: 1.0 mL/min

Mobile phase:
  Solution A: $H_2O:CH_3CN:HClO_4$=990:10:1 (v/v/v)
  Solution B: $CH_3CN:H_2O:HClO_4$=900:100:1 (v/v/v)

Gradient conditions

TABLE 3

| time (min) | concentration of Solution B (%) |
|---|---|
| 0 | 5 |
| 3 | 20 |
| 15 | 20 |
| 30 | 100 |
| 30.01 | 5 |
| 35 | 5 |

Injection amount: 10 μL

Detection: ultraviolet absorbance photometer (wavelength: 252 nm)

Temperature of auto sampler: constant temperature in vicinity of 10° C.

4. Powder X-ray Diffraction

Analysis was carried out according to "X-Ray Powder Diffraction Method" described in Japanese Pharmacopoeia 14th Edition, General Tests (B-614 to 619) under the following measurement conditions.

Apparatus: RINT-2000 (manufacture by Rigaku Denki K. K.)
X-ray: CuKα ray
Monochrometer: curved crystal monochrometer
Goniometer: vertical goniometer
Counter: scintillation counter
Applied voltage: 40 kV
Charging current: 200 mA
Scan speed: 5°/min
Scan axis: 2θ/θ
Scan range; 2θ+5° to 40°
Divergent slit: 0.5°
Scattering slit: 0.5°
Receiving slit: 0.3 mm 5. Measurement of Water Content Measurement was carried out according to the Water Determination as described in Japanese Pharmacopoeia 14th Edition, General Tests (B-318 to 331) using 6 to 10 mg of each crystal.

[Results]

The results of hygroscopicity evaluation are shown in Table 4 to Table 7.

TABLE 4

Evaluation of hygroscopicity of a crystalline form of the mesylate (Form A)

| condition | water content (%) | crystal form |
|---|---|---|
| initial | 0.7 | C |
| a-1 | 0.6 | C |
| b-1 | 0.7 | C |

TABLE 5

Evaluation of hygroscopicity of a crystalline form of the mesylate (Form C)

| condition | water content (%) | crystal form |
|---|---|---|
| initial | 0.7 | C |
| a-1 | 0.6 | C |
| b-1 | 0.7 | C |

TABLE 6

Evaluation of hygroscopicity of a crystalline form of the acetic acid solvate of the mesylate (Form I)

| condition | water content (%) | crystal form |
|---|---|---|
| initial | 2.9 | I |
| a-1 | 0.6 | C |
| b-1 | 0.8 | C |

TABLE 7

Evaluation of hygroscopicity of a crystalline form of the esylate (Form β)

| condition | water content (%) | crystal form |
|---|---|---|
| initial | 1.7 | β |
| a-1 | 1.7 | β |
| b-1 | 1.4 | β |

Water content did not change remarkably for a crystalline form of the mesylate (Form A), a crystalline form of the mesylate (Form C) and a crystalline form of the esylate (Form β), and hygroscopicity was not observed. Neither remarkable change in appearance nor crystal transition was observed.

In contrast, with regard to a crystalline form of the acetic acid solvate of the mesylate (Form I), a decrease in water content was observed as well as transition to a crystalline form of the mesylate (Form C).

The results of evaluation of solid stability are shown in Table 8 to Table 11.

TABLE 8

Evaluation of solid stability of a crystalline form of the mesylate (Form A)

| condition | total impurity (%) | water content (%) | crystal form |
|---|---|---|---|
| initial | 4.02 | 0.3 | A |
| a-2 | 3.90 | 0.0 | A |
| b-2 | 3.95 | 0.0 | A |
| c-2 | 4.23 | 0.1 | A |
| d-2 | 3.90 | 0.2 | A |
| e-2 | 3.97 | 0.2 | A |

TABLE 9

Evaluation of solid stability of a crystalline form of the mesylate (Form C)

| condition | total impurity (%) | water content (%) | crystal form |
|---|---|---|---|
| initial | 2.11 | 0.7 | C |
| a-2 | 2.10 | 0.7 | C |
| b-2 | 2.09 | 0.8 | C |
| c-2 | 2.22 | 0.7 | C |
| d-2 | 2.06 | 0.6 | C |
| e-2 | 2.18 | 0.5 | C |

TABLE 10

Evaluation of solid stability of a crystalline form of the acetic acid solvate of the mesylate (Form I)

| condition | total impurity (%) | water content (%) | crystal form |
|---|---|---|---|
| initial | 0.62 | 2.9 | I |
| a-2 | 0.67 | 3.1 | I |
| b-2 | 0.66 | 3.1 | I |
| c-2 | 0.87 | 2.9 | I |
| d-2 | 0.61 | 0.9 | C |
| e-2 | 0.84 | 0.3 | B |

TABLE 11

Evaluation of solid stability of a crystalline form of the esylate (Form β)

| condition | total impurity (%) | water content (%) | crystal form |
|---|---|---|---|
| initial | 0.55 | 1.7 | β |
| a-2 | 0.48 | 2.0 | β |
| b-2 | 0.46 | 2.5 | β |
| c-2 | 0.49 | 2.1 | β |
| d-2 | 0.48 | 2.0 | β |
| e-2 | 0.51 | 2.2 | β |

For a crystalline form of the mesylate (Form A), a crystalline form of the mesylate (Form C) and a crystalline form of the esylate (Form β), neither remarkable changes in water content and appearance nor crystal transition was observed.

In contrast, with regard to a crystalline form of the mesylate (Form I), neither crystal transition nor remarkable changes in total impurity amount, water content and appearance were observed when stored in a well closed container. However, for a sample stored under conditions of 40° c. and relative humidity of 75%, a decrease in water content was observed along with transition to a crystalline form of the mesylate (Form C). Further, for a sample stored at 60° c. in a slightly opened container, a decrease in water content was observed along with transition to a crystalline form of the mesylate (Form B).

Test Example 4

Powder X-ray Diffraction of a Crystalline Form of the Mesylate (Form B) (Obtained in Example 6) with a Treatment of Humidification

[Method]

Powder X-ray diffraction was measured under the measurement conditions similar to those in 4. (powder X-ray diffraction) of Test Example 3. Humidification was carried out using a humidity control unit HUM-1A (manufactured by Rigaku Denki K. K.)), to sequentially adjust relative humidity to 3%, 30%, 50%, 60%, 70%, 75%, 80% and 85% at room temperature.

[Results]

A crystalline form of the mesylate (Form B) remained its state and did not exhibit a crystal transition at a relative humidity from 3% to 70%. However it changed to a mixture of crystalline forms of the mesylate (Form B) and (Form C) at a relative humidity of 75% and 80%, a transition to a crystalline form of the mesylate (Form C) was observed. At a relative humidity of 85%, there was a complete transition to a crystalline form of the mesylate (Form C).

Test Example 5

Temperature-controlled Powder X-ray Diffraction of a Crystalline Form of the Dimethyl Sulfoxide Solvate of the Mesylate (Obtained in Example 8 (Preparation Method 1))

[Method]

Powder X-ray diffraction was conducted under the measurement conditions similar to those in 4. (powder X-ray diffraction) of Test Examples 3. The temperature was increased according to the following conditions.
Temperature controller: PCT-20 (manufactured by Rigaku Denki K.K.)
Rate for the increase of the temperature: 2° C./min
Measurement temperatures: 30° C., 40° C., 60° C., 80° C., 120° C., 140° C., 180° C., 200° C., 205° C., 210° C. and 215° C.

[Results]

While crystal transition was not observed at temperatures from 30° C. to 80° C., at temperatures of 120° C. or more transition to a crystalline form of the mesylate (Form C) was observed.

(Powder X-ray Diffraction Measurement)

Powder X-ray diffraction analysis was carried out for crystals obtained in Preparation Example 1 and Examples 1, 2, 3, 4, 5, 6, 7, 9, 10, 11 and 12 under the following measurement conditions in accordance with "X-Ray Powder Diffraction Method" described in Japanese Pharmacopoeia 14th Edition, General Tests (B-614 to 619).
Apparatus: RINT-2000 (manufactured by Rigaku Denki K.K.)
X-ray: CuKα ray
Monochrometer: curved crystal monochrometer
Goniometer: vertical goniometer
Counter: scintillation counter
Applied voltage: 40 kV
Charging current: 200 mA
Scan speed: 5°/min (2°/min with respect to a crystalline form of the free form of the carboxamide obtained in Preparation Example 1, a crystalline form of the hydrochloride obtained in Example 1, a crystalline form of the hydrobromide obtained in Example 2, and a crystalline form of the acetic acid solvate of the mesylate (Form I) obtained in Example 10)
Scan axis: 2θ/θ
Scan range: 2θ+5 to 40°
Divergent slit: 0.5°
Scattering slit: 0.5°
Receiving slit: 0.3 mm The powder X-ray diffraction patterns of the crystals obtained in Preparation Example 1 and Examples 1, 2, 3, 4, 5, 6, 7, 9, 10, 11 and 12 are shown in FIGS. 2 to 13, respectively. The peaks and intensities of the diffraction angles (2θ) for the crystals obtained in Preparation Example 1 and Examples 5, 6, 7, 9, 10, 11 and 12 are listed in Tables 12 to 19, respectively.

TABLE 12

| PEAK NUMBER | 2θ | HALF WIDTH | d_VALUE | INTENSITY | RELATIVE INTENSITY |
|---|---|---|---|---|---|
| 1 | 7.210 | 0.165 | 12.2505 | 1593 | 7 |
| 2 | 8.250 | 0.153 | 10.7084 | 4113 | 18 |
| 3 | 8.930 | 0.176 | 9.8944 | 1680 | 7 |
| 4 | 9.200 | 0.141 | 9.6046 | 1710 | 8 |
| 5 | 9.910 | 0.165 | 8.9180 | 3680 | 16 |
| 6 | 10.430 | 0.188 | 8.4746 | 2220 | 10 |
| 7 | 10.930 | 0.153 | 8.0880 | 4197 | 19 |
| 8 | 12.240 | 0.188 | 7.2251 | 1853 | 8 |
| 9 | 13.720 | 0.165 | 6.4489 | 6133 | 27 |
| 10 | 15.090 | 0.165 | 5.8664 | 2283 | 10 |
| 11 | 15.370 | 0.141 | 5.7601 | 2553 | 11 |
| 12 | 15.700 | 0.176 | 5.6398 | 7390 | 33 |
| 13 | 16.550 | 0.188 | 5.3520 | 1293 | 6 |
| 14 | 18.580 | 0.176 | 4.7716 | 9897 | 44 |
| 15 | 19.230 | 0.188 | 4.6117 | 15977 | 71 |
| 16 | 19.930 | 0.165 | 4.4513 | 4683 | 21 |
| 17 | 20.330 | 0.188 | 4.3646 | 13577 | 60 |
| 18 | 20.970 | 0.176 | 4.2328 | 3610 | 16 |
| 19 | 22.010 | 0.176 | 4.0351 | 3100 | 14 |
| 20 | 22.410 | 0.259 | 3.9640 | 5203 | 23 |
| 21 | 22.970 | 0.165 | 3.8686 | 2593 | 12 |
| 22 | 23.440 | 0.188 | 3.7921 | 22513 | 100 |
| 23 | 24.110 | 0.176 | 3.6882 | 5120 | 23 |
| 24 | 24.540 | 0.176 | 3.6245 | 5353 | 24 |
| 25 | 24.990 | 0.188 | 3.5603 | 5263 | 23 |
| 26 | 25.520 | 0.188 | 3.4875 | 1867 | 8 |
| 27 | 25.790 | 0.141 | 3.4516 | 1370 | 6 |
| 28 | 26.280 | 0.188 | 3.3884 | 8420 | 37 |
| 29 | 26.880 | 0.188 | 3.3141 | 4030 | 18 |
| 30 | 27.400 | 0.176 | 3.2524 | 2080 | 9 |
| 31 | 27.710 | 0.176 | 3.2167 | 2077 | 9 |
| 32 | 28.010 | 0.141 | 3.1829 | 1190 | 5 |
| 33 | 28.560 | 0.188 | 3.1228 | 4867 | 22 |
| 34 | 28.860 | 0.165 | 3.0911 | 3810 | 17 |
| 35 | 29.400 | 0.212 | 3.0355 | 2050 | 9 |
| 36 | 30.490 | 0.188 | 2.9294 | 6207 | 28 |
| 37 | 30.880 | 0.247 | 2.8933 | 2667 | 12 |
| 38 | 31.280 | 0.188 | 2.8572 | 1397 | 6 |
| 39 | 31.760 | 0.259 | 2.8151 | 3050 | 14 |
| 40 | 32.100 | 0.176 | 2.7861 | 1447 | 6 |
| 41 | 32.920 | 0.129 | 2.7185 | 1310 | 6 |
| 42 | 33.120 | 0.212 | 2.7026 | 1697 | 7 |
| 43 | 33.710 | 0.141 | 2.6566 | 1337 | 6 |
| 44 | 34.290 | 0.259 | 2.6130 | 1163 | 5 |
| 45 | 34.640 | 0.165 | 2.5874 | 1223 | 5 |
| 46 | 34.940 | 0.188 | 2.5658 | 1350 | 6 |
| 47 | 36.080 | 0.176 | 2.4873 | 1117 | 5 |
| 48 | 36.730 | 0.176 | 2.4448 | 2140 | 10 |
| 49 | 37.600 | 0.235 | 2.3902 | 1677 | 7 |
| 50 | 38.140 | 0.188 | 2.3576 | 1500 | 7 |
| 51 | 38.600 | 0.212 | 2.3306 | 1200 | 5 |
| 52 | 39.400 | 0.271 | 2.2851 | 1650 | 7 |

TABLE 13

| PEAK NUMBER | 2θ | HALF WIDTH | d_VALUE | INTENSITY | RELATIVE INTENSITY |
|---|---|---|---|---|---|
| 1 | 6.540 | 0.188 | 13.5039 | 1954 | 10 |
| 2 | 9.660 | 0.141 | 9.1483 | 9646 | 52 |
| 3 | 10.640 | 0.188 | 8.3078 | 2662 | 14 |
| 4 | 11.380 | 0.141 | 7.7692 | 3025 | 16 |
| 5 | 12.220 | 0.212 | 7.2369 | 1592 | 9 |
| 6 | 12.640 | 0.141 | 8.9974 | 1808 | 10 |
| 7 | 13.100 | 0.165 | 6.7527 | 1917 | 10 |
| 8 | 14.480 | 0.141 | 6.1121 | 1904 | 10 |
| 9 | 15.020 | 0.165 | 5.8935 | 1304 | 7 |
| 10 | 15.420 | 0.212 | 5.7415 | 1600 | 9 |
| 11 | 16.740 | 0.165 | 5.2917 | 3446 | 18 |
| 12 | 17.020 | 0.185 | 5.2052 | 1704 | 9 |
| 13 | 17.300 | 0.141 | 5.1216 | 2129 | 11 |
| 14 | 17.700 | 0.165 | 5.0068 | 2329 | 12 |
| 15 | 18.380 | 0.165 | 4.8230 | 3825 | 20 |
| 16 | 18.880 | 0.165 | 4.6964 | 3479 | 19 |
| 17 | 19.400 | 0.235 | 4.5717 | 2800 | 15 |
| 18 | 19.960 | 0.165 | 4.4447 | 4054 | 22 |
| 19 | 20.340 | 0.141 | 4.3625 | 4133 | 22 |
| 20 | 20.820 | 0.235 | 4.2630 | 10558 | 56 |
| 21 | 21.380 | 0.165 | 4.1526 | 5504 | 29 |
| 22 | 22.180 | 0.188 | 4.0046 | 4988 | 27 |
| 23 | 22.900 | 0.165 | 3.8803 | 5158 | 28 |
| 24 | 23.180 | 0.141 | 3.8340 | 9562 | 51 |
| 25 | 23.420 | 0.165 | 3.7953 | 18721 | 100 |
| 26 | 24.080 | 0.141 | 3.6927 | 2438 | 13 |
| 27 | 24.820 | 0.188 | 3.5843 | 3908 | 21 |
| 28 | 25.480 | 0.212 | 3.4929 | 3183 | 17 |
| 29 | 25.880 | 0.212 | 3.4398 | 2012 | 11 |
| 30 | 26.400 | 0.141 | 3.3732 | 2288 | 12 |
| 31 | 26.740 | 0.188 | 3.3311 | 3568 | 19 |
| 32 | 27.060 | 0.141 | 3.2924 | 1192 | 6 |
| 33 | 27.640 | 0.212 | 3.2247 | 2842 | 15 |
| 34 | 28.320 | 0.212 | 3.1488 | 1812 | 10 |
| 35 | 28.600 | 0.141 | 3.1186 | 1892 | 10 |
| 36 | 29.220 | 0.165 | 3.0538 | 1746 | 9 |
| 37 | 25.680 | 0.141 | 3.0075 | 3154 | 17 |
| 38 | 29.960 | 0.188 | 2.9800 | 6300 | 28 |
| 39 | 30.300 | 0.165 | 2.9474 | 1846 | 10 |
| 40 | 31.800 | 0.118 | 2.8117 | 1412 | 8 |
| 41 | 32.660 | 0.212 | 2.7396 | 2133 | 11 |
| 42 | 32.940 | 0.141 | 2.7169 | 1567 | 8 |
| 43 | 33.360 | 0.259 | 2.6837 | 1312 | 7 |
| 44 | 35.400 | 0.141 | 2.5335 | 1867 | 10 |
| 45 | 36.550 | 0.235 | 2.4493 | 1167 | 6 |
| 46 | 37.240 | 0.259 | 2.4125 | 1412 | 8 |
| 47 | 38.320 | 0.165 | 2.3469 | 1575 | 8 |
| 48 | 38.700 | 0.118 | 2.3248 | 1425 | 8 |

TABLE 14

| PEAK NUMBER | 2θ | HALF WIDTH | d_VALUE | INTENSITY | RELATIVE INTENSITY |
|---|---|---|---|---|---|
| 1 | 5.720 | 0.141 | 15.4378 | 3079 | 45 |
| 2 | 9.640 | 0.165 | 9.1672 | 2229 | 33 |
| 3 | 10.140 | 0.188 | 8.7163 | 2788 | 41 |
| 4 | 10.500 | 0.235 | 8.4182 | 2458 | 36 |
| 5 | 11.320 | 0.212 | 7.8102 | 4175 | 61 |
| 6 | 11.480 | 0.141 | 7.7017 | 4042 | 59 |
| 7 | 13.200 | 0.118 | 6.6716 | 1550 | 23 |
| 8 | 13.840 | 0.212 | 6.3933 | 3333 | 49 |
| 9 | 15.280 | 0.165 | 5.7938 | 1862 | 27 |
| 10 | 15.620 | 0.188 | 5.6685 | 1508 | 22 |
| 11 | 16.440 | 0.212 | 5.3875 | 1488 | 22 |
| 12 | 17.060 | 0.165 | 5.1931 | 2154 | 32 |
| 13 | 17.620 | 0.259 | 5.0293 | 4746 | 69 |
| 14 | 19.160 | 0.212 | 4.6284 | 6829 | 100 |
| 15 | 19.800 | 0.235 | 4.4802 | 2896 | 42 |
| 16 | 20.340 | 0.282 | 4.3625 | 2279 | 33 |
| 17 | 20.760 | 0.212 | 4.2752 | 2079 | 30 |
| 18 | 21.460 | 0.188 | 4.1373 | 2558 | 37 |
| 19 | 22.080 | 0.259 | 4.0225 | 1871 | 27 |
| 20 | 22.560 | 0.118 | 3.9380 | 2292 | 34 |
| 21 | 23.140 | 0.141 | 3.8406 | 3012 | 44 |
| 22 | 23.840 | 0.306 | 3.7293 | 3167 | 46 |
| 23 | 24.940 | 0.353 | 3.5673 | 3958 | 58 |
| 24 | 25.780 | 0.212 | 3.4629 | 3571 | 52 |
| 25 | 26.800 | 0.118 | 3.3238 | 1458 | 21 |
| 26 | 28.300 | 0.118 | 3.1509 | 2029 | 30 |
| 27 | 29.900 | 0.165 | 2.9859 | 1683 | 26 |
| 28 | 31.040 | 0.118 | 2.8788 | 1467 | 21 |
| 29 | 31.160 | 0.118 | 2.8679 | 1379 | 20 |
| 30 | 32.760 | 0.165 | 2.7314 | 1429 | 21 |
| 31 | 33.560 | 0.118 | 2.6681 | 1671 | 24 |
| 32 | 34.440 | 0.141 | 2.6019 | 1267 | 19 |

TABLE 15

| PEAK NUMBER | 2θ | HALF WIDTH | d_VALUE | INTENSITY | RELATIVE INTENSITY |
|---|---|---|---|---|---|
| 1 | 6.160 | 0.141 | 14.3361 | 3760 | 37 |
| 2 | 9.840 | 0.165 | 8.9813 | 3062 | 31 |
| 3 | 10.160 | 0.165 | 8.6992 | 3238 | 32 |
| 4 | 10.580 | 0.141 | 8.3547 | 7715 | 77 |
| 5 | 12.300 | 0.141 | 7.1900 | 1923 | 19 |
| 6 | 12.540 | 0.118 | 7.0530 | 1783 | 18 |
| 7 | 12.960 | 0.141 | 6.8263 | 1912 | 19 |
| 8 | 13.400 | 0.141 | 6.6022 | 1655 | 16 |
| 9 | 14.220 | 0.212 | 6.2233 | 3978 | 40 |
| 10 | 14.860 | 0.188 | 5.9566 | 1905 | 19 |
| 11 | 15.200 | 0.165 | 5.8241 | 3047 | 30 |
| 12 | 15.960 | 0.236 | 5.5485 | 1383 | 14 |
| 13 | 16.360 | 0.212 | 5.4137 | 1267 | 13 |
| 14 | 17.160 | 0.141 | 5.1631 | 1793 | 18 |
| 15 | 17.600 | 0.282 | 5.0350 | 4173 | 42 |
| 16 | 19.080 | 0.165 | 4.6476 | 6007 | 60 |
| 17 | 19.280 | 0.165 | 4.5999 | 5715 | 57 |
| 18 | 19.960 | 0.188 | 4.4447 | 4740 | 47 |
| 19 | 20.420 | 0.165 | 4.3456 | 2607 | 26 |
| 20 | 20.820 | 0.212 | 4.2630 | 3305 | 33 |
| 21 | 21.280 | 0.188 | 4.1719 | 3210 | 32 |
| 22 | 21.740 | 0.235 | 4.0846 | 4487 | 45 |
| 23 | 22.560 | 0.282 | 3.9380 | 3627 | 36 |
| 24 | 23.140 | 0.188 | 3.8406 | 2402 | 24 |
| 25 | 23.560 | 0.188 | 3.7730 | 10033 | 100 |
| 26 | 23.720 | 0.118 | 3.7479 | 6733 | 67 |
| 27 | 24.020 | 0.141 | 3.7018 | 5015 | 50 |
| 28 | 24.320 | 0.259 | 3.6668 | 4275 | 43 |
| 29 | 24.760 | 0.259 | 3.5928 | 2563 | 26 |
| 30 | 25.540 | 0.282 | 3.4848 | 8082 | 81 |
| 31 | 26.020 | 0.141 | 3.4216 | 2278 | 23 |
| 32 | 26.220 | 0.118 | 3.3960 | 1422 | 14 |
| 33 | 26.980 | 0.212 | 3.3020 | 2438 | 24 |
| 34 | 27.500 | 0.165 | 3.2408 | 1085 | 11 |
| 35 | 27.980 | 0.235 | 3.1862 | 1798 | 18 |
| 36 | 28.400 | 0.212 | 3.1401 | 2785 | 28 |
| 37 | 28.760 | 0.141 | 3.1016 | 1137 | 11 |
| 38 | 29.220 | 0.212 | 3.0538 | 1517 | 15 |
| 39 | 29.500 | 0.118 | 3.0254 | 1727 | 17 |
| 40 | 29.620 | 0.165 | 3.0134 | 1818 | 18 |
| 41 | 29.840 | 0.118 | 2.9917 | 1643 | 16 |
| 42 | 30.640 | 0.376 | 2.9154 | 2390 | 24 |
| 43 | 31.280 | 0.259 | 2.8572 | 1123 | 11 |
| 44 | 31.500 | 0.118 | 2.8378 | 1062 | 11 |
| 45 | 32.440 | 0.141 | 2.7576 | 1100 | 11 |
| 46 | 33.640 | 0.118 | 2.6620 | 1208 | 12 |
| 47 | 34.500 | 0.165 | 2.5975 | 1362 | 14 |
| 48 | 35.040 | 0.118 | 2.5587 | 1297 | 13 |
| 49 | 36.100 | 0.188 | 2.4860 | 1245 | 12 |
| 50 | 37.640 | 0.306 | 2.3878 | 1565 | 16 |
| 51 | 38.940 | 0.141 | 2.3110 | 1427 | 14 |
| 52 | 39.480 | 0.118 | 2.2806 | 1215 | 12 |

TABLE 16

| PEAK NUMBER | 2θ | HALF WIDTH | d_VALUE | INTENSITY | RELATIVE INTENSITY |
|---|---|---|---|---|---|
| 1 | 5.700 | 0.212 | 15.4919 | 1821 | 25 |
| 2 | 6.100 | 0.188 | 14.4770 | 1946 | 26 |
| 3 | 8.020 | 0.212 | 11.0149 | 4092 | 56 |
| 4 | 9.640 | 0.212 | 9.1672 | 2379 | 32 |
| 5 | 10.540 | 0.165 | 8.3864 | 2021 | 27 |
| 6 | 11.280 | 0.259 | 7.8378 | 3871 | 53 |
| 7 | 12.680 | 0.236 | 6.9764 | 2129 | 29 |
| 8 | 14.140 | 0.259 | 6.2683 | 1358 | 18 |
| 9 | 16.120 | 0.212 | 5.4938 | 1529 | 21 |
| 10 | 17.200 | 0.259 | 5.1512 | 2258 | 31 |
| 11 | 18.140 | 0.235 | 4.8863 | 5121 | 70 |
| 12 | 19.520 | 0.235 | 4.5209 | 3671 | 50 |
| 13 | 20.240 | 0.165 | 4.3838 | 1921 | 26 |
| 14 | 20.700 | 0.329 | 4.2874 | 2962 | 40 |
| 15 | 21.320 | 0.235 | 4.1641 | 1525 | 21 |
| 16 | 22.120 | 0.212 | 4.0153 | 2558 | 35 |
| 17 | 22.900 | 0.282 | 3.8803 | 5721 | 78 |
| 18 | 23.400 | 0.188 | 3.7985 | 4458 | 61 |
| 19 | 23.740 | 0.259 | 3.7448 | 5092 | 69 |
| 20 | 24.280 | 0.259 | 3.6628 | 3929 | 53 |
| 21 | 24.760 | 0.188 | 3.5928 | 1971 | 27 |
| 22 | 25.060 | 0.235 | 3.5505 | 2164 | 29 |
| 23 | 25.500 | 0.282 | 3.4902 | 2454 | 33 |
| 24 | 26.300 | 0.282 | 3.3858 | 2083 | 28 |
| 25 | 26.960 | 0.329 | 3.3044 | 7362 | 100 |
| 26 | 28.300 | 0.212 | 3.1509 | 1921 | 26 |
| 27 | 28.820 | 0.306 | 3.0953 | 1850 | 25 |
| 28 | 29.480 | 0.329 | 3.0274 | 2371 | 32 |
| 29 | 29.920 | 0.165 | 2.9839 | 1554 | 21 |
| 30 | 31.660 | 0.353 | 2.8238 | 1321 | 18 |
| 31 | 34.840 | 0.259 | 2.5730 | 1700 | 23 |
| 32 | 36.280 | 0.329 | 2.4741 | 1888 | 26 |
| 33 | 37.940 | 0.165 | 2.3696 | 1400 | 19 |

TABLE 17

| PEAK NUMBER | 2θ | HALF WIDTH | d_VALUE | INTENSITY | RELATIVE INTENSITY |
|---|---|---|---|---|---|
| 1 | 9.360 | 0.188 | 9.4408 | 6027 | 100 |
| 2 | 10.200 | 0.165 | 8.6651 | 2107 | 35 |
| 3 | 10.460 | 0.165 | 8.4503 | 3292 | 55 |
| 4 | 12.400 | 0.165 | 7.1323 | 2693 | 46 |
| 5 | 13.380 | 0.188 | 6.6120 | 1382 | 23 |
| 6 | 13.880 | 0.235 | 6.3749 | 1450 | 24 |
| 7 | 14.400 | 0.165 | 6.1459 | 1432 | 24 |
| 8 | 15.640 | 0.282 | 5.6613 | 3673 | 61 |
| 9 | 16.840 | 0.165 | 5.2605 | 1560 | 26 |
| 10 | 17.260 | 0.118 | 5.1334 | 2425 | 40 |
| 11 | 17.460 | 0.165 | 5.0750 | 4155 | 69 |
| 12 | 18.860 | 0.212 | 4.7014 | 2442 | 40 |
| 13 | 19.420 | 0.212 | 4.5670 | 1597 | 26 |
| 14 | 20.040 | 0.212 | 4.4271 | 2845 | 47 |
| 15 | 20.760 | 0.212 | 4.2752 | 3693 | 61 |
| 16 | 21.100 | 0.212 | 4.2070 | 2805 | 46 |
| 17 | 21.760 | 0.188 | 4.0809 | 6035 | 100 |
| 18 | 22.660 | 0.212 | 3.9208 | 3982 | 66 |
| 19 | 23.200 | 0.188 | 3.8308 | 1322 | 22 |
| 20 | 23.660 | 0.212 | 3.7573 | 4177 | 69 |
| 21 | 25.180 | 0.329 | 3.5338 | 4802 | 80 |
| 22 | 25.660 | 0.188 | 3.4688 | 3073 | 51 |
| 23 | 25.840 | 0.141 | 3.4451 | 2603 | 43 |
| 24 | 26.480 | 0.188 | 3.3632 | 1992 | 33 |
| 25 | 26.980 | 0.236 | 3.3020 | 2142 | 35 |
| 26 | 28.040 | 0.329 | 3.1796 | 2292 | 38 |
| 27 | 28.480 | 0.118 | 3.1314 | 995 | 16 |
| 28 | 29.740 | 0.282 | 3.0016 | 1248 | 21 |
| 29 | 30.360 | 0.282 | 2.9417 | 1915 | 32 |
| 30 | 31.200 | 0.188 | 2.8644 | 1075 | 18 |
| 31 | 31.640 | 0.118 | 2.8255 | 960 | 16 |
| 32 | 32.520 | 0.141 | 2.7510 | 1057 | 18 |
| 33 | 33.340 | 0.212 | 2.6852 | 1740 | 29 |
| 34 | 35.120 | 0.118 | 2.5531 | 985 | 16 |
| 35 | 35.440 | 0.141 | 2.5308 | 953 | 16 |
| 36 | 35.860 | 0.165 | 2.5021 | 937 | 16 |
| 37 | 37.360 | 0.259 | 2.4050 | 1443 | 24 |
| 38 | 39.560 | 0.141 | 2.2762 | 1217 | 20 |

TABLE 18

| PEAK NUMBER | 2θ | HALF WIDTH | d_VALUE | INTENSITY | RELATIVE INTENSITY | PEAK NUMBER |
|---|---|---|---|---|---|---|
| 1 | 6.000 | 0.188 | 14.7180 | 2058 | 37 |
| 2 | 9.200 | 0.447 | 9.6046 | 2108 | 38 |
| 3 | 10.640 | 0.235 | 8.3078 | 5392 | 96 |
| 4 | 13.480 | 0.165 | 6.5632 | 1862 | 33 |
| 5 | 13.620 | 0.165 | 6.4960 | 1783 | 32 |
| 6 | 14.520 | 0.212 | 6.0953 | 1946 | 35 |
| 7 | 15.700 | 0.259 | 5.6398 | 2775 | 49 |
| 8 | 17.180 | 0.282 | 5.1571 | 2508 | 45 |
| 9 | 17.820 | 0.282 | 4.9733 | 2579 | 46 |
| 10 | 18.380 | 0.259 | 4.8230 | 2571 | 46 |
| 11 | 19.880 | 0.306 | 4.4624 | 4421 | 79 |
| 12 | 20.720 | 0.259 | 4.2833 | 2712 | 48 |
| 13 | 21.460 | 0.518 | 4.1373 | 2692 | 48 |
| 14 | 22.200 | 0.259 | 4.0010 | 3658 | 65 |
| 15 | 22.820 | 0.471 | 3.8937 | 5621 | 100 |
| 16 | 24.160 | 0.165 | 3.6807 | 2438 | 43 |
| 17 | 24.600 | 0.282 | 3.6158 | 2942 | 52 |
| 18 | 25.560 | 0.306 | 3.4822 | 4200 | 75 |
| 19 | 26.200 | 0.188 | 3.3985 | 1667 | 30 |
| 20 | 26.900 | 0.353 | 3.3117 | 2196 | 39 |
| 21 | 27.180 | 0.165 | 3.2782 | 1854 | 33 |
| 22 | 28.220 | 0.353 | 3.1597 | 2212 | 39 |
| 23 | 29.320 | 0.353 | 3.0436 | 1696 | 30 |
| 24 | 30.260 | 0.212 | 2.9512 | 1721 | 31 |

TABLE 19

| PEAK NUMBER | 2θ | HALF WIDTH | d_VALUE | INTENSITY | RELATIVE INTENSITY |
|---|---|---|---|---|---|
| 1 | 8.480 | 0.165 | 13.6288 | 2662 | 20 |
| 2 | 9.040 | 0.141 | 9.7743 | 5021 | 38 |
| 3 | 9.580 | 0.141 | 9.2245 | 10096 | 76 |
| 4 | 10.600 | 0.118 | 8.3390 | 2671 | 20 |
| 5 | 12.500 | 0.141 | 7.0754 | 2096 | 16 |
| 6 | 13.660 | 0.141 | 6.4771 | 1558 | 12 |
| 7 | 14.640 | 0.212 | 6.0456 | 1712 | 13 |
| 8 | 15.080 | 0.141 | 5.8702 | 7054 | 53 |
| 9 | 17.740 | 0.235 | 4.9956 | 2675 | 20 |
| 10 | 18.140 | 0.165 | 4.8863 | 4188 | 32 |
| 11 | 19.100 | 0.141 | 4.6428 | 3083 | 23 |
| 12 | 19.400 | 0.212 | 4.5717 | 6029 | 45 |
| 13 | 19.700 | 0.141 | 4.5027 | 2796 | 21 |
| 14 | 20.080 | 0.141 | 4.4184 | 2862 | 22 |
| 15 | 20.380 | 0.141 | 4.3540 | 3279 | 25 |
| 16 | 20.660 | 0.165 | 4.2956 | 10933 | 82 |
| 17 | 20.920 | 0.141 | 4.2428 | 2729 | 21 |
| 18 | 21.280 | 0.118 | 4.1719 | 2771 | 21 |
| 19 | 21.520 | 0.165 | 4.1259 | 6142 | 46 |
| 20 | 21.740 | 0.141 | 4.0846 | 4908 | 37 |
| 21 | 22.140 | 0.165 | 4.0117 | 3754 | 28 |
| 22 | 22.680 | 0.165 | 3.9174 | 13275 | 100 |
| 23 | 23.220 | 0.165 | 3.8275 | 2008 | 15 |
| 24 | 23.640 | 0.188 | 3.7604 | 6554 | 49 |
| 25 | 24.260 | 0.165 | 3.6657 | 5350 | 40 |
| 26 | 24.880 | 0.165 | 3.5758 | 3129 | 24 |
| 27 | 25.160 | 0.141 | 3.5366 | 2350 | 18 |
| 28 | 25.320 | 0.118 | 3.5146 | 1879 | 14 |
| 29 | 26.100 | 0.165 | 3.4113 | 4004 | 30 |
| 30 | 26.260 | 0.141 | 3.3909 | 3646 | 27 |
| 31 | 26.740 | 0.188 | 3.3311 | 3650 | 27 |
| 32 | 27.260 | 0.188 | 3.2687 | 5421 | 41 |
| 33 | 27.480 | 0.141 | 3.2431 | 3008 | 23 |
| 34 | 28.360 | 0.165 | 3.1444 | 1767 | 13 |
| 35 | 28.580 | 0.141 | 3.1207 | 1267 | 10 |
| 36 | 29.300 | 0.141 | 3.0456 | 1404 | 11 |
| 37 | 29.560 | 0.212 | 3.0194 | 2117 | 16 |
| 38 | 30.360 | 0.212 | 2.9417 | 2275 | 17 |
| 39 | 30.860 | 0.188 | 2.8951 | 2250 | 17 |
| 40 | 31.860 | 0.141 | 2.8065 | 1392 | 10 |
| 41 | 32.140 | 0.118 | 2.7827 | 1204 | 9 |
| 42 | 33.600 | 0.259 | 2.6650 | 1779 | 13 |
| 43 | 35.360 | 0.141 | 2.5363 | 1800 | 14 |
| 44 | 35.580 | 0.141 | 2.5211 | 1408 | 11 |
| 45 | 36.360 | 0.141 | 2.4688 | 1896 | 14 |
| 46 | 36.740 | 0.118 | 2.4442 | 1650 | 12 |
| 47 | 37.520 | 0.235 | 2.3951 | 1650 | 12 |
| 48 | 38.180 | 0.235 | 2.3552 | 1471 | 11 |
| 49 | 38.900 | 0.235 | 2.3133 | 2033 | 15 |
| 50 | 39.640 | 0.118 | 2.2718 | 1500 | 11 |

($^{13}$C Solid State NMR Spectrum Measurement)

$^{13}$C Solid State NMR spectrum measurement was carried out for crystals obtained in Examples 5 and 7 under the following measurement conditions.

Apparatus: CMX-300 (Chemagnetics)

Measurement temperature: room temperature (22° C.)

Chemical shift reference: poly(dimethylsiloxane) (Internal Standard: 1.56 ppm)

Measurement nucleus: $^{13}$C (75.497791 MHz)

Relaxation delay: 25 sec

Pulse sequence: TOSS

Figure 14:
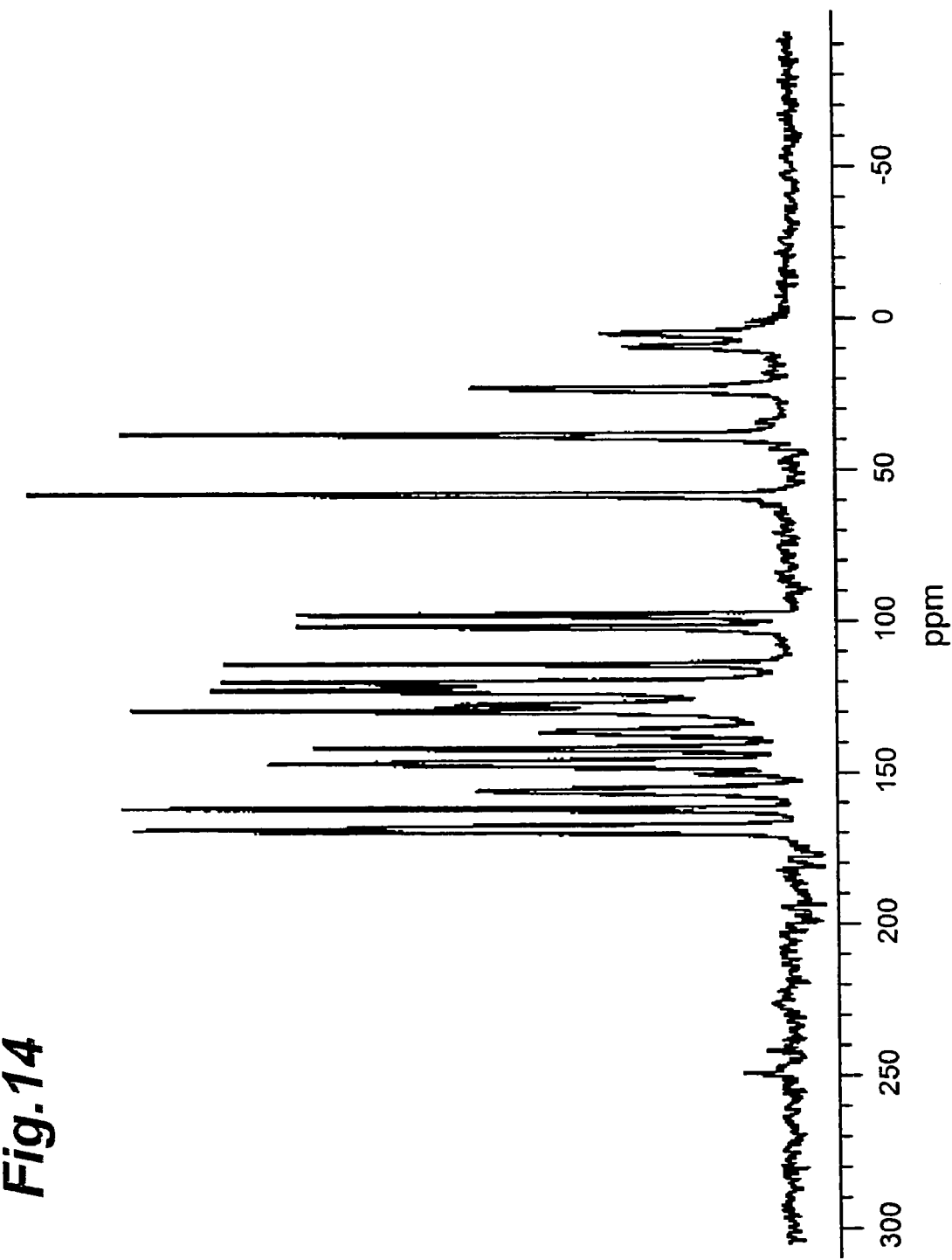
FIG. 14 is a figure illustrating a $^{13}C$ Solid State NMR spectrum for a crystalline form of the methanesulfonate of the carboxamide (Form A) obtained in Example 5.
Figure 15:
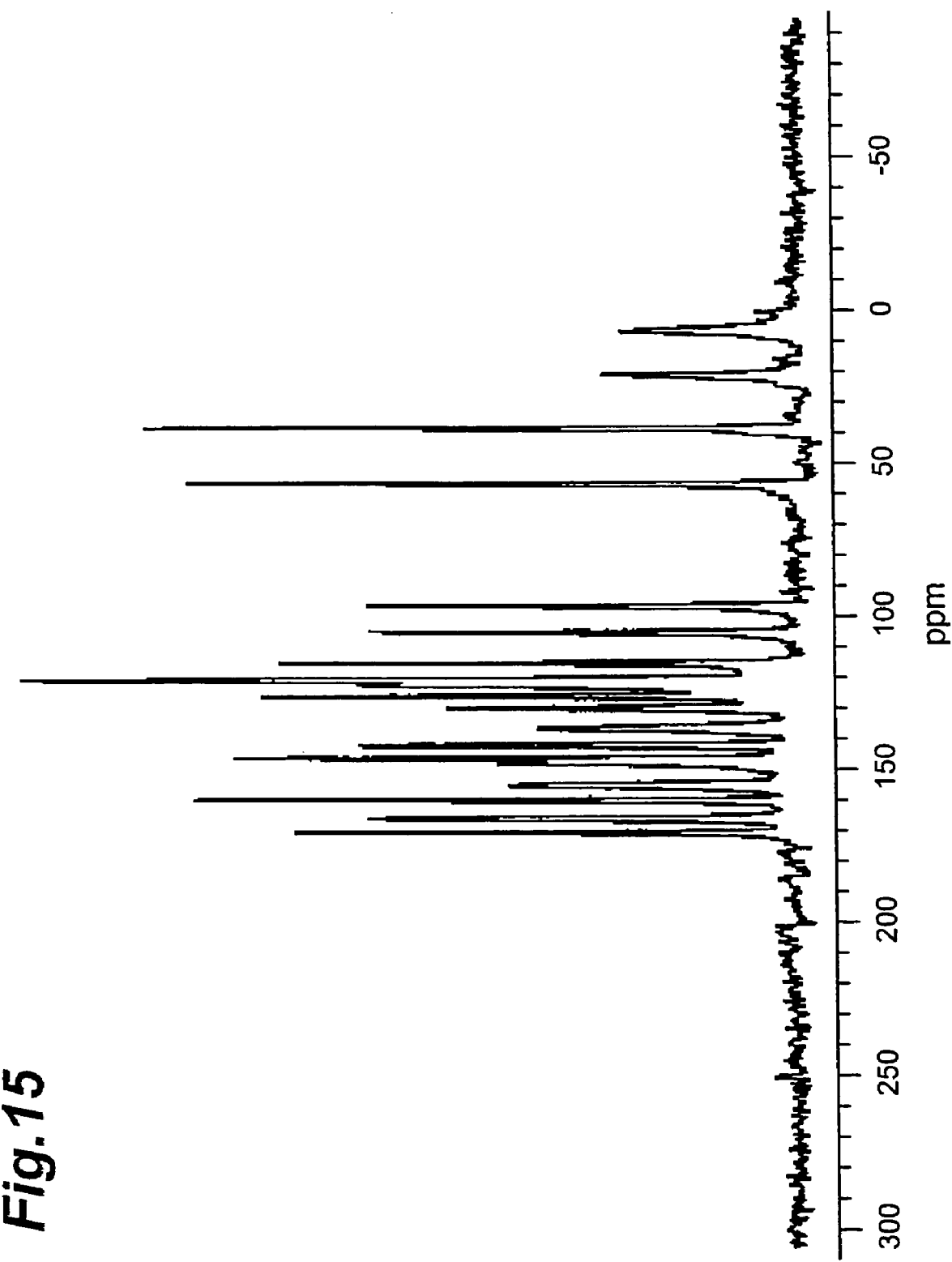
FIG. 15 is a figure illustrating a $^{13}C$ Solid State NMR spectrum for a crystalline form of the methanesulfonate of the carboxamide (Form C) obtained in Example 7.
Figure 16:
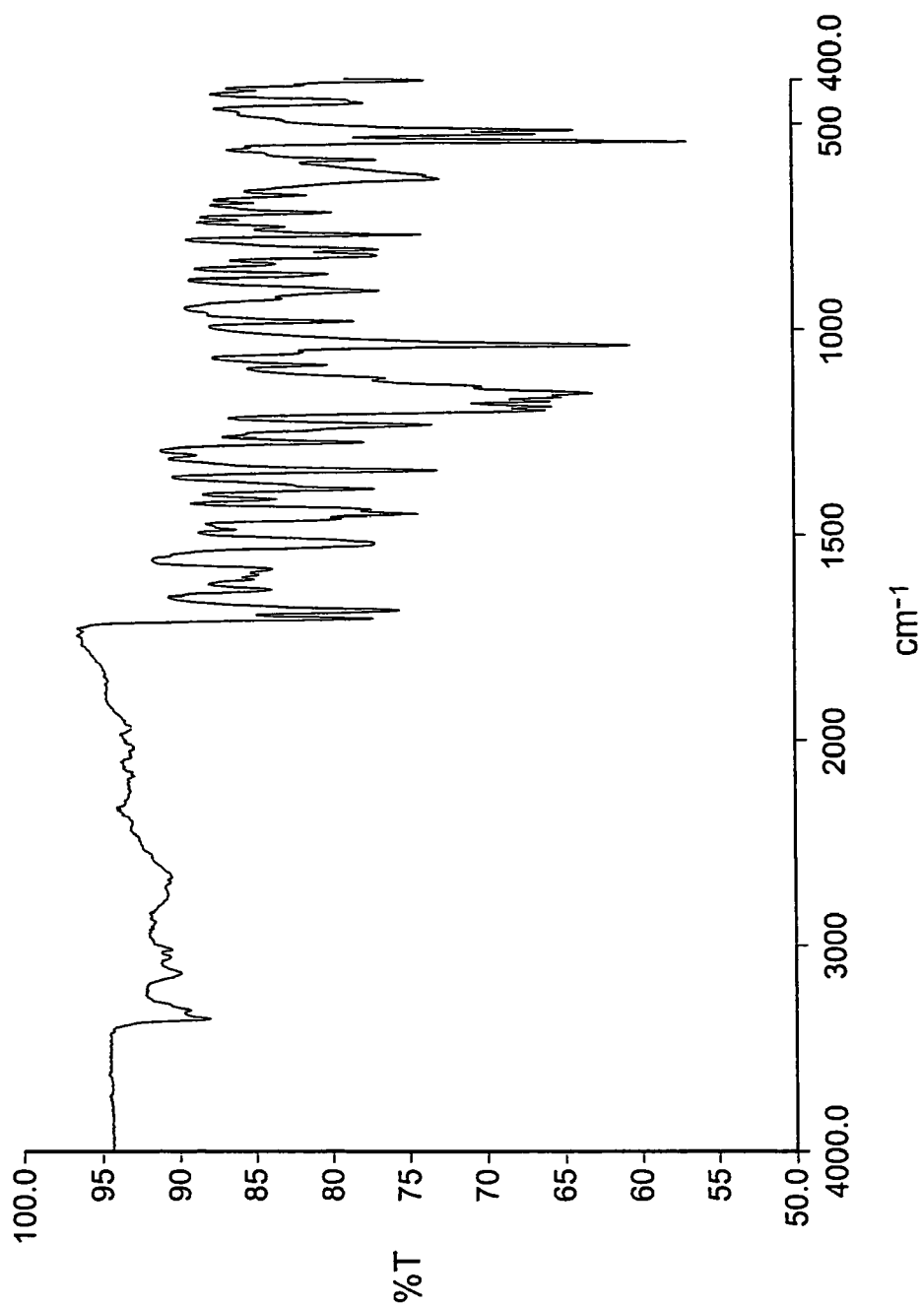
FIG. 16 is a figure illustrating an infrared absorption spectrum for a crystalline form of the methanesulfonate of the carboxamide (Form A) obtained in Example 5.
Figure 17:
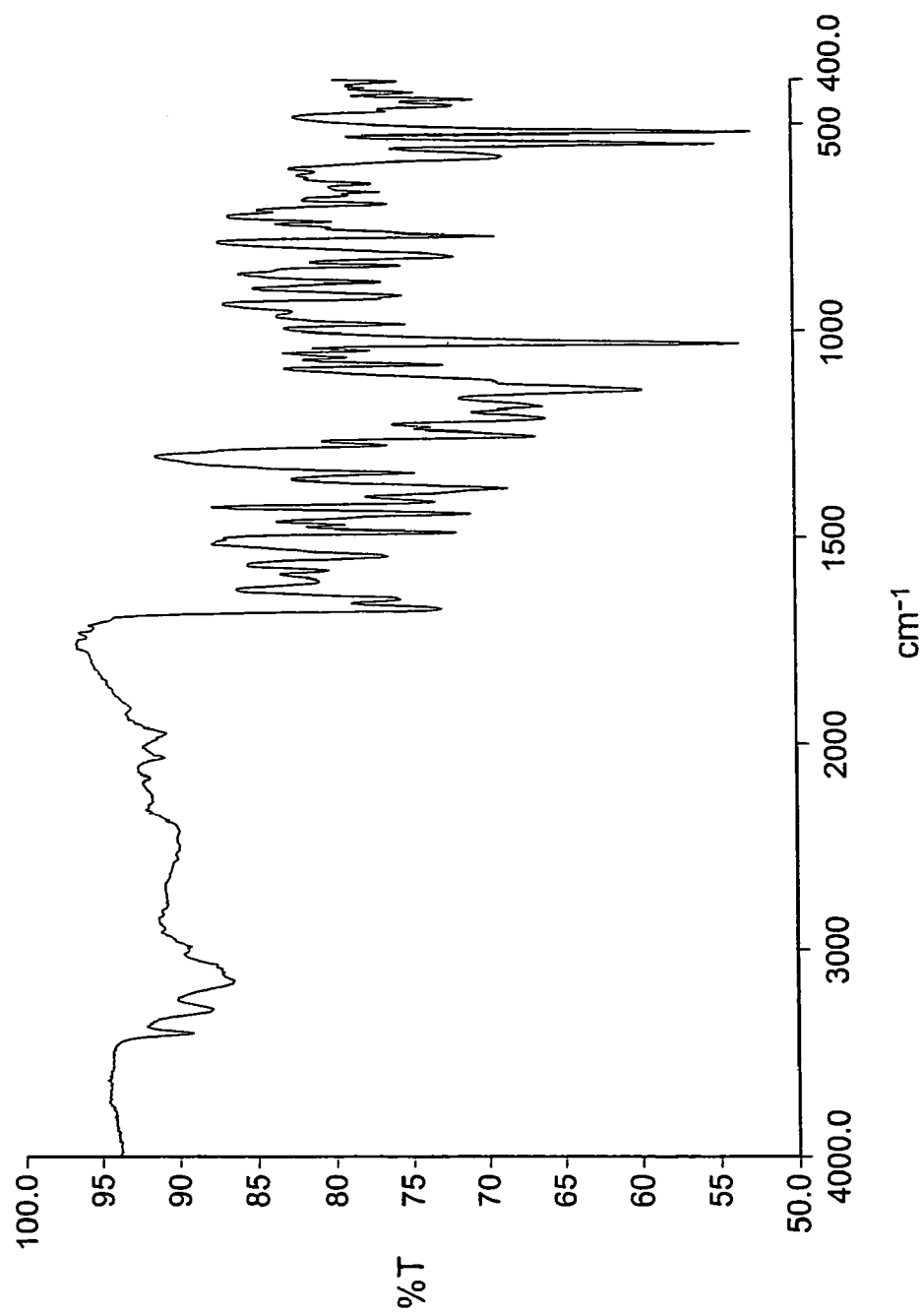
FIG. 17 is a figure illustrating an infrared absorption spectrum for a crystalline form of the methanesulfonate of the carboxamide
Figure 18:
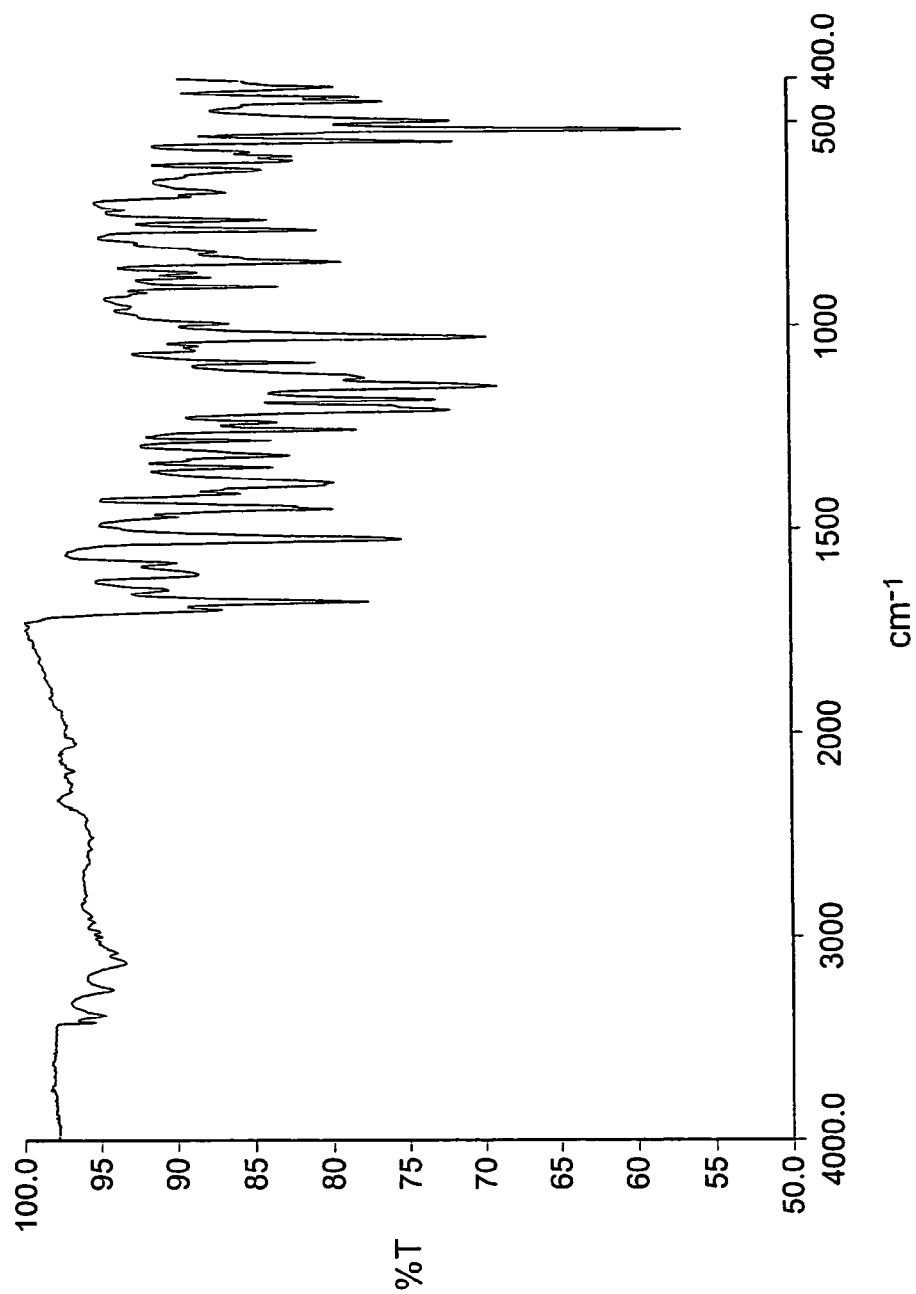
FIG. 18 is a figure illustrating an infrared absorption spectrum for a crystalline form of the methanesulfonate of the carboxamide (Form C) obtained in Example 7.
Figure 19:
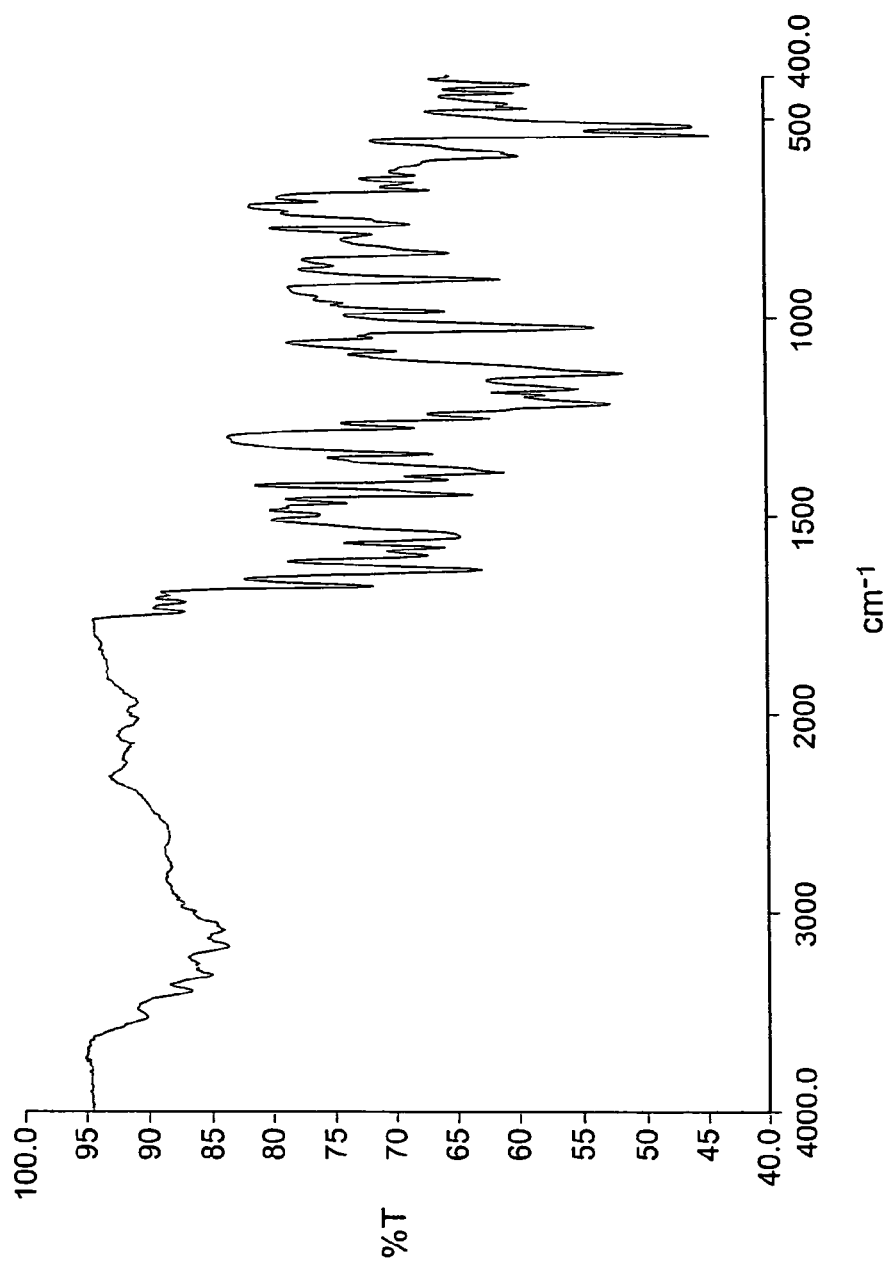
FIG. 19 is a figure illustrating an infrared absorption spectrum for a crystalline form of the acetic acid solvate of the methanesulfonate of the carboxamide (Form I) obtained in Example 10.
Figure 20:
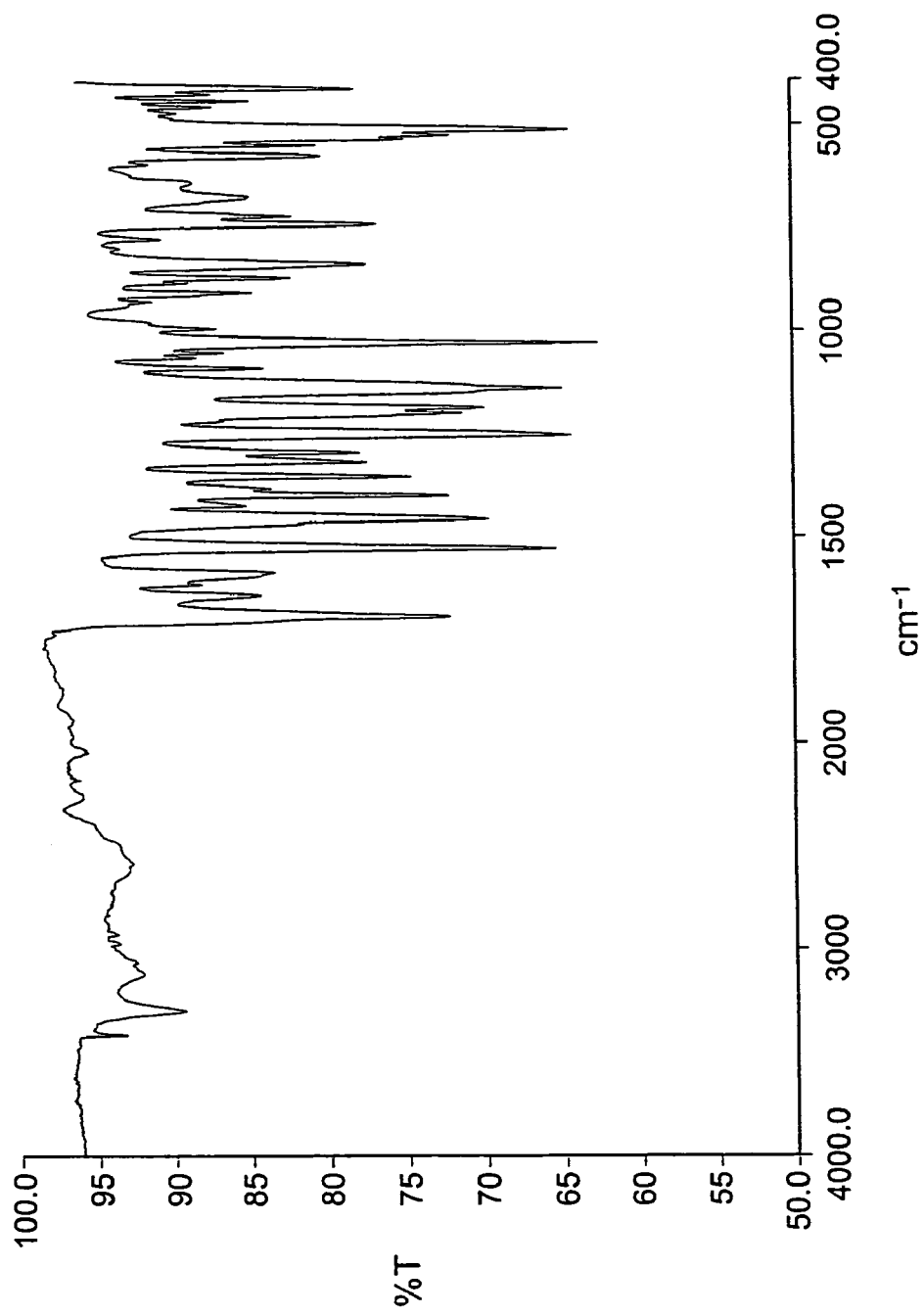
FIG. 20 is a figure illustrating an infrared absorption spectrum for a crystalline form of the ethanesulfonate of the carboxamide (Form α) obtained in Example 11.
Figure 21:
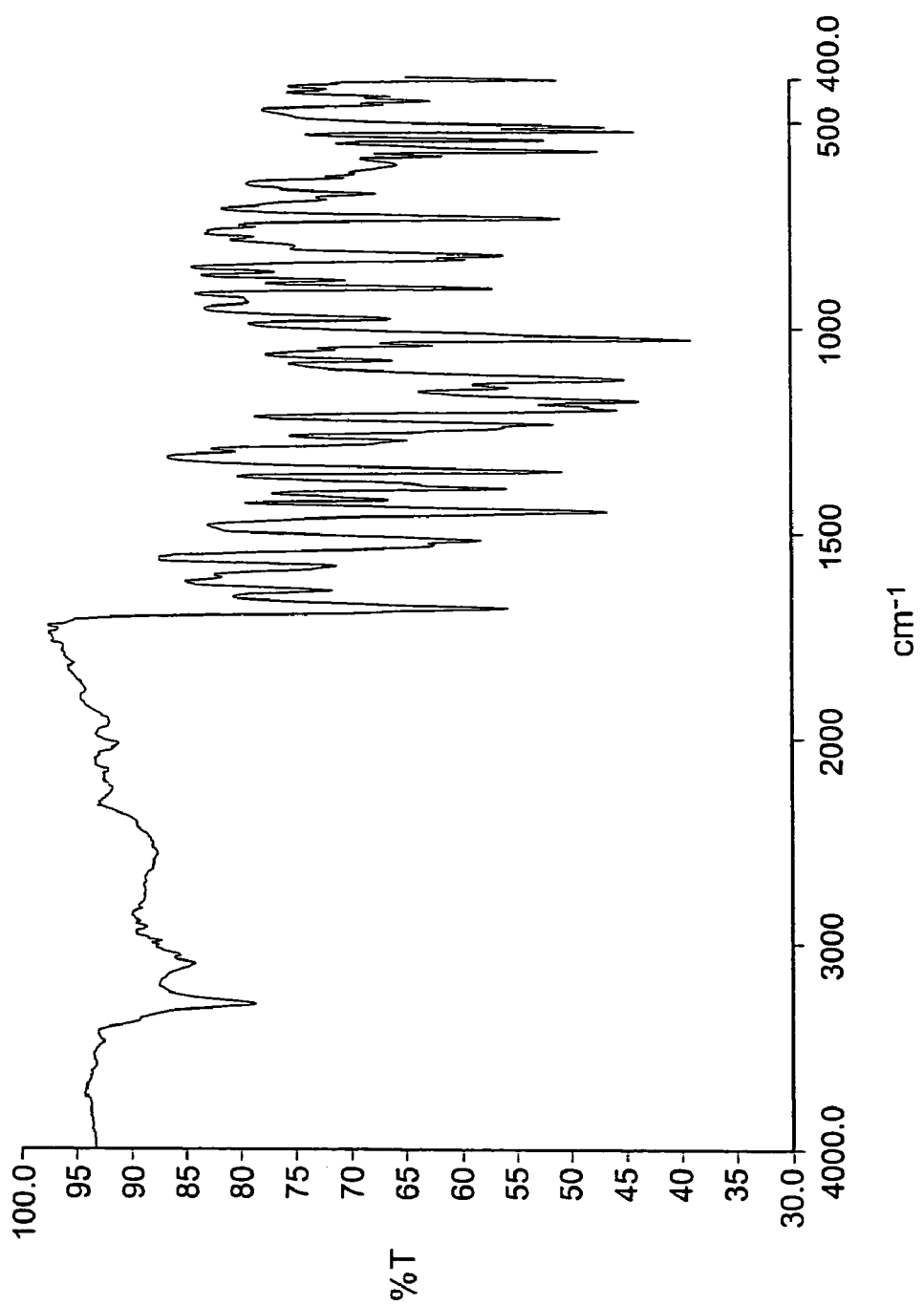
FIG. 21 is a figure illustrating an infrared absorption spectrum for a crystalline form of the ethanesulfonate of the carboxamide (Form β) obtained in Example 12.

The $^{13}$C Solid State NMR spectra of the crystals obtained in Examples 5 and 7 are shown in FIG. 14 and FIG. 15, respectively. The chemical shifts of the crystals obtained in Examples 5 and 7 are listed in Tables 20 and 21, respectively.

TABLE 20

| mesylate (Form A) chemical shift (ppm) |
|---|
| 169.7 |
| 162.4 |
| 156.3 |
| 147.5 |
| 142.3 |
| 137.0 |
| 130.1 |
| 128.0 |
| 123.4 |
| 120.5 |
| 114.6 |
| 102.3 |
| 98.4 |
| 58.8 |
| 39.2 |
| 23.8 |
| 9.9 |
| 5.7 |

TABLE 21

| mesylate (Form C) chemical shift (ppm) |
|---|
| 170.9 |
| 166.1 |
| 160.2 |
| 155.3 |
| 148.1 |
| 144.6 |
| 142.4 |
| 136.8 |
| 130.3 |
| 126.6 |
| 122.9 |
| 121.4 |
| 115.9 |
| 105.6 |
| 97.0 |
| 57.4 |
| 39.3 |
| 21.9 |
| 7.8 |

(Infrared Absorption Spectrum Measurement)

Infrared absorption spectrum measurement was carried out for crystals obtained in Examples 5, 6, 7, 10, 11 and 12 was carried out according to the ATR method in the infrared absorption spectrum method as described in the Japanese Pharmacopoeia 14th Edition, General Tests by using FT-IR Spectrum-One (manufactured by PerkinElmer Japan Co., Ltd.) with a measurement range of 4000-400 cm$^{-1}$ and a resolution of 4 cm$^{-1}$.

The infrared absorption spectra of the crystals obtained in Examples 5, 6, 7, 10, 11 and 12 are shown in FIGS. 16 to 21, respectively, and wave numbers of the absorption peaks (cm$^{-1}$) and transmittance (% T) are listed in Tables 22 to 27, respectively.

TABLE 22

| MESYLATE (FORM A) | |
|---|---|
| WAVE NUMBER (cm$^{-1}$) | % T |
| 3306.50 | 87.76 |
| 3143.87 | 89.68 |

TABLE 22-continued

MESYLATE (FORM A)

| WAVE NUMBER (cm$^{-1}$) | % T |
|---|---|
| 2676.03 | 90.20 |
| 2179.21 | 92.50 |
| 1709.03 | 76.99 |
| 1689.20 | 75.28 |
| 1639.51 | 83.49 |
| 1589.27 | 83.46 |
| 1526.06 | 76.88 |
| 1492.40 | 85.76 |
| 1456.75 | 74.01 |
| 1420.18 | 83.16 |
| 1350.26 | 72.77 |
| 1311.98 | 88.26 |
| 1280.50 | 77.49 |
| 1239.62 | 73.06 |
| 1204.43 | 65.76 |
| 1194.13 | 65.42 |
| 1181.63 | 65.44 |
| 1161.34 | 62.76 |
| 1091.07 | 79.89 |
| 1044.40 | 60.26 |
| 985.56 | 78.02 |
| 911.30 | 76.39 |
| 846.45 | 83.06 |
| 827.77 | 76.51 |
| 811.59 | 76.37 |
| 775.98 | 73.68 |
| 756.07 | 82.42 |
| 739.83 | 85.42 |
| 721.85 | 79.51 |
| 697.83 | 84.41 |
| 681.20 | 81.05 |
| 642.73 | 72.54 |
| 595.47 | 76.50 |
| 550.94 | 56.67 |
| 523.19 | 63.87 |
| 458.48 | 77.37 |
| 428.43 | 84.18 |
| 404.39 | 73.43 |

TABLE 23

MESYLATE (FORM B)

| WAVE NUMBER (cm$^{-1}$) | % T |
|---|---|
| 3403.30 | 88.90 |
| 3288.86 | 87.65 |
| 3148.98 | 86.30 |
| 2500.86 | 89.65 |
| 2071.00 | 90.59 |
| 1975.82 | 90.44 |
| 1676.34 | 72.60 |
| 1654.00 | 75.28 |
| 1610.72 | 80.67 |
| 1585.16 | 80.02 |
| 1549.95 | 76.15 |
| 1492.04 | 71.57 |
| 1474.49 | 78.84 |
| 1447.27 | 70.65 |
| 1418.76 | 72.95 |
| 1385.12 | 68.18 |
| 1349.46 | 74.29 |
| 1281.22 | 76.13 |
| 1259.90 | 66.26 |
| 1238.09 | 73.20 |
| 1216.34 | 65.61 |
| 1187.31 | 65.81 |
| 1147.23 | 59.40 |
| 1086.20 | 72.28 |
| 1068.05 | 78.63 |
| 1051.40 | 77.11 |

TABLE 23-continued

MESYLATE (FORM B)

| WAVE NUMBER (cm$^{-1}$) | % T |
|---|---|
| 1034.51 | 53.11 |
| 988.08 | 74.83 |
| 957.18 | 82.10 |
| 917.63 | 74.99 |
| 885.07 | 76.41 |
| 846.37 | 75.01 |
| 824.56 | 71.62 |
| 774.19 | 68.81 |
| 740.35 | 79.48 |
| 717.65 | 83.13 |
| 697.26 | 75.94 |
| 667.94 | 76.40 |
| 648.45 | 76.93 |
| 621.03 | 80.63 |
| 582.94 | 68.34 |
| 553.10 | 54.69 |
| 524.26 | 52.32 |
| 460.20 | 71.59 |
| 445.97 | 70.23 |
| 429.58 | 74.11 |
| 417.86 | 77.33 |
| 404.47 | 75.14 |

TABLE 24

MESYLATE (FORM C)

| WAVE NUMBER (cm$^{-1}$) | % T |
|---|---|
| 3423.95 | 95.31 |
| 3387.99 | 94.61 |
| 3265.37 | 94.09 |
| 3134.95 | 93.21 |
| 2189.73 | 96.49 |
| 2055.55 | 96.35 |
| 1701.76 | 86.67 |
| 1682.83 | 77.44 |
| 1652.89 | 90.15 |
| 1613.76 | 88.25 |
| 1587.67 | 89.60 |
| 1528.85 | 75.23 |
| 1474.24 | 89.39 |
| 1454.93 | 79.66 |
| 1417.85 | 85.41 |
| 1390.53 | 79.57 |
| 1352.31 | 83.39 |
| 1323.76 | 82.35 |
| 1286.71 | 83.52 |
| 1259.58 | 78.08 |
| 1241.58 | 83.13 |
| 1211.19 | 71.92 |
| 1185.21 | 72.85 |
| 1151.72 | 68.76 |
| 1132.10 | 77.56 |
| 1094.87 | 80.65 |
| 1053.79 | 88.07 |
| 1031.32 | 69.48 |
| 999.13 | 86.02 |
| 957.03 | 92.45 |
| 923.13 | 91.37 |
| 909.07 | 83.03 |
| 885.46 | 87.22 |
| 873.44 | 88.13 |
| 849.08 | 79.00 |
| 823.54 | 86.89 |
| 770.37 | 80.47 |
| 746.03 | 83.64 |
| 720.92 | 92.81 |
| 678.66 | 86.22 |
| 622.21 | 83.97 |
| 599.75 | 82.04 |
| 589.04 | 82.04 |

TABLE 24-continued

MESYLATE (FORM C)

| WAVE NUMBER (cm$^{-1}$) | % T |
|---|---|
| 578.57 | 84.66 |
| 553.91 | 71.59 |
| 522.49 | 56.69 |
| 502.44 | 71.80 |
| 456.20 | 76.23 |
| 446.12 | 77.77 |
| 419.73 | 79.39 |

TABLE 25

MESYLATE (FORM I)

| WAVE NUMBER (cm$^{-1}$) | % T |
|---|---|
| 3397.97 | 86.39 |
| 3319.94 | 84.81 |
| 3177.53 | 83.45 |
| 3096.06 | 83.80 |
| 2159.87 | 91.01 |
| 2032.91 | 90.61 |
| 1749.63 | 86.77 |
| 1724.72 | 86.69 |
| 1683.59 | 71.59 |
| 1641.48 | 62.67 |
| 1605.84 | 67.15 |
| 1585.45 | 65.70 |
| 1557.92 | 64.45 |
| 1505.67 | 75.91 |
| 1474.53 | 73.63 |
| 1453.55 | 63.44 |
| 1416.08 | 65.42 |
| 1396.67 | 60.87 |
| 1350.85 | 66.67 |
| 1284.69 | 68.19 |
| 1260.86 | 62.02 |
| 1223.56 | 52.48 |
| 1201.48 | 57.53 |
| 1186.05 | 55.01 |
| 1146.06 | 51.51 |
| 1091.15 | 69.64 |
| 1057.74 | 71.52 |
| 1030.17 | 53.75 |
| 989.94 | 65.62 |
| 971.08 | 73.93 |
| 909.73 | 61.10 |
| 876.69 | 74.65 |
| 844.04 | 65.31 |
| 798.03 | 71.63 |
| 772.20 | 68.51 |
| 717.29 | 75.90 |
| 686.79 | 66.91 |
| 668.46 | 68.22 |
| 650.21 | 68.04 |
| 601.50 | 59.64 |
| 547.68 | 44.53 |
| 526.55 | 45.99 |
| 482.62 | 58.93 |
| 471.45 | 60.44 |
| 444.14 | 59.99 |
| 423.38 | 58.76 |

TABLE 26

ESYLATE (FORM β)

| WAVE NUMBER (cm$^{-1}$) | % T |
|---|---|
| 3422.06 | 93.12 |
| 3303.44 | 89.24 |
| 3128.13 | 92.01 |

TABLE 26-continued

ESYLATE (FORM β)

| WAVE NUMBER (cm$^{-1}$) | % T |
|---|---|
| 2595.94 | 92.67 |
| 2276.37 | 95.87 |
| 2051.39 | 95.50 |
| 1694.09 | 72.13 |
| 1644.75 | 84.09 |
| 1588.32 | 83.16 |
| 1529.21 | 65.27 |
| 1457.83 | 69.69 |
| 1426.95 | 85.03 |
| 1400.48 | 72.09 |
| 1385.04 | 83.40 |
| 1355.81 | 74.56 |
| 1319.88 | 77.31 |
| 1296.55 | 77.66 |
| 1253.87 | 64.28 |
| 1199.61 | 71.21 |
| 1187.91 | 69.92 |
| 1139.76 | 64.85 |
| 1092.92 | 83.86 |
| 1066.96 | 88.29 |
| 1055.19 | 86.48 |
| 1028.72 | 62.50 |
| 996.79 | 86.93 |
| 931.15 | 91.11 |
| 909.24 | 84.55 |
| 885.60 | 88.76 |
| 872.37 | 82.05 |
| 838.72 | 77.28 |
| 779.73 | 90.55 |
| 741.49 | 76.67 |
| 723.87 | 81.99 |
| 676.10 | 84.75 |
| 599.47 | 91.23 |
| 578.37 | 80.13 |
| 552.44 | 80.28 |
| 537.09 | 74.86 |
| 527.37 | 71.96 |
| 514.22 | 64.33 |
| 476.26 | 89.39 |
| 460.92 | 87.09 |
| 446.30 | 84.63 |
| 429.94 | 87.20 |
| 416.02 | 78.03 |

TABLE 27

ESYLATE (FORM β)

| WAVE NUMBER (cm$^{-1}$) | % T |
|---|---|
| 3303.18 | 78.44 |
| 3107.11 | 84.00 |
| 3000.63 | 87.00 |
| 2931.74 | 88.33 |
| 2582.21 | 87.39 |
| 2260.15 | 91.52 |
| 2040.56 | 90.88 |
| 1968.01 | 91.72 |
| 1689.52 | 55.42 |
| 1647.24 | 71.29 |
| 1587.52 | 70.97 |
| 1524.38 | 57.93 |
| 1453.72 | 46.32 |
| 1426.27 | 66.22 |
| 1398.05 | 55.56 |
| 1355.93 | 50.43 |
| 1309.97 | 80.04 |
| 1281.20 | 64.46 |
| 1241.00 | 51.31 |
| 1205.77 | 45.41 |
| 1184.19 | 43.37 |
| 1151.28 | 55.33 |

TABLE 27-continued

ESYLATE (FORM β)

| WAVE NUMBER (cm$^{-1}$) | % T |
|---|---|
| 1131.31 | 44.71 |
| 1086.08 | 65.79 |
| 1061.38 | 70.95 |
| 1049.91 | 62.19 |
| 1033.17 | 38.75 |
| 985.47 | 65.92 |
| 945.83 | 78.73 |
| 910.85 | 56.84 |
| 892.18 | 69.98 |
| 871.99 | 76.39 |
| 840.95 | 59.27 |
| 830.58 | 55.72 |
| 788.17 | 78.25 |
| 763.00 | 78.08 |
| 741.34 | 50.54 |
| 682.32 | 67.23 |
| 644.25 | 70.08 |
| 612.89 | 65.29 |
| 591.48 | 61.15 |
| 578.14 | 47.06 |
| 551.71 | 51.97 |
| 529.84 | 43.75 |
| 518.10 | 46.42 |
| 468.69 | 66.48 |
| 457.49 | 62.27 |
| 446.73 | 65.90 |
| 430.38 | 71.60 |
| 405.91 | 50.91 |

(Preparation of Pharmaceutical Composition)

1 mg tablet 24 g of a crystalline form of 4-(3-chloro-4-(cyclopropylaminocarbonyl)aminophenoxy)-7-methoxy-6-quinolinecarboxamide methanesulfonate (Form C) (hereunder, referred to as "Crystalline Form C") and 192 g of light anhydrous silicic acid (anti-gelation agent; trade name: Aerosil (registered trademark) 200, Nippon Aerosil Co., Ltd.) were mixed using a 20 L super mixer, after which 1236 g of D-mannitol (excipient; Towa Chemical Industry Co., Ltd.), 720 g of crystalline cellulose (excipient; trade name: Avicel PH 101, Asahi Chemical Industry Co., Ltd.) and 72 g of hydroxypropylcellulose (binder; trade name: HPC-L, Nippon Soda Co., Ltd.) were further added and mixed. Thereafter, a suitable amount of anhydrous ethanol was added to produce granulated products containing Crystalline Form C. The granulated products were dried with a shelf dryer (60° C.), and size-controlled using a power mill to produce granules. The obtained granules were mixed in a 20 L tumbler mixer with 120 g of croscarmellose sodium (disintegrator; trade name: Ac-Di-Sol, FMC International Inc.) and 36 g of sodium stearyl fumarate (lubricant; JRS Pharma LP), and the resulting mixture was formed into tablets with a tableting machine to produce tablets having a total weight of 100 mg. These tablets were then coated using a tablet coating machine employing a 10% aqueous solution of opadry yellow (opadry 03F42069 yellow, Colorcon (Japan) Ltd.) as a coating solution, to produce coated tablets having a total weight of 105 mg.

10 mg Tablet 60 g of Crystalline Form C and 192 g of light anhydrous silicic acid (anti-gelation agent; trade name: Aerosil (registered trademark) 200, Nippon Aerosil Co., Ltd.) were mixed using a 20 L super mixer, after which 1200 g of D-mannitol (excipient; Towa Chemical Industry Co., Ltd.), 720 g of crystalline cellulose (excipient; trade name: Avicel PH 101, Asahi Chemical Industry Co., Ltd.) and 72 g of hydroxypropylcellulose (binder; trade name: HPC-L, Nippon Soda Co., Ltd.) were further added and mixed. Thereafter, a suitable amount of anhydrous ethanol was added to produce granulated products containing Crystalline Form C. The granulated products were dried with a shelf dryer (60° C.), and size-controlled using a power mill to produce granules. The obtained granules were mixed in a 20 L tumbler mixer with 120 g of croscarmellose sodium (disintegrator; trade name: Ac-Di-Sol, FMC International Inc.) and 36 g of sodium stearyl fumarate (lubricant; JRS Pharma LP), and the resulting mixture was formed into tablets with a tableting machine to produce tables having a total weight of 400 mg. These tablets were then coated using a tablet coating machine employing a 10% aqueous solution of opadry yellow (opadry 03F42069 yellow, Colorcon (Japan) Ltd.) as a coating solution, to produce coated tablets having a total weight of 411 mg.

100 mg Tablet 31.4 of Crystalline Form C and 4 g of light anhydrous silicic acid (anti-gelation agent; trade name: Aerosil (registered trademark) 200Nippon Aerosil Co., Ltd.) were mixed using a 1 L super mixer, after which 40.1 g of anhydrous dibasic calcium phosphate (excipient; Kyowa Chemical Industry Co., Ltd.), 10 g of low-substituted hydroxypropylcellulose (binder; trade name: L-HPC (LH-21), Shin-Etsu Chemical Co., Ltd.) and 3 g of hydroxypropylcellulose (binder; trade name: HPC-L, Nippon Soda Co., Ltd.) were further added and mixed. Thereafter, a suitable amount of anhydrous ethanol was added thereto to produce granulated products containing Crystalline Form C. The granulated products were dried with a shelf dryer (60° C.), and size-controlled using a power mill to produce granules. The obtained granules were mixed with 10 g of croscarmellose sodium (disintegrator; trade name: Ac-Di-Sol, FMC International Inc.) and 1.5 g of sodium stearyl fumarate (lubricant; JRS Pharma LP), and the resulting mixture was formed into tablets with a tableting machine to produce tablets having a total weight of 400 mg.

INDUSTRIAL APPLICABILITY

The salt of 4-(3-chloro-4-(cyclopropylaminocarbonyl)aminophenoxy)-7-methoxy-6-quinolinecarboxamide, the solvate of the salt as well as the crystalline form thereof according to the present invention have excellent characteristics in terms of physical properties and pharmacokinetics, and are extremely useful as an angiogenesis inhibitor or a c-Kit kinase inhibitor.

The invention claimed is:

1. A crystalline form (Form A) of 4-(3-chloro-4-(cyclopropylaminocarbonyl)aminophenoxy)-7-methoxy-6-quinolinecarboxamide methanesulfonate having diffraction peaks at diffraction angles (2θ±0.2°) of 9.65° and 18.37° in a powder X-ray diffraction.

2. A crystalline form (Form A) of 4-(3-chloro-4-(cyclopropylaminocarbonyl)aminophenoxy)-7-methoxy-6-quinolinecarboxamide methanesulfonate having peaks at chemical shifts of about 162.4 ppm, about 128.0 ppm, about 102.3 ppm and about 9.9 ppm in a $^{13}$C Solid State Nuclear Magnetic Resonance spectrum.

3. A crystalline form (Form A) of 4-(3-chloro-4-(cyclopropylaminocarbonyl)aminophenoxy)-7-methoxy-6-quinolinecarboxamide methanesulfonate having absorption bands at wavenumbers of 1161±1 cm$^{-1}$ and 1044±1 cm$^{-1}$ in an infrared absorption spectrum.

4. A crystalline form (Form B) of 4-(3-chloro-4-(cyclopropylaminocarbonyl)aminophenoxy)-7-methoxy-6-quinolinecarboxamide methanesulfonate having diffraction peaks at diffraction angles (2θ±0.2°) of 5.72° and 13.84° in a powder X-ray diffraction.

5. A crystalline form (Form B) of 4-(3-chloro-4-(cyclopropylaminocarbonyl)aminophenoxy)-7-methoxy-6-quinolinecarboxamide methanesulfonate having absorption bands at wavenumbers of 1068±1 cm$^{-1}$ and 918±1 cm$^{-1}$ in an infrared absorption spectrum.

6. A crystalline form (Form C) of 4-(3-chloro-4-(cyclopropylaminocarbonyl)aminophenoxy)-7-methoxy-6-quinolinecarboxamide methanesulfonate having diffraction peaks at diffraction angles (2θ±0.2°) of 14.20° and 17.59° in a powder X-ray diffraction.

7. A crystalline form (Form C) of 4-(3-chloro-4-(cyclopropylaminocarbonyl)aminophenoxy)-7-methoxy-6-quinolinecarboxamide methanesulfonate having peaks at chemical shifts of about 160.2 ppm, about 126.6 ppm, about 105.6 ppm and about 7.8 ppm in a $^{13}$C Solid State Nuclear Magnetic Resonance spectrum.

8. A crystalline form (Form C) of 4-(3-chloro-4-(cyclopropylaminocarbonyl)aminophenoxy)-7-methoxy-6-quinolinecarboxamide methanesulfonate having absorption bands at wavenumbers of 1324±1 cm$^{-1}$ and 579±1 cm$^{-1}$ in an infrared absorption spectrum.

9. A crystalline form (Form F) of a hydrate of 4-(3-chloro-4-(cyclopropylaminocarbonyl)aminophenoxy)-7-methoxy-6-quinolinecarboxamide methanesulfonate having diffraction peaks at diffraction angles (2θ±0.2°) of 8.02° and 18.14° in a powder X-ray diffraction.

10. A crystalline form (Form I) of an acetic acid solvate of 4-(3-chloro-4-(cyclopropylaminocarbonyl)aminophenoxy)-7-methoxy-6-quinolinecarboxamide methanesulfonate having diffraction peaks at diffraction angles (2θ±0.2°) of 9.36° and 12.40° in a powder X-ray diffraction.

11. A crystalline form (Form I) of an acetic acid solvate of 4-(3-chloro-4-(cyclopropylaminocarbonyl)aminophenoxy)-7-methoxy-6-quinolinecarboxamide methanesulfonate having absorption bands at wavenumbers of 1750±1 cm$^{-1}$ and 1224±1 cm$^{-1}$ in an infrared absorption spectrum.

12. A crystalline form (Form α) of 4-(3-chloro-4-(cyclopropylaminocarbonyl)aminophenoxy)-7-methoxy-6-quinolinecarboxamide ethanesulfonate having diffraction peaks at diffraction angles (2θ±0.2°) of 15.70° and 17.18° in a powder X-ray diffraction.

13. A crystalline form (Form α) of 4-(3-chloro-4-(cyclopropylaminocarbonyl)aminophenoxy)-7-methoxy-6-quinolinecarboxamide ethanesulfonate having absorption bands at wavenumbers of 1320±1 cm$^{-1}$ and 997±1 cm$^{-1}$ in an infrared absorption spectrum.

14. A crystalline form (Form β) of 4-(3-chloro-4-(cyclopropylaminocarbonyl)aminophenoxy)-7-methoxy-6-quinolinecarboxamide ethanesulfonate having diffraction peaks at diffraction angles (2θ±0.2°) of 6.48° and 9.58° in a powder X-ray diffraction.

15. A crystalline form (Form β) of 4-(3-chloro-4-(cyclopropylaminocarbonyl)aminophenoxy)-7-methoxy-6-quinolinecarboxamide ethanesulfonate having absorption bands at wavenumbers of 1281±1 cm$^{-1}$ and 985±1 cm$^{-1}$ in an infrared absorption spectrum.

16. A process for preparing a crystalline form of 4-(3-chloro-4-(cyclopropylaminocarbonyl)aminophenoxy)-7-methoxy-6-quinolinecarboxamide methanesulfonate (Form A), comprising a step of mixing 4-(3-chloro-4-(cyclopropylaminocarbonyl)aminophenoxy)-7-methoxy-6-quinolinecarboxamide, methanol and methanesulfonic acid to dissolve.

17. A process for preparing a crystalline form of 4-(3-chloro-4-(cyclopropylaminocarbonyl)aminophenoxy)-7-methoxy-6-quinolinecarboxamide methanesulfonate (Form A), comprising:
  mixing 4-(3-chloro-4-(cyclopropylaminocarbonyl)aminophenoxy)-7-methoxy-6-quinolinecarboxamide, acetic acid and methanesulfonic acid to dissolve; and
  adding ethanol to the mixture.

18. A process for preparing a crystalline form of 4-(3-chloro-4-(cyclopropylaminocarbonyl)aminophenoxy)-7-methoxy-6-quinolinecarboxamide methanesulfonate (Form B), comprising a step of drying a crystalline form of the acetic acid solvate of 4-(3-chloro-4-(cyclopropylaminocarbonyl)aminophenoxy)-7-methoxy-6-quinolinecarboxamide methanesulfonate (Form I) at 30° C. for 3 hours and at 40° C. for 16 hours to remove acetic acid.

19. A process for preparing a crystalline form of 4-(3-chloro-4-(cyclopropylaminocarbonyl)aminophenoxy)-7-methoxy-6-quinolinecarboxamide methanesulfonate (Form C), comprising a step of heating a crystalline form of the dimethyl sulfoxide solvate of 4-(3-chloro-4-(cyclopropylaminocarbonyl)aminophenoxy)-7-methoxy-6-quinolinecarboxamide methanesulfonate at 115° C. for 10 hours.

20. A process for preparing a crystalline form of 4-(3-chloro-4-(cyclopropylaminocarbonyl)aminophenoxy)-7-methoxy-6-quinolinecarboxamide methanesulfonate (Form C), comprising a step of mixing a crystalline form of the acetic acid solvate of 4-(3-chloro-4-(cyclopropylaminocarbonyl)aminophenoxy)-7-methoxy-6-quinolinecarboxamide methanesulfonate (Form I) and ethanol.

21. A process for preparing a crystalline form of 4-(3-chloro-4-(cyclopropylaminocarbonyl)aminophenoxy)-methoxy-6-quinolinecarboxamide Methanesulfonate (Form C), comprising:
  mixing 4-(3-chloro-4-(cyclopropylaminocarbonyl)aminophenoxy)-7-methoxy-6-quinolinecarboxamide, acetic acid and methanesulfonic acid to dissolve; and
  adding 2-propanol to the mixture.

22. A process for preparing a crystalline form of 4-(3-chloro-4-(cyclopropylaminocarbonyl)aminophenoxy)-7-methoxy-6-quinolinecarboxamide methanesulfonate (Form C), comprising a step of humidifying a crystalline form of 4-(3-chloro-4-(cyclopropylaminocarbonyl)aminophenoxy)-7-methoxy-6-quinolinecarboxamide methanesulfonate (Form B).

23. A process for preparing a crystalline form of the hydrate of 4-(3-chloro-4-(cyclopropylaminocarbonyl)aminophenoxy)-7-methoxy-6-quinolinecarboxamide methanesulfonate (Form F), comprising:
  mixing 4-(3-chloro-4-(cyclopropylaminocarbonyl)aminophenoxy)-7-methoxy-6-quinolinecarboxamide, acetic acid and methanesulfonic acid to dissolve and
  adding ethyl acetate to the mixture.

24. A process for preparing a crystalline form of the acetic acid solvate of 4-(3-chloro-4-(cyclopropylaminocarbonyl)aminophenoxy)-7-methoxy-6-quinolinecarboxamide methanesulfonate (Form I), comprising:
  mixing 4-(3-chloro-4-(cyclopropylaminocarbonyl)aminophenoxy)-7-methoxy-6-quinolinecarboxamide, acetic acid and methanesulfonic acid to dissolve; and
  adding 1-propanol to the mixture.

25. A process for preparing a crystalline form of 4-(3-chloro-4-(cyclopropylaminocarbonyl)aminophenoxy)-7-methoxy-6-quinolinecarboxamide ethanesulfonate (Form α), comprising a step of mixing 4-(3-chloro-4-(cyclopropylaminocarbonyl)aminophenoxy)-7-methoxy-6-quinolinecarboxamide, dimethyl sulfoxide and ethanesulfonic acid to dissolve.

26. A process for preparing a crystalline form of 4-(3-chloro-4-(cyclopropylaminocarbonyl)aminophenoxy)-7-methoxy-6-quinolinecarboxamide ethanesulfonate (Form β), comprising a step of mixing a crystalline form of 4-(3-chloro-4-(cyclopropylaminocarbonyl)aminophenoxy)-7-methoxy-6-quinolinecarboxamide ethanesulfonate (Form α) and ethanol.

27. A process for preparing a crystalline form of 4-(3-chloro-4-(cyclopropylaminocarbonyl)aminophenoxy)-7-methoxy-6-quinolinecarboxamide ethanesulfonate (Form β), comprising:
mixing 4-(3-chloro-4-(cyclopropylaminocarbonyl)aminophenoxy)-7-methoxy-6-quinolinecarboxamide, acetic acid and ethanesulfonic acid to dissolve; and
adding 2-propanol and water to the mixture.

28. A pharmaceutical composition in the form of a tablet, powder, granule, capsule or lozenge, said pharmaceutical composition comprising the crystalline form according to claim 15; and
a pharmaceutically acceptable carrier.

* * * * *

UNITED STATES PATENT AND TRADEMARK OFFICE
CERTIFICATE OF CORRECTION

PATENT NO. : 7,612,208 B2  Page 1 of 1
APPLICATION NO. : 10/577531
DATED : November 3, 2009
INVENTOR(S) : Matsushima et al.

It is certified that error appears in the above-identified patent and that said Letters Patent is hereby corrected as shown below:

On the Title Page,

Item [*] Notice: Subject to any disclaimer, the term of this patent is extended or adjusted under 35 USC 154(b) by 485 days.

Delete the phrase "by 485 days" and insert -- by 636 days --

Signed and Sealed this

Twenty-seventh Day of July, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,612,208 B2 | |
| APPLICATION NO. | : 10/577531 | |
| DATED | : November 3, 2009 | |
| INVENTOR(S) | : Matsushima et al. | |

It is certified that error appears in the above-identified patent and that said Letters Patent is hereby corrected as shown below:

Column 50
Line 10, delete "claim 15" and insert -- claim 6 --.

Signed and Sealed this
Eleventh Day of October, 2011

David J. Kappos
*Director of the United States Patent and Trademark Office*